US011869661B2

(12) United States Patent
Maher

(10) Patent No.: US 11,869,661 B2
(45) Date of Patent: Jan. 9, 2024

(54) SYSTEMS AND METHODS FOR DETERMINING WHETHER A SUBJECT HAS A CANCER CONDITION USING TRANSFER LEARNING

(71) Applicant: GRAIL, LLC, Menlo Park, CA (US)

(72) Inventor: M. Cyrus Maher, San Mateo, CA (US)

(73) Assignee: GRAIL, LLC, Menlo Park, CA (US)

( * ) Notice: Subject to any disclaimer, the term of this patent is extended or adjusted under 35 U.S.C. 154(b) by 735 days.

(21) Appl. No.: 16/881,928

(22) Filed: May 22, 2020

(65) Prior Publication Data

US 2020/0372296 A1 Nov. 26, 2020

Related U.S. Application Data

(60) Provisional application No. 62/851,486, filed on May 22, 2019.

(51) Int. Cl.
| | | |
|---|---|---|
| G16H 50/20 | (2018.01) | |
| G16H 50/70 | (2018.01) | |
| G16H 50/30 | (2018.01) | |
| G06F 18/2115 | (2023.01) | |
| C12Q 1/6886 | (2018.01) | |

(52) U.S. Cl.
CPC ......... *G16H 50/20* (2018.01); *G06F 18/2115* (2023.01); *G16H 50/30* (2018.01); *G16H 50/70* (2018.01); *C12Q 1/6886* (2013.01)

(58) Field of Classification Search
CPC ........ G16H 50/20; G16H 50/30; G16H 50/70; G06F 18/2115
See application file for complete search history.

(56) References Cited

U.S. PATENT DOCUMENTS

| | | |
|---|---|---|
| 2015/0299808 A1 | 10/2015 | Gonzalez Diaz et al. |
| 2019/0130065 A1 | 5/2019 | Lo et al. |
| 2019/0287652 A1 | 9/2019 | Gross et al. |

FOREIGN PATENT DOCUMENTS

| | | |
|---|---|---|
| WO | WO 2018/009723 A1 | 1/2018 |
| WO | WO 2018/081130 A1 | 5/2018 |
| WO | WO 2019/079166 A1 | 4/2019 |
| WO | WO 2019/084559 A1 | 5/2019 |
| WO | WO 2019/195268 A3 | 10/2019 |
| WO | WO 2020/069350 A1 | 4/2020 |
| WO | WO 2020/154682 A2 | 7/2020 |

OTHER PUBLICATIONS

Antropova, et al., "A deep feature fusion methodology for breast cancer diagnosis demonstrated on three imaging modality datasets," Medical Physics, 44(10), pp. 5162-5171, 2017.
Agresti, *An Introduction to Categorical Data Analysis*, 1996, Chapter 5, pp. 103-144.
Alkan et al., 2009, Nat Genet 41:1061-7.
Benjamini et al., 2012, Nucleic Acids Research 40(10): e72.
Blum et al., 2018, "TCGA-Analyzed Tumors," SNAPSHOT 173(2), p. 530.
Boeva et al., 2011, Bioinformatics 27(2), p. 268.
Boser et al., 1992, "A training algorithm for optimal margin classifiers," in Proceedings of the 5th Annual ACM Workshop on Computational Learning Theory, ACM Press, Pittsburgh, Pa., pp. 142-152.
Breiman, 1999, "Random Forests—Random Features," Technical Report 567, Statistics Department, U.C. Berkeley, Sep. 1999.
Casadio et al., 2013, "Urine cell-free DNA integrity as a marker for early bladder cancer diagnosis: preliminary data," Urol Oncol. 2013;31(8):1744-1750.
Cavalcante et al. and Sartor, 2017, "annotatr: genomic regions in context," Bioinformatics33(15):2381-2383.
Chan et al., "Clinical Sciences Reviews Committee of the Association of Clinical Biochemists Cell-free nucleic acids in plasma, serum and urine: a new tool in molecular diagnosis," Ann Clin Biochem. 2003;40(Pt 2):122-130.
Cristianini et al., 2000, "An Introduction to Support Vector Machines," Cambridge University Press, Cambridge.
Cunningham, 2007, "Dimension Reduction," University College Dublin, Technical Report UCD-CSI-2007-7.
De Mattos-Arruda et al., 2016, "Cell-free circulating tumour DNA as a liquid biopsy in breast cancer," Mol Oncol. 2016;10(3):464-474.
Duda, *Pattern Classification*, Second Edition, 2001, John Wiley & Sons, Inc., pp. 259, 262-265.
Duda, 2001, *Pattern Classification*, John Wiley & Sons, Inc., New York, pp. 395-396.
Duda, 2001, Pattern Classification, John Wiley & Sons, Inc., New York, pp. 396-408 and pp. 411-412.
Fodor, 2002, "A survey of dimension reduction techniques," Center for Applied Scientific Computing, Lawrence Livermore National, Technical Report UCRL-ID-148494.
Frenel et al., 2015, Serial next-generation sequencing of circulating cell-free DNA evaluating tumor clone response to molecularly targeted drug administration. Clin Cancer Res. 21(20):4586-4596.
Furey et al., 2000, *Bioinformatics* 16, 906-914.
Goessl et al., "Fluorescent methylation-specific polymerase chain reaction for DNA-based detection of prostate cancer in bodily fluids," Cancer Res. 2000;60(21):5941-5945.

(Continued)

*Primary Examiner* — Jerry Lin
(74) *Attorney, Agent, or Firm* — Bookoff McAndrews, PLLC

(57) ABSTRACT

Systems and methods for classifier training are provided. A first dataset is obtained that comprises, for each first subject, a corresponding plurality of bin values, each for a bin in a plurality of bins, and subject cancer condition. A feature extraction technique is applied to the first dataset thereby obtaining feature extraction functions, each of which is an independent linear or nonlinear function of bin values of the bins. A second dataset is obtained comprising, for each second subject, a corresponding plurality of bin values, each for a bin in the plurality of bins and subject cancer condition. The plurality of bin values of each corresponding subject in the second plurality are projected onto the respective feature extraction functions, thereby forming a transformed second dataset comprising feature values for each subject. The transformed second dataset and subject cancer condition serves to train a classifier on the cancer condition set.

21 Claims, 30 Drawing Sheets

(56) References Cited

OTHER PUBLICATIONS

Hao et al., "Circulating cell-free DNA in serum as a biomarker for diagnosis and prognostic prediction of colorectal cancer," Br J Cancer. 2014;111(8):1482-1489.

Hassoun, 1995, Fundamentals of Artificial Neural Networks, Massachusetts Institute of Technology.

Hastie, 2001, *The Elements of Statistical Learning*, Springer, New York.

Heitzer et al., 2013, "Establishment of tumor-specific copy number alterations from plasma DNA of patients with cancer," Int J Cancer. 133(2):346-356.

Heitzer et al., 2015, "Circulating tumor DNA as a liquid biopsy for cancer," Clin Chem. 61(1):112-123.

Jensen et al., 2013, PLoS One 8; e57381.

Jones, 2002, Oncogene 21:5358-5360.

Kim et al., 2014, "Circulating cell-free DNA as a promising biomarker in patients with gastric cancer: diagnostic validity and significant reduction of cfDNA after surgical resection," Ann Surg Treat Res. 2014;86(3):136-142.

Kircher et al., 2012, Nucleic Acids Research 40, No. 1 e3.

Langmead et al., 2012, Nat Methods 9, pp. 357-359.

Larochelle et al., 2009, "Exploring strategies for training deep neural networks," J Mach Learn Res 10, pp. 1-40.

Leek et al., 2007, PLoS Genet 3, pp. 1724-1735.

Li et al., 2014, Front. Genet. 5, p. 318.

Liu et al., 2018 Ann Oncol., doi: 10.1093/annonc/mdy513.

Liu et al., "Sensitive and specific multi-cancer detection and localization using methylation signatures in cell-free DNA," Ann. Oncol 2020, https://doi.org/10.1016/j.annonc.2020.02.011.

Lo et al., 2010, "Maternal plasma DNA sequencing reveals the genome-wide genetic and mutational profile of the fetus," Sci Transl Med. 2(61):61ra91.

Miller et al., 2011, PLoS ONE 6(1), p. e16327.

O'Marcaigh et al., 1993, "Estimating The Predictive Value of a Diagnostic Test, How to Prevent Misleading or Confusing Results," Clin. Ped. 32(8): 485-491.

Padmaja, L. et al. (Aug. 18, 2016). 2016 IEEE 6th International Conference on Advanced Computing (IACC). pp. 31-34. doi:10.1109/IACC.2016.16, ISBN 978-1-4673-8286-1.

Paska et al., 2015, Biochemia Medica 25(2):161-176.

Price et al., 2006, Nat Genet 38, pp. 904-909.

Raptis et al., 1980, "Quantitation and characterization of plasma DNA in normals and patients with systemic lupus erythematosus," J Clin Invest. 66(6):1391-1399.

Rumelhart et al., 1988, "Neurocomputing: Foundations of research," ch. Learning Representations by Back-propagating Errors, pp. 696-699.

Salvi et al., 2016, "Cell-free DNA as a diagnostic marker for cancer: current insights," Onco Targets Ther. 9:6549-6559.

Shao et al. 2015 "Quantitative analysis of cell-free DNA in ovarian cancer," Oncol Lett. 2015;10(6):3478-3482.

Shapiro et al., 1983, "Determination of circulating DNA levels in patients with benign or malignant gastrointestinal disease," Cancer. 51(11):2116-2120.

Sozzi et al., 2003 "Quantification of free circulating DNA as a diagnostic marker in lung cancer," J Clin Oncol. 21(21):3902-3908.

Stroun et al., "Neoplastic characteristics of the DNA found in the plasma of cancer patients," Oncology. 1989;46(5):318-322.

Swanton et al., 2017, "Phylogenetic ctDNA analysis depicts early stage lung cancer evolution," Nature, 545(7655): 446-451.

Vapnik, 1998, *Statistical Learning Theory*, Wiley, New York; Mount, 2001, *Bioinformatics: sequence and genome analysis*, Cold Spring Harbor Laboratory Press, Cold Spring Harbor, N.Y.

Vincent et al., 2010, "Stacked denoising autoencoders: Learning useful representations in a deep network with a local denoising criterion," J Mach Learn Res 11, pp. 3371-3408.

Vogelstin et al., 2013, "Cancer genome landscapes," Science 339 1546-1558.

Warton et al.,, 2015, Front Mol Biosci, 2(13) doi: 10.3389/fmolb.2015.00013.

Yoon et al., 2009, Genome Research 19(9):1586).

Yoon, 2009, "Hidden Markov Models and their Applications in Biological Sequence Analysis," Curr. Genomics. Sep. 10(6): 402-415.

Yosinski et al., 2014, "How transferable are features in deep neural networks?", Advances in Neural Information Processing Systems 27, pp. 3320-3328.

Zahorian et al., 2011, "Nonlinear Dimensionality Reduction Methods for Use with Automatic Speech Recognition," Speech Technologies. doi: 10.5772/16863. ISBN 978-953-307-996-7.

Zeiler, 2012 "ADADELTA: an adaptive learning rate method," CoRR, vol. abs/1212.5701.

Zhao et al., 2015, Clinical Chemistry 61(4), pp. 608-616.

Zonta et al., "Assessment of DNA integrity, applications for cancer research," Adv Clin Chem. 2015;70:197-246.

U.S. Appl. No. 15/793,830, filed Oct. 25, 2017.

U.S. Appl. No. 15/931,022, entitled "Model Based Featurization and Classification," filed May 13, 2020.

U.S. Appl. No. 16/201,912 entitled "Models for Targeted Sequencing," filed Nov. 27, 2018.

U.S. Appl. No. 16/352,214 entitled "Identifying Copy Number Aberrations," filed Mar. 13, 2019.

U.S. Appl. No. 16/352,602, entitled "Anomalous Fragment Detection and Classification," filed Mar. 13, 2019.

U.S. Appl. No. 16/352,739, entitled "Method and System for Selecting, Managing, and Analyzing Data of High Dimensionality," filed Mar. 13, 2019.

First Data Set (e.g., TCGA)

| | Class label | Bin 1 Value | Bin 2 Value | Bin 3 Value | ... | Bin N Value |
|---|---|---|---|---|---|---|
| Subject 1-1 | $L_{1-1}$ | $cnt_{1-1-1}$ | $cnt_{1-1-2}$ | $cnt_{1-1-3}$ | ... | $cnt_{1-1-N}$ |
| Subject 1-2 | $L_{1-2}$ | $cnt_{1-2-1}$ | $cnt_{1-2-2}$ | $cnt_{1-2-3}$ | ... | $cnt_{1-2-N}$ |
| ... | ... | ... | ... | ... | ... | ... |
| Subject 1-Z | $L_{1-Z}$ | $cnt_{1-Z-1}$ | $cnt_{1-Z-2}$ | $cnt_{1-Z-3}$ | ... | $cnt_{1-Z-N}$ |

Second Data Set (e.g., CCGA)

| | Class label | Bin 1 Value | Bin 2 Value | Bin 3 Value | ... | Bin N Value |
|---|---|---|---|---|---|---|
| Subject 2-1 | $L_{2-1}$ | $cnt_{2-1-1}$ | $cnt_{2-1-2}$ | $cnt_{2-1-3}$ | ... | $cnt_{2-1-N}$ |
| Subject 2-2 | $L_{2-2}$ | $cnt_{2-2-1}$ | $cnt_{2-2-2}$ | $cnt_{2-2-3}$ | ... | $cnt_{2-2-N}$ |
| ... | ... | ... | ... | ... | ... | ... |
| Subject 2-T | $L_{2-T}$ | $cnt_{2-T-1}$ | $cnt_{2-T-2}$ | $cnt_{2-T-3}$ | ... | $cnt_{2-T-N}$ |

Figure 3

1044

(C) Transform, based on at least each respective feature extraction function in the first plurality of feature extraction functions, the respective second plurality of bin values of each corresponding subject in the second plurality of subjects against the respective feature extraction function, thereby contributing to a transformed second dataset comprising a respective plurality of feature values for each corresponding subject.

1046

The first feature extraction technique is a first convolutional neural network that comprises a first plurality of convolutional layers, each respective convolutional layer in the first plurality of convolutional layers is associated with a learned weight vector that is obtained through back-propagation of the first convolutional neural network using the respective bin values and respective indications of the cancer condition of respective subjects in the first dataset, and the respective learned weight vector of each convolutional layer in a subset of the first plurality of convolutional layers collectively represent the first plurality of feature extraction functions. The transforming (C) comprises inputting the corresponding second plurality of bin values of a respective subject in the second plurality of subjects into a second convolutional network that comprises the subset of the first plurality of convolutional layers. A weight vector of each respective convolutional layer in the second convolutional neural network is initialized and in some embodiments frozen at values of the learned weight vector of the corresponding convolutional layer in the first convolutional neural network.

1048

The first plurality of convolutional layers comprises three, four, five, seven, or eight convolutional layers.

1050

The first plurality of convolutional layers comprises five convolutional layers and the subset of the first plurality of convolutional layers consists of the first three convolutional layers of the first convolutional neural network.

1051

The transforming (C) is based on each respective feature extraction function in the first plurality of feature extraction functions and a second plurality of feature extraction functions. The second plurality of feature extraction functions is obtained by applying a second feature extraction technique to the respective bin values of respective subjects in the second dataset, thereby identifying a second plurality of feature extraction functions. Each feature extraction function in the second plurality of feature extraction functions independently encodes a linear or nonlinear function of bin values of all or a subset of the plurality of bins, and the second plurality of feature extraction functions collectively discriminates respective subjects in the second plurality of subjects as having a cancer condition within the cancer condition set based on respective bin values for the respective subjects.

Figure 10E

| primccat | CCGA + TCGA (balanced) | CCGA (balanced) |
|---|---|---|
| Ovarian | 0.5 | 0.25 |
| Head/Neck | 0.67 | 0.33 |
| Lymphoma | 0.2 | 0.33 |
| Multiple myeloma | 0.64 | 0.55 |
| Colorectal | 0.52 | 0.3 |
| Pancreas | 0.33 | 0.2 |
| Lung | 0.52 | 0.55 |
| Hepatobiliary | 0.33 | 0.11 |
| Breast | 0.48 | 0.45 |
| Leukemia | 0.25 | 0.25 |
| Esophageal | 0 | 0.2 |
| Other | 0.11 | 0 |

Figure 12

```
┌─────────────────────────────────────────────┐
│   Generate data structure for a control group │
│                    2100                      │
└─────────────────────────────────────────────┘

┌─────────────────────────────────────────────┐
│   Generate set of methylation state vectors  │
│            for a control group               │
│                    2052                      │
└─────────────────────────────────────────────┘
                      ↓
┌─────────────────────────────────────────────┐
│  For each methylation state vector, subdivide into │
│         strings of methylation sites         │
│                    2105                      │
└─────────────────────────────────────────────┘
                      ↓
┌─────────────────────────────────────────────┐
│  Tally strings for each position and methylation │
│              state combination               │
│                    2110                      │
└─────────────────────────────────────────────┘
                      ↓
┌─────────────────────────────────────────────┐
│  Create data structure storing counts of all │
│      possible strings from the control group │
│                    2115                      │
└─────────────────────────────────────────────┘
```

Figure 21

SYSTEMS AND METHODS FOR DETERMINING WHETHER A SUBJECT HAS A CANCER CONDITION USING TRANSFER LEARNING

CROSS REFERENCE TO RELATED APPLICATION

This application claims priority to United States Provisional Patent Application No. 62/851,486 entitled "SYSTEMS AND METHODS FOR DETERMINING WHETHER A SUBJECT HAS A CANCER CONDITION USING TRANSFER LEARNING," filed May 22, 2019, which is hereby incorporated by reference.

TECHNICAL FIELD

This specification describes using transfer learning to determine whether a subject has a cancer condition.

BACKGROUND

The increasing knowledge of the molecular basis for cancer and the rapid development of next generation sequencing techniques are advancing the study of early molecular alterations involved in cancer development in body fluids. Large scale sequencing technologies, such as next generation sequencing (NGS), have afforded the opportunity to achieve sequencing at costs that are less than one U.S. dollar per million bases, and in fact costs of less than ten U.S. cents per million bases have been realized. Specific genetic and epigenetic alterations associated with such cancer development are found in plasma, serum, and urine cell-free DNA (cfDNA). Such alterations could potentially be used as diagnostic biomarkers for several classes of cancers. See, Salvi et al., 2016, Onco Targets Ther. 9:6549-6559.

Cell-free DNA (cfDNA) can be found in serum, plasma, urine, and other body fluids (Chan et al., 2003, Ann Clin Biochem. 40(Pt 2):122-130) representing a "liquid biopsy," which is a circulating picture of a specific disease. See, De Mattos-Arruda and Caldas, 2016, Mol Oncol. 10(3):464-474. This represents a potential, non-invasive method of screening for a variety of cancers.

The existence of cfDNA was demonstrated by Mandel and Metais decades ago (Mandel and Metais, 1948, C R Seances Soc Biol Fil. 142(3-4):241-243). cfDNA originates from necrotic or apoptotic cells, and it is generally released by all types of cells. Stroun et al. further showed that specific cancer alterations could be found in the cfDNA of patients. See, Stroun et al., 1989 Oncology 1989 46(5):318-322. A number of subsequent articles confirmed that cfDNA contains specific tumor-related alterations, such as mutations, methylation, and copy number variations (CNVs), thus confirming the existence of circulating tumor DNA (ctDNA). See Goessl et al., 2000 Cancer Res. 60(21):5941-5945 and Frenel et al., 2015, Clin Cancer Res. 21(20):4586-4596.

cfDNA in plasma or serum is well characterized, while urine cfDNA (ucfDNA) has been traditionally less characterized. However, recent studies demonstrated that ucfDNA could also be a promising source of biomarkers (e.g., Casadio et al., 2013, Urol Oncol. 31(8):1744-1750).

In blood, apoptosis is a frequent event that determines the amount of cfDNA. In cancer patients, however, the amount of cfDNA seems to be also influenced by necrosis. See, Hao et al., 2014, Br J Cancer 111(8):1482-1489 and Zonta et al., 2015 Adv Clin Chem. 70:197-246. Since apoptosis seems to be the main release mechanism circulating cfDNA has a size distribution that reveals an enrichment in short fragments of about 167 bp corresponding to nucleosomes generated by apoptotic cells. See, Heitzer et al., 2015, Clin Chem. 61(1): 112-123 and Lo et al., 2010, Sci Transl Med. 2(61):61ra91.

The amount of circulating cfDNA in serum and plasma seems to be significantly higher in patients with tumors than in healthy controls, especially in those with advanced-stage tumors than in early-stage tumors. See Sozzi et al., 2003, J Clin Oncol. 21(21):3902-3908, Kim et al., 2014, Ann Surg Treat Res. 86(3):136-142; and Shao et al., 2015, Oncol Lett. 10(6):3478-3482. The variability of the amount of circulating cfDNA is higher in cancer patients than in healthy individuals, (see, Heitzer et al., 2013, Int J Cancer. 133(2): 346-356), and the amount of circulating cfDNA is influenced by several physiological and pathological conditions, including proinflammatory diseases (see, Raptis and Menard, 1980, J Clin Invest. 66(6):1391-1399, and Shapiro et al., 1983, Cancer 51(11):2116-2120).

Methylation status and other epigenetic modifications are known to be correlated with the presence of some disease conditions such as cancer (see, Jones, 2002, Oncogene 21:5358-5360). And specific patterns of methylation have been determined to be associated with particular cancer conditions. See Paska and Hudler, 2015, Biochemia Medica 25(2):161-176. Warton and Samimi have demonstrated that methylation patterns can be observed even in cell free DNA (Warton and Samimi, 2015, Front Mol Biosci, 2(13) doi: 10.3389/fmolb.2015.00013).

Given the promise of circulating cfDNA, as well as other forms of genotypic data, as a diagnostic indicator, improved ways of assessing such data to identify a cancer condition in subjects are needed in the art.

SUMMARY

One aspect of the present disclosure provides a computer system for training one or more classifiers to discriminate between each cancer condition in a cancer condition set. The cancer condition set comprise two or more cancer conditions. The computer system comprises at least one processor and a memory storing at least one program for execution by the at least one processor.

The at least one program comprises instructions for providing a first plurality of feature extraction functions based on a first dataset. The first dataset comprises, for each respective subject in a first plurality of subjects of a species, corresponding first genotypic information comprising (i) a corresponding first plurality of bin values, each respective bin value in the corresponding first plurality of bin values for a corresponding bin in a plurality of bins and (ii) an indication of a cancer condition of the respective subject in the cancer condition set.

Each bin in the plurality of bins represents a portion of a reference genome of the species.

The corresponding first plurality of bin values of each respective subject in the first plurality of subjects is obtained from a corresponding biological sample of the respective subject, which comprises a first tissue type, using a corresponding first plurality of sequence reads determined by a first nucleic acid sequencing method.

The first plurality of feature extraction functions is obtained by applying a first feature extraction technique to the respective bin values of respective subjects in the first dataset, thereby identifying the first plurality of feature extraction functions. Each feature extraction function in the first plurality of feature extraction functions independently encodes a linear or nonlinear function of bin values of all or a subset of the plurality of bins. The first plurality of feature extraction functions collectively discriminates respective subjects in the first plurality of subjects as having a cancer condition within the cancer condition set based on respective bin values for the respective subjects.

The at least one program further comprises instructions for obtaining a second dataset comprising, for each respective subject in a second plurality of subjects of the species, corresponding second genotypic information comprising (i) a corresponding second plurality of bin values, each respective bin value in the corresponding second plurality of bin values representing a corresponding bin in the plurality of bins and (ii) an indication of a cancer condition of the respective subject in the cancer condition set. The corresponding second plurality of bin values of each respective subject in the second plurality of subjects is obtained from a corresponding biological sample of the respective subject, which comprises a second tissue type, using a corresponding second plurality of sequence reads determined by a second nucleic acid sequencing method.

At least the first nucleic acid sequencing method differs from the second nucleic acid sequencing method or the first tissue type differs from the second tissue type.

The at least one program further comprises instructions for transforming, based on at least each respective feature extraction function in the first plurality of feature extraction functions, the respective second plurality of bin values of each corresponding subject in the second plurality of subjects against the respective feature extraction function, thereby contributing to a transformed second dataset a respective plurality of feature values for each corresponding subject.

The at least one program further comprises instructions for using the transformed second dataset and the indication of the cancer condition of respective subjects in the second plurality of subjects to train a first classifier in the one or more classifiers on at least a pair of cancer conditions in the cancer condition set.

In some embodiments, each respective bin value in the first plurality of bin values or the second plurality of bin values is representative of a number of sequence reads measured from cell free nucleic acids in the corresponding biological sample that are associated with the respective bin.

In some embodiments, the first or second nucleic acid sequencing method is targeted or whole genome sequencing.

In some embodiments, the first nucleic acid sequencing method is targeted sequencing using a plurality of nucleic acid probes, and the second nucleic acid sequencing method is whole genome sequencing. In some alternative embodiments, the first nucleic acid sequencing method is whole genome sequencing, and the second nucleic acid sequence method is targeted sequencing using a plurality of nucleic acid probes.

In some embodiments, each respective bin value in the first plurality of bin values or the second plurality of bin values is representative of a number of sequence reads associated with the respective bin in the plurality of bins or a respective methylation pattern measured in the corresponding biological sample for the respective bin in the plurality of bins.

In some embodiments, the corresponding biological sample of the respective subject in the first plurality or second plurality of subjects comprises blood, whole blood, plasma, serum, urine, cerebrospinal fluid, fecal, saliva, sweat, tears, pleural fluid, pericardial fluid, or peritoneal fluid of the respective subject.

In some embodiments, the first tissue type is blood and the corresponding biological sample for each respective subject in the first plurality of subjects is blood, and the second tissue type is one of breast tissue, lung tissue, prostate tissue, colorectal tissue, renal tissue, uterine tissue, pancreatic tissue, esophagus tissue, head/neck tissue, ovarian tissue, hepatobiliary tissue, cervical tissue, thyroid tissue, bladder tissue, and the corresponding biological sample for each respective subject in the second plurality of subjects consists of the second tissue type.

In some embodiments, the first tissue type is blood and the corresponding biological sample for each respective subject in the first plurality of subjects is blood, and the second tissue type is one of breast tissue, lung tissue, prostate tissue, colorectal tissue, renal tissue, uterine tissue, pancreatic tissue, esophagus tissue, head/neck tissue, ovarian tissue, hepatobiliary tissue, cervical tissue, thyroid tissue, bladder tissue, and the corresponding biological sample for each respective subject in the second plurality of subjects comprises a solid tumor of the second tissue type.

In some embodiments, the first tissue type is one of breast tissue, lung tissue, prostate tissue, colorectal tissue, renal tissue, uterine tissue, pancreatic tissue, esophagus tissue, head/neck tissue, ovarian tissue, hepatobiliary tissue, cervical tissue, thyroid tissue, bladder tissue, and the corresponding biological sample for each respective subject in the first plurality of subjects consists of the first tissue type, and the second tissue type is blood and the corresponding biological sample for each respective subject in the second plurality of subjects is blood.

In some embodiments, the first tissue type is one of breast tissue, lung tissue, prostate tissue, colorectal tissue, renal tissue, uterine tissue, pancreatic tissue, esophagus tissue, head/neck tissue, ovarian tissue, hepatobiliary tissue, cervical tissue, thyroid tissue, bladder tissue, and the corresponding biological sample for each respective subject in the first plurality of subjects comprises a solid tumor of the first tissue type, and the first tissue type is blood and the corresponding biological sample for each respective subject in the second plurality of subjects is blood.

In some embodiments, each respective subject in the first plurality of subjects comprises a solid tumor of the first tissue type, the second tissue type is blood and the corresponding biological sample for each respective subject in the second plurality of subjects is blood.

In some embodiments, the first tissue type is blood, the corresponding biological sample for each respective subject in the first plurality of subjects is blood, and each respective subject in the second plurality of subjects comprises a solid tumor of the second tissue type.

In some embodiments, the instructions for transforming makes use of each respective feature extraction function in the first plurality of feature extraction functions and a second plurality of feature extraction functions. In such embodiments, the second plurality of feature extraction functions is obtained by applying a second feature extraction technique to the respective bin values of respective subjects in the second dataset, thereby identifying the second plurality of feature extraction functions. Each feature extraction function in the second plurality of feature extraction functions independently encodes a linear or nonlinear function of bin values of all or a subset of the plurality of bins. Moreover, the second plurality of feature extraction functions collectively discriminates respective subjects in the second plurality of subjects as having a cancer condition within the cancer condition set based on respective bin values for the respective subjects.

In some embodiments, the cancer condition set comprises three or more cancer conditions and, for each respective cancer condition in the cancer condition set, there are two or more subjects in the first plurality of subjects that have the respective cancer condition. Further, for each respective pair of cancer conditions in the cancer condition set, the applying the first feature extraction technique is performed by applying an instance of the first feature extraction technique to the respective bin values of respective subjects in the first dataset that have either a first cancer condition or a second cancer condition in the respective pair of cancer conditions. Further still, each instance of the first feature extraction technique contributes a corresponding subset of the first plurality of feature extraction functions to the first plurality of feature extraction functions.

In some embodiments, the at least one program further comprises instructions for applying a second feature extraction technique to the respective bin values of respective subjects in the second dataset, thereby identifying a second plurality of feature extraction functions. In such embodiments, each feature extraction function in the second plurality of feature extraction functions independently encodes a linear or nonlinear function of bin values of all or a subset of the plurality of bins. Further still, the second plurality of feature extraction functions collectively discriminates respective subjects in the second plurality of subjects as having a cancer condition within the cancer condition set based on respective bin values for the respective subjects. In such embodiments, application of the second plurality of feature extraction functions to the respective bin values of respective subjects in the second dataset is used to obtain a respective plurality of second feature values for each corresponding subject in the second dataset and the transformed second dataset further comprises the respective plurality of second feature values.

In some embodiments, for each respective pair of cancer conditions in the cancer condition set, the applying the second feature extraction technique is performed by applying an instance of the second feature extraction technique to the respective bin values of respective subjects in the second dataset that have either a first cancer condition or a second cancer condition in the respective pair of cancer conditions, and each instance of the second feature extraction technique contributes a corresponding subset of the second plurality of feature extraction functions to the second plurality of feature extraction functions.

In some embodiments, the cancer condition set consists of between two and five unique cancer conditions, at least ten unique cancer conditions, at least 20 unique cancer conditions, or at least 22 unique cancer conditions.

In some embodiments, each corresponding subset of the first plurality of feature extraction functions consists of between four and one hundred feature extraction functions.

In some embodiments, each corresponding subset of the first plurality of feature extraction functions consists of between four and one hundred feature extraction functions, and each corresponding subset of the second plurality of feature extraction functions consists of between four and one hundred feature extraction functions.

In some embodiments, the applying the first feature extraction technique comprises applying a dimension reduction algorithm to the subjects in the first dataset that have either a first cancer condition or a second cancer condition in the respective pair of cancer conditions thereby identifying the corresponding subset of the first plurality of feature extraction functions.

In some embodiments, the applying the first feature extraction technique comprises applying a dimension reduction algorithm to the subjects in the first dataset that have either a first cancer condition or a second cancer condition in the respective pair of cancer conditions thereby identifying the corresponding subset of the first plurality of feature extraction functions, and the applying the second feature extraction technique comprises applying the dimension reduction algorithm to the subjects in the second dataset that have either a first cancer condition or a second cancer condition in the respective pair of cancer conditions thereby identifying the corresponding subset of the second plurality of feature extraction functions.

In some embodiments, the cancer condition set comprises three or more cancer conditions and, for each respective cancer condition in the cancer condition set there are two or more subjects in the first plurality of subjects that have the respective cancer condition, and the applying the first feature extraction technique further comprises applying a dimension reduction algorithm to the subjects in the first dataset that have a cancer condition in the three or more cancer conditions thereby identifying the first plurality of feature extraction functions.

In some embodiments, the at least one program further comprises instructions for applying a second feature extraction technique to the respective bin values of respective subjects in the second dataset, thereby identifying a second plurality of feature extraction functions, and applying the respective bin values of respective subjects in the second dataset to the second plurality of feature extraction functions to obtain a respective plurality of second feature values for each corresponding subject in the second dataset. In such embodiments, each feature extraction function in the second plurality of feature extraction functions independently encodes a linear or nonlinear function of bin values of all or a subset of the plurality of bins. Furthermore, the second plurality of feature extraction functions collectively discriminates respective subjects in the second plurality of subjects as having a cancer condition within the cancer condition set based on respective bin values for the respective subjects. Moreover, in such embodiments, the using the transformed second dataset and the indication of the cancer condition of respective subjects in the second plurality of subjects to train a first classifier in the one or more classifier comprises using the plurality of second feature values in the transformed second dataset to train the first classifier. Further still, the applying the second feature extraction technique further comprises applying the dimension reduction algorithm to the subjects in the second dataset that have a cancer condition in the three or more cancer conditions thereby identifying the second plurality of feature extraction functions. In some such embodiments, the dimension reduction algorithm is a linear dimension reduction algorithm or a non-linear dimension reduction algorithm. In some such embodiments, the dimension reduction algorithm is selected from the group consisting of a principal component analysis algorithm, a factor analysis algorithm, Sammon mapping, curvilinear components analysis, a stochastic neighbor embedding (SNE) algorithm, an Isomap algorithm, a maximum variance unfolding algorithm, a locally linear embedding algorithm, a t-SNE algorithm, a non-negative matrix factorization algorithm, a kernel principal component analysis algorithm, a graph-based kernel principal component analysis algorithm, a linear discriminant analysis algorithm, a generalized discriminant analysis algorithm, a uniform manifold approximation and projection (UMAP) algorithm, a LargeVis algorithm, a Laplacian Eigenmap algorithm, and a Fisher's linear discriminant analysis algorithm.

In still other embodiments, the dimension reduction algorithm is a principal component analysis algorithm, and each respective feature extraction function in the corresponding subset of the first plurality of feature extraction functions comprises a respective principal component derived by the dimension reduction algorithm.

In some embodiments, each respective feature extraction function in the corresponding subset of the second plurality of feature extraction functions comprises a respective principal component derived by the dimension reduction algorithm.

In some embodiments, the corresponding subset of the first plurality of feature extraction functions is limited to a threshold number of principal components calculated by the principal component analysis algorithm.

In some embodiments, the corresponding subset of the first plurality of feature extraction functions or the corresponding subset of the second plurality of feature extraction functions is limited to a threshold number of principal components calculated by the principal component analysis algorithm.

In some embodiments, each principal component calculated by the principal component analysis algorithm is assigned an eigenvalue by the principal component algorithm, and the corresponding subset of the first plurality of feature extraction functions is limited to the threshold number of principal components assigned the highest eigenvalues.

In some embodiments, each principal component calculated by the principal component analysis algorithm is assigned an eigenvalue by the principal component algorithm, and the corresponding subset of the first plurality of feature extraction functions or the corresponding subset of the second plurality of feature extraction functions is limited to the threshold number of principal components assigned the highest eigenvalues.

In some embodiments, the at least one program further comprises instructions for pruning the first plurality of feature extraction functions using the first plurality of feature extraction functions and respective indications of the cancer condition of respective subjects in the first plurality of subjects thereby removing a number of feature extraction functions from the first plurality of feature extraction functions.

In some embodiments, the at least one program comprising instructions for pruning the second plurality of feature extraction functions using the second plurality of feature extraction functions and respective indications of the cancer condition of respective subjects in the second plurality of subjects thereby removing a number of feature extraction functions from the second plurality of feature extraction functions.

In some embodiments, the pruning the first plurality of feature extraction functions causes at least a four-fold reduction in the number of feature extraction functions in the first plurality of feature extraction functions.

In some embodiments, the pruning the second plurality of feature extraction functions causes at least a four-fold reduction in the number of feature extraction functions in the second plurality of feature extraction functions.

In some embodiments, the pruning the first plurality of feature extraction functions comprises regressing the first dataset based on all or a subset of the first plurality of feature extraction functions using a regression algorithm to thereby assign a regression coefficient to each respective feature extraction function in the first plurality of feature extraction functions, the regressing leading to classifying a cancer condition in the cancer condition set for each subject in the first plurality of subjects, and removing feature extraction functions from the first plurality of feature extraction functions that are assigned a negative coefficient by the regression algorithm.

In some embodiments, the pruning the second plurality of feature extraction functions comprises regressing the second dataset based on all or a subset of the second plurality of feature extraction functions using a regression algorithm to thereby assign a regression coefficient to each respective feature extraction function in the second plurality of feature extraction functions, the regressing leading to classifying a cancer condition in the cancer condition set for each subject in the second plurality of subjects, and removing feature extraction function from the second plurality of feature extraction functions that are assigned a negative coefficient by the regression algorithm.

In some embodiments, the pruning comprises regressing the first dataset based on all or a subset of the first plurality of feature extraction functions using a regression algorithm to thereby assign a regression coefficient to each respective feature extraction function in the first plurality of feature extraction functions, the regressing leading to classifying a cancer condition in the cancer condition set for each subject in the first plurality of subjects and removing feature extraction functions from the first plurality of feature extraction functions that are assigned a coefficient by the regression algorithm that fails to satisfy a coefficient threshold.

In some embodiments, the pruning comprises regressing the second dataset based on all or a subset of the second plurality of feature extraction functions using a regression algorithm to thereby assign a regression coefficient to each respective feature extraction function in the second plurality of feature extraction functions, the regressing leading to classifying a cancer condition in the cancer condition set for each subject in the second plurality of subjects, and removing feature extraction functions from the second plurality of feature extraction functions that are assigned a coefficient by the regression algorithm that fails to satisfy a coefficient threshold.

In some embodiments, the regression algorithm is logistic regression.

In some embodiments, each feature extraction function in the first plurality of feature extraction functions independently encodes a linear or nonlinear function of bin value of all or a subset of the plurality of bins in the form of an independent weight for each respective bin in the plurality of bins or the subset of the plurality of bins.

In some embodiments, each feature extraction function in the second plurality of feature extraction functions independently encodes a linear or nonlinear function of bin value of all or a subset of the plurality of bins in the form of an independent weight for each respective bin in the plurality of bins or the subset of the plurality of bins.

In some embodiments, the first feature extraction technique is a first convolutional neural network that comprises a first plurality of convolutional layers, each respective convolutional layer in the first plurality of convolutional layers is associated with a learned weight vector that is obtained through back-propagation of the first convolutional neural network using the respective bin values and respective indications of the cancer condition of respective subjects in the first dataset, and the respective learned weight vector of each convolutional layer in a subset of the first plurality of convolutional layers collectively represent the first plurality of feature extraction functions, and the transforming comprises inputting the corresponding second plurality of bin values of a respective subject in the second plurality of subjects into a second convolutional network that comprises the subset of the first plurality of convolutional layers, wherein a weight vector of each respective convolutional layer in the second convolutional neural network is initialized and in some embodiments frozen at values of the learned weight vector of the corresponding convolutional layer in the first convolutional neural network.

In some embodiments, the first plurality of convolutional layers comprises three, four, five, six, seven, eight, nine, ten, between 5 and 50, or between 3 and 100 convolutional layers.

In some embodiments, the first plurality of convolutional layers comprises five convolutional layers and the subset of the first plurality of convolutional layers consists of the first three convolutional layers of the first convolutional neural network.

In some embodiments, the at least one program further comprises instructions for scaling a respective first bin value for each respective bin in the plurality of bins for each respective subject in the first plurality of subjects by taking a log transformation of the respective first bin value thereby forming a log transformed first bin value for the respective bin, subtracting a mean value of the respective log transformed first bin value across the first plurality of subjects from the log transformed first bin value of the respective bin thereby forming a first normalized bin value for the respective bin, and subsequently dividing the respective first normalized bin value for the respective bin by a standard deviation of the first normalized bin value across the first plurality of subjects thereby scaling the first bin value for each respective bin in the plurality of bins for each respective subject in the first plurality of subjects.

In some embodiments, the at least one program further comprises instructions for scaling a respective second bin value for each respective bin in the plurality of bins for each respective subject in the second plurality of subjects by taking a log transformation of the respective second bin value thereby forming a log transformed second bin value for the respective bin, subtracting a mean value of the respective log transformed second bin value across the second plurality of subjects from the log transformed second bin value of the respective bin thereby forming a second normalized bin value for the respective bin, and subsequently dividing the respective second normalized bin value for the respective bin by a standard deviation of the second normalized bin value across the second plurality of subjects thereby scaling the second bin value for each respective bin in the plurality of bins for each respective subject in the second plurality of subjects.

In some embodiments, each respective cancer condition in the cancer condition set is selected from the group consisting of non-cancer, breast cancer, lung cancer, prostate cancer, colorectal cancer, renal cancer, uterine cancer, pancreatic cancer, cancer of the esophagus, a lymphoma, head/neck cancer, ovarian cancer, a hepatobiliary cancer, a melanoma, cervical cancer, multiple myeloma, leukemia, thyroid cancer, bladder cancer, and gastric cancer.

In some embodiments, each cancer condition in the cancer condition set is non-cancer, a predetermined stage of a breast cancer, a predetermined stage of a lung cancer, a predetermined stage of a prostate cancer, a predetermined stage of a colorectal cancer, a predetermined stage of a renal cancer, a predetermined stage of a uterine cancer, a predetermined stage of a pancreatic cancer, a predetermined stage of a cancer of the esophagus, a predetermined stage of a lymphoma, a predetermined stage of a head/neck cancer, a predetermined stage of a ovarian cancer, a predetermined stage of a hepatobiliary cancer, a predetermined stage of a melanoma, a predetermined stage of a cervical cancer, a predetermined stage of a multiple myeloma, a predetermined stage of a leukemia, a predetermined stage of a thyroid cancer, a predetermined stage of a bladder cancer, or a predetermined stage of a gastric cancer.

In some embodiments, a cancer condition in the cancer condition set is a survival metric (e.g., a predetermined likelihood of survival for a predetermined period of time).

In some embodiments, the first tissue type and the second tissue type are each selected from the group consisting of breast, liver, bladder, lung, rectal, thyroid, prostate, uterus, ovarian, esophagus tissue and vasculature.

In some embodiments, the first tissue type or the second tissue type is blood, whole blood, plasma, serum, urine, cerebrospinal fluid, fecal, saliva, sweat, tears, pleural fluid, pericardial fluid, or peritoneal fluid.

In some embodiments, the first tissue type and the second tissue type is the same.

In some embodiments, the first sequencing method or the second sequencing method generates cell-free DNA sequence reads.

In some embodiments, the species is human.

In some embodiments, the corresponding first plurality of bin values of a respective subject in the first plurality of subjects is determined using more than 20,000 sequence reads that are collectively taken from the corresponding biological sample of the respective subject in accordance with the first sequencing method.

In some embodiments, the corresponding first plurality of bin values of a respective subject in the first plurality of subjects is determined using more than 30,000 sequence reads, more than 40,000 sequence reads, more than 50,000 sequence reads or more than 100,000 sequence reads that are collectively taken from the corresponding biological sample of the respective subject in accordance with the first sequencing method.

In some embodiments, an average coverage rate of sequence reads used to form the first plurality of bin values of a respective subject in the first plurality of subjects across the reference genome of the species is at least 10×, at least 20×, or at least 40×.

In some embodiments, each respective sequence read used to form the first plurality of bin values of a respective subject in the first plurality of subjects includes (i) a first portion mappable onto the genome of the species and (ii) a second portion, and the sequence reads used to form the first plurality of bin values of a respective subject in the first plurality of subjects are filtered so that only sequence reads whose first portion is less than 160 nucleotides are used to form the bin values.

In some embodiments, the first nucleic acid sequencing method or the second sequence nucleic acid method is whole genome sequencing, targeted panel sequencing, or whole genome bisulfite sequencing.

In some embodiments, the first classifier is a multivariate classifier.

In some embodiments, the first classifier is a single multivariate classifier that discriminates each cancer condition in the cancer condition set.

In some embodiments, the first classifier is multivariate logistic regression, neural network, or a convolutional neural network.

In some embodiments, the first classifier is a support vector machine, a neural network, a decision tree, clustering, or a regression algorithm.

In some embodiments, the using the transformed second dataset and the indication of the cancer condition of respective subjects in the second plurality of subjects to train a first classifier) is repeated for each unique pair of cancer conditions in the set of cancer conditions thereby training a plurality of classifiers, wherein each respective classifier in the plurality of classifier is trained on subjects in the transformed second dataset that have one of the first cancer condition or the second cancer in the respective pair of cancer conditions represented by the respective classifier.

In some embodiments, the one or more classifiers consist of the first classifier and the first classifier is trained on a cancer condition other than a cancer condition in the cancer condition set.

In some embodiments, the at least one program further comprises instructions for using the first classifier to classify a test subject to a first cancer condition using genotypic information, in electronic form, based on sequence read data in a test biological sample obtained from the test subject as input to the first classifier.

In some embodiments, the test biological sample comprises blood, whole blood, plasma, serum, urine, cerebrospinal fluid, fecal, saliva, sweat, tears, pleural fluid, pericardial fluid, or peritoneal fluid of the test subject.

In some embodiments, the first cancer condition is in the set of cancer conditions.

In some embodiments, the at least one program further comprises instructions for using the one or more classifiers to determine a likelihood that a test subject has each cancer condition in the cancer condition set using genotypic information, in electronic form, based on sequence read data in a test biological sample obtained from the test subject as input to each classifier in the one or more classifiers. In some such embodiments, the test biological sample comprises blood, whole blood, plasma, serum, urine, cerebrospinal fluid, fecal, saliva, sweat, tears, pleural fluid, pericardial fluid, or peritoneal fluid of the test subject.

In some embodiments, the at least one program further comprises instructions for using the first classifier to determine a likelihood that a test subject has each cancer condition in the cancer condition set using genotypic information, in electronic form, based on sequence read data in a test biological sample obtained from the test subject as input to the first classifier.

In some embodiments, the test biological sample comprises blood, whole blood, plasma, serum, urine, cerebrospinal fluid, fecal, saliva, sweat, tears, pleural fluid, pericardial fluid, or peritoneal fluid of the test subject.

In some embodiments, the corresponding first plurality of sequence reads comprises more than 10,000 sequence reads, the first plurality of subjects comprises twenty-five or more subjects, and the plurality of bins comprises twenty or more bins.

In some embodiments, the first plurality of feature extraction functions comprises four or more feature extraction functions.

In some embodiments, the corresponding second plurality of sequence reads comprises more than 10,000 sequence reads.

In some embodiments, the first nucleic acid sequencing method is methylation sequencing and wherein each bin value in the corresponding first plurality of bin values is a number of fragments represented by the corresponding first plurality of sequence reads.

In some embodiments, the corresponding first plurality of bin values is a number of fragments represented by the corresponding first plurality of sequence reads after application of one or more filter conditions.

In some embodiments, the methylation sequencing produces a corresponding methylation pattern for each respective fragment in the number of fragments, and a filter condition in the one or more filter conditions is application of a p-value threshold to the corresponding methylation pattern, wherein the p-value threshold is representative of how frequently a methylation pattern is observed in a cohort of non-cancer subjects. In some such embodiments, the p-value threshold is between 0.001 and 0.20.

In some embodiments, the methylation sequencing produces a corresponding methylation pattern for each respective fragment in the number of fragments, and a filter condition in the one or more filter conditions is application of a requirement that the respective fragment is represented by a threshold number of sequence reads in the corresponding first plurality of sequence reads. In some such embodiments, the threshold number is 2, 3, 4, 5, 6, 7, 8, 9, 10, or an integer between 10 and 100.

In some embodiments, the methylation sequencing produces a corresponding methylation pattern for each respective fragment in the number of fragments, and a filter condition in the one or more filter conditions is application of a requirement that the respective fragment have a threshold number of CpG sites (e.g., at least 1, 2, 3, 4, 5, 6, 7, 8, 9 or 10 CpG sites).

In some embodiments, the methylation sequencing produces a corresponding methylation pattern for each respective fragment in the number of fragments, and a filter condition in the one or more filter conditions is a requirement that the respective fragment have a length of less than a threshold number of base pairs (e.g., 1 thousand, 2 thousand, 3 thousand, or 4 thousand contiguous base pairs in length).

Another aspect of the present disclosure provides a method for training one or more classifiers to discriminate between each cancer condition in a cancer condition set, the cancer condition set comprising two or more cancer conditions. The method comprises providing a first plurality of feature extraction functions based on a first dataset. The first dataset comprises, for each respective subject in a first plurality of subjects of a species, corresponding first genotypic information comprising (i) a corresponding first plurality of bin values, each respective bin value in the corresponding first plurality of bin values for a corresponding bin in a plurality of bins and (ii) an indication of a cancer condition of the respective subject in the cancer condition set. Each bin in the plurality of bins represents a portion of a reference genome of the species. The corresponding first plurality of bin values of each respective subject in the first plurality of subjects is obtained from a corresponding biological sample of the respective subject, which comprises a first tissue type, using a corresponding first plurality of sequence reads determined by a first nucleic acid sequencing method. The first plurality of feature extraction functions is obtained by applying a first feature extraction technique to the respective bin values of respective subjects in the first dataset, thereby identifying the first plurality of feature extraction functions. Each feature extraction function in the first plurality of feature extraction functions independently encodes a linear or nonlinear function of bin values of all or a subset of the plurality of bins. The first plurality of feature extraction functions collectively discriminates respective subjects in the first plurality of subjects as having a cancer condition within the cancer condition set based on respective bin values for the respective subjects.

The method further comprises obtaining a second dataset comprising, for each respective subject in a second plurality of subjects of the species, corresponding second genotypic information comprising (i) a corresponding second plurality of bin values, each respective bin value in the corresponding second plurality of bin values representing a corresponding bin in the plurality of bins and (ii) an indication of a cancer condition of the respective subject in the cancer condition set. The corresponding second plurality of bin values of each respective subject in the second plurality of subjects is obtained from a corresponding biological sample of the respective subject, which comprises a second tissue type, using a corresponding second plurality of sequence reads determined by a second nucleic acid sequencing method. At least the first nucleic acid sequencing method differs from the second nucleic acid sequencing method or the first tissue type differs from the second tissue type The method further comprises transforming, based on at least each respective feature extraction function in the first plurality of feature extraction functions, the respective second plurality of bin values of each corresponding subject in the second plurality of subjects against the respective feature extraction function, thereby contributing to a transformed second dataset a respective plurality of feature values for each corresponding subject The method further comprises using the transformed second dataset and the indication of the cancer condition of respective subjects in the second plurality of subjects to train a first classifier in the one or more classifiers on at least a pair of cancer conditions in the cancer condition set.

Another aspect of the present disclosure provides a non-transitory computer-readable storage medium having stored thereon program code instructions that, when executed by a processor, cause the processor to perform a method for training one or more classifiers to discriminate between each cancer condition in a cancer condition set, the cancer condition set comprising two or more cancer conditions. The method comprises providing a first plurality of feature extraction functions based on a first dataset. The first dataset comprises, for each respective subject in a first plurality of subjects of a species, corresponding first genotypic information comprising (i) a corresponding first plurality of bin values, each respective bin value in the corresponding first plurality of bin values for a corresponding bin in a plurality of bins and (ii) an indication of a cancer condition of the respective subject in the cancer condition set. Each bin in the plurality of bins represents a portion of a reference genome of the species. The corresponding first plurality of bin values of each respective subject in the first plurality of subjects is obtained from a corresponding biological sample of the respective subject, which comprises a first tissue type, using a corresponding first plurality of sequence reads determined by a first nucleic acid sequencing method. The first plurality of feature extraction functions is obtained by applying a first feature extraction technique to the respective bin values of respective subjects in the first dataset, thereby identifying the first plurality of feature extraction functions. Each feature extraction function in the first plurality of feature extraction functions independently encodes a linear or non-linear function of bin values of all or a subset of the plurality of bins. The first plurality of feature extraction functions collectively discriminates respective subjects in the first plurality of subjects as having a cancer condition within the cancer condition set based on respective bin values for the respective subjects.

The method further comprises obtaining a second dataset comprising, for each respective subject in a second plurality of subjects of the species, corresponding second genotypic information comprising (i) a corresponding second plurality of bin values, each respective bin value in the corresponding second plurality of bin values representing a corresponding bin in the plurality of bins and (ii) an indication of a cancer condition of the respective subject in the cancer condition set. The corresponding second plurality of bin values of each respective subject in the second plurality of subjects is obtained from a corresponding biological sample of the respective subject, which comprises a second tissue type, using a corresponding second plurality of sequence reads determined by a second nucleic acid sequencing method. At least the first nucleic acid sequencing method differs from the second nucleic acid sequencing method or the first tissue type differs from the second tissue type.

The method further comprises transforming, based on at least each respective feature extraction function in the first plurality of feature extraction functions, the respective second plurality of bin values of each corresponding subject in the second plurality of subjects against the respective feature extraction function, thereby contributing to a transformed second dataset a respective plurality of feature values for each corresponding subject.

The method further comprises using the transformed second dataset and the indication of the cancer condition of respective subjects in the second plurality of subjects to train a first classifier in the one or more classifiers on at least a pair of cancer conditions in the cancer condition set.

Another aspect of the present disclosure is a computer system for training one or more classifiers to discriminate between each cancer condition in a cancer condition set, the cancer condition set comprising two or more cancer conditions. The computer system comprises at least one processor and a memory storing at least one program for execution by the at least one processor. The at least one program comprise instructions for providing a first plurality of feature extraction functions based on a first dataset, where the first dataset comprises, for each respective subject in a first plurality of subjects of a species, corresponding first genotypic information comprising (i) a corresponding first plurality of bin values, each respective bin value in the corresponding first plurality of bin values for a corresponding bin in a plurality of bins and (ii) an indication of a cancer condition of the respective subject in the cancer condition set. Each bin in the plurality of bins represents a portion of a reference genome of the species. The corresponding first plurality of bin values of each respective subject in the first plurality of subjects is obtained from a corresponding biological sample of the respective subject, which comprises a first tissue type, using a corresponding first plurality of sequence reads determined by a first nucleic acid sequencing method. The first plurality of feature extraction functions is obtained by applying a first feature extraction technique to the respective bin values of respective subjects in the first dataset, thereby identifying the first plurality of feature extraction functions. Each feature extraction function in the first plurality of feature extraction functions independently encodes a linear or non-linear function of bin values of all or a subset of the plurality of bins. The first plurality of feature extraction functions collectively discriminates respective subjects in the first plurality of subjects as having a cancer condition within the cancer condition set based on respective bin values for the respective subjects.

The at least one program comprise instructions for obtaining a second dataset comprising, for each respective subject in a second plurality of subjects of the species, corresponding second genotypic information comprising (i) a corresponding second plurality of bin values, each respective bin value in the corresponding second plurality of bin values representing a corresponding bin in the plurality of bins and (ii) an indication of a cancer condition of the respective subject in the cancer condition set. The corresponding second plurality of bin values of each respective subject in the second plurality of subjects is obtained from a corresponding biological sample of the respective subject, which comprises a second tissue type, using a corresponding second plurality of sequence reads determined by a second nucleic acid sequencing method. At least the first nucleic acid sequencing method or the second nucleic acid sequencing method is methylation sequencing The at least one program comprise instructions for transforming, based on at least each respective feature extraction function in the first plurality of feature extraction functions, the respective second plurality of bin values of each corresponding subject in the second plurality of subjects against the respective feature extraction function, thereby contributing to a transformed second dataset a respective plurality of feature values for each corresponding subject.

The at least one program comprise instructions for using the transformed second dataset and the indication of the cancer condition of respective subjects in the second plurality of subjects to train a first classifier in the one or more classifiers on at least a pair of cancer conditions in the cancer condition set.

In some embodiments, the first or second nucleic acid sequencing method is targeted or whole genome sequencing.

In some embodiments, the first nucleic acid sequencing method is targeted sequencing using a plurality of nucleic acid probes, and the second nucleic acid sequencing method is whole genome sequencing.

In some embodiments, the first nucleic acid sequencing method is whole genome sequencing, and the second nucleic acid sequence method is targeted sequencing using a plurality of nucleic acid probes.

In some embodiments, the first nucleic acid sequencing method is methylation sequencing and wherein each bin value in the corresponding first plurality of bin values is a number of fragments represented by the corresponding first plurality of sequence reads.

In some embodiments, the corresponding first plurality of bin values is a number of fragments represented by the corresponding first plurality of sequence reads after application of one or more filter conditions.

In some embodiments, the methylation sequencing produces a corresponding methylation pattern for each respective fragment in the number of fragments, and a filter condition in the one or more filter conditions is application of a p-value threshold (e.g., between 0.001 and 0.20) to the corresponding methylation pattern. In such embodiments, the p-value threshold is representative of how frequently a methylation pattern is observed in a cohort of non-cancer subjects.

In some embodiments, the methylation sequencing produces a corresponding methylation pattern for each respective fragment in the number of fragments, and a filter condition in the one or more filter conditions is application of a requirement that the respective fragment is represented by a threshold number (e.g., 2, 3, 4, 5, 6, 7, 8, 9, 10, or an integer between 10 and 100) of sequence reads in the corresponding first plurality of sequence reads.

In some embodiments, the methylation sequencing produces a corresponding methylation pattern for each respective fragment in the number of fragments, and a filter condition in the one or more filter conditions is application of a requirement that the respective fragment have a threshold number of CpG sites (e.g., at least 1, 2, 3, 4, 5, 6, 7, 8, 9 or 10 CpG sites.).

In some embodiments, the methylation sequencing produces a corresponding methylation pattern for each respective fragment in the number of fragments, and a filter condition in the one or more filter conditions is a requirement that the respective fragment have a length of less than a threshold number of base pairs (e.g., 1 thousand, 2 thousand, 3 thousand, or 4 thousand contiguous base pairs in length).

Another aspect of the present disclosure provides a method for training one or more classifiers to discriminate between each cancer condition in a cancer condition set, the cancer condition set comprising two or more cancer conditions. The method comprises providing a first plurality of feature extraction functions based on a first dataset. The first dataset comprises, for each respective subject in a first plurality of subjects of a species, corresponding first genotypic information comprising (i) a corresponding first plurality of bin values, each respective bin value in the corresponding first plurality of bin values for a corresponding bin in a plurality of bins and (ii) an indication of a cancer condition of the respective subject in the cancer condition set. Each bin in the plurality of bins represents a portion of a reference genome of the species. The corresponding first plurality of bin values of each respective subject in the first plurality of subjects is obtained from a corresponding biological sample of the respective subject, which comprises a first tissue type, using a corresponding first plurality of sequence reads determined by a first nucleic acid sequencing method. The first plurality of feature extraction functions is obtained by applying a first feature extraction technique to the respective bin values of respective subjects in the first dataset, thereby identifying the first plurality of feature extraction functions. Each feature extraction function in the first plurality of feature extraction functions independently encodes a linear or nonlinear function of bin values of all or a subset of the plurality of bins. The first plurality of feature extraction functions collectively discriminates respective subjects in the first plurality of subjects as having a cancer condition within the cancer condition set based on respective bin values for the respective subjects.

The method further comprises obtaining a second dataset comprising, for each respective subject in a second plurality of subjects of the species, corresponding second genotypic information comprising (i) a corresponding second plurality of bin values, each respective bin value in the corresponding second plurality of bin values representing a corresponding bin in the plurality of bins and (ii) an indication of a cancer condition of the respective subject in the cancer condition set. The corresponding second plurality of bin values of each respective subject in the second plurality of subjects is obtained from a corresponding biological sample of the respective subject, which comprises a second tissue type, using a corresponding second plurality of sequence reads determined by a second nucleic acid sequencing method. At least the first nucleic acid sequencing method or the second nucleic acid sequencing method is methylation sequencing.

The method further comprises transforming, based on at least each respective feature extraction function in the first plurality of feature extraction functions, the respective second plurality of bin values of each corresponding subject in the second plurality of subjects against the respective feature extraction function, thereby contributing to a transformed second dataset a respective plurality of feature values for each corresponding subject.

The method further comprises using the transformed second dataset and the indication of the cancer condition of respective subjects in the second plurality of subjects to train a first classifier in the one or more classifiers on at least a pair of cancer conditions in the cancer condition set.

Another aspect of the present disclosure provides a non-transitory computer-readable storage medium having stored thereon program code instructions that, when executed by a processor, cause the processor to perform a method for training one or more classifiers to discriminate between each cancer condition in a cancer condition set, the cancer condition set comprising two or more cancer conditions. The method comprises providing a first plurality of feature extraction functions based on a first dataset. The first dataset comprises, for each respective subject in a first plurality of subjects of a species, corresponding first genotypic information comprising (i) a corresponding first plurality of bin values, each respective bin value in the corresponding first plurality of bin values for a corresponding bin in a plurality of bins and (ii) an indication of a cancer condition of the respective subject in the cancer condition set. Each bin in the plurality of bins represents a portion of a reference genome of the species. The corresponding first plurality of bin values of each respective subject in the first plurality of subjects is obtained from a corresponding biological sample of the respective subject, which comprises a first tissue type, using a corresponding first plurality of sequence reads determined by a first nucleic acid sequencing method. The first plurality of feature extraction functions is obtained by applying a first feature extraction technique to the respective bin values of respective subjects in the first dataset, thereby identifying the first plurality of feature extraction functions. Each feature extraction function in the first plurality of feature extraction functions independently encodes a linear or non-linear function of bin values of all or a subset of the plurality of bins. The first plurality of feature extraction functions collectively discriminates respective subjects in the first plurality of subjects as having a cancer condition within the cancer condition set based on respective bin values for the respective subjects.

The method further comprises (B) obtaining a second dataset comprising, for each respective subject in a second plurality of subjects of the species, corresponding second genotypic information comprising (i) a corresponding second plurality of bin values, each respective bin value in the corresponding second plurality of bin values representing a corresponding bin in the plurality of bins and (ii) an indication of a cancer condition of the respective subject in the cancer condition set. The corresponding second plurality of bin values of each respective subject in the second plurality of subjects is obtained from a corresponding biological sample of the respective subject, which comprises a second tissue type, using a corresponding second plurality of sequence reads determined by a second nucleic acid sequencing method. At least the first nucleic acid sequencing method or the second nucleic acid sequencing method is methylation sequencing.

The method further comprises transforming, based on at least each respective feature extraction function in the first plurality of feature extraction functions, the respective second plurality of bin values of each corresponding subject in the second plurality of subjects against the respective feature extraction function, thereby contributing to a transformed second dataset a respective plurality of feature values for each corresponding subject.

The method further comprises using the transformed second dataset and the indication of the cancer condition of respective subjects in the second plurality of subjects to train a first classifier in the one or more classifiers on at least a pair of cancer conditions in the cancer condition set.

Another aspect of the present disclosure provides a computer system for classifying a test subject to a first cancer condition in a cancer condition set, the cancer condition set comprising two or more cancer conditions. The computer system comprises at least one processor and a memory storing at least one program for execution by the at least one processor. The at least one program comprises instructions for obtaining test genotypic information comprising a corresponding test plurality of bin values, each respective bin value in the test plurality of bin values for a corresponding bin in a plurality of bins. Each bin in the plurality of bins represents a portion of a reference genome of the species. The test plurality of bin values is obtained from a test biological sample of the test subject, using a corresponding test plurality of sequence reads determined by a first nucleic acid sequencing method. The test plurality of sequence reads comprises at least 10,000 sequence reads. The plurality of bins comprises at least 100 bins. The at least one program comprises instructions for applying the test plurality of bin values to a classifier, trained on a transformed second dataset obtained by transfer learning between a first dataset and a second dataset, to cause the classifier to classify the test subject to the first cancer condition in the cancer condition set. The first dataset comprises, for each respective subject in a first plurality of training subjects, the first plurality of training subjects comprising at least fifty subjects, corresponding first genotypic information comprising (i) a corresponding first plurality of bin values, each respective bin value in the corresponding first plurality of bin values for a corresponding bin in the plurality of bins and (ii) an indication of a cancer condition of the respective subject in the cancer condition set. The corresponding first plurality of bin values of each respective subject in the first plurality of subjects is obtained from a corresponding biological sample of the respective subject, which comprises a first tissue type, using a corresponding first plurality of sequence reads determined by a second nucleic acid sequencing method. The second dataset comprises, for each respective subject in a second plurality of subjects of the species, corresponding second genotypic information comprising (i) a corresponding second plurality of bin values, each respective bin value in the corresponding second plurality of bin values representing a corresponding bin in the plurality of bins and (ii) an indication of a cancer condition of the respective subject in the cancer condition set. The corresponding second plurality of bin values of each respective subject in the second plurality of subjects is obtained from a corresponding biological sample of the respective subject, which comprises a second tissue type, using a corresponding second plurality of sequence reads determined by a third nucleic acid sequencing method. In such embodiments, at least the second nucleic acid sequencing method differs from the third nucleic acid sequencing method or the first tissue type differs from the second tissue type.

In such embodiments, a plurality of feature extraction functions is obtained by applying a feature extraction technique to the respective bin values of respective subjects in the first dataset, thereby identifying a plurality of feature extraction functions. Each feature extraction function in the plurality of feature extraction functions independently encodes a linear or nonlinear function of bin values of all or a subset of the plurality of bins, and the plurality of feature extraction functions collectively discriminates respective subjects in the first plurality of subjects as having a cancer condition within the cancer condition set based on respective bin values for the respective subjects.

Further, in such embodiments, each respective feature extraction function in the plurality of feature extraction functions is applied against the respective second plurality of bin values of each corresponding subject in the second plurality of subjects, thereby contributing to the transformed second dataset a respective plurality of feature values for each corresponding subject. In some embodiments, the test plurality of bin values is a number of fragments represented by the test plurality of sequence reads after application of one or more filter conditions. In some embodiments, the first nucleic acid sequencing method produces a corresponding methylation pattern for each respective fragment in the number of fragments, and a filter condition in the one or more filter conditions is application of a p-value threshold (e.g., selected from the range of between 0.001 and 0.20) to the corresponding methylation pattern, wherein the p-value threshold is representative of how frequently a methylation pattern is observed in a cohort of non-cancer subjects.

In some embodiments, the first nucleic acid sequencing method produces a corresponding methylation pattern for each respective fragment in the number of fragments, and a filter condition in the one or more filter conditions is application of a requirement that the respective fragment is represented by a threshold number (e.g., 2, 3, 4, 5, 6, 7, 8, 9, 10, or an integer between 10 and 100) of sequence reads in the test plurality of sequence reads.

In some embodiments, the first nucleic acid sequencing method produces a corresponding methylation pattern for each respective fragment in the number of fragments, and a filter condition in the one or more filter conditions is application of a requirement that the respective fragment have a threshold number of CpG sites (at least 1, 2, 3, 4, 5, 6, 7, 8, 9 or 10 CpG sites).

In some embodiments, the first nucleic acid sequencing method produces a corresponding methylation pattern for each respective fragment in the number of fragments, and a filter condition in the one or more filter conditions is a requirement that the respective fragment have a length of less than a threshold number of base pairs (e.g., 1 thousand, 2 thousand, 3 thousand, or 4 thousand contiguous base pairs in length).

INCORPORATION BY REFERENCE

All publications, patents, and patent applications herein are incorporated by reference in their entireties. In the event of a conflict between a term herein and a term in an incorporated reference, the term herein controls.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the several views of the drawings.

FIG. 3 illustrates an example of data structures representing a first dataset and a second dataset, in accordance with some embodiments of the present disclosure.

FIGS. 10A, 10B, 10C, 10D, 10E, 10F, 10G, and 10H are flowcharts illustrating examples of methods of training a classifier to discriminate between a cancer condition in a cancer condition set, in accordance with some embodiments of the present disclosure.

FIG. 12 illustrates results of detection of various types of cancers using a CCGA+TCGA classifier versus a WGS CCGA classifier across a test dataset drawn from the CCGA study of Example 2, in accordance with some embodiments of the present disclosure.

FIG. 21 illustrates generation of a data structure for a control group, in accordance with an aspect of the present disclosure.

DETAILED DESCRIPTION

Figure 1:
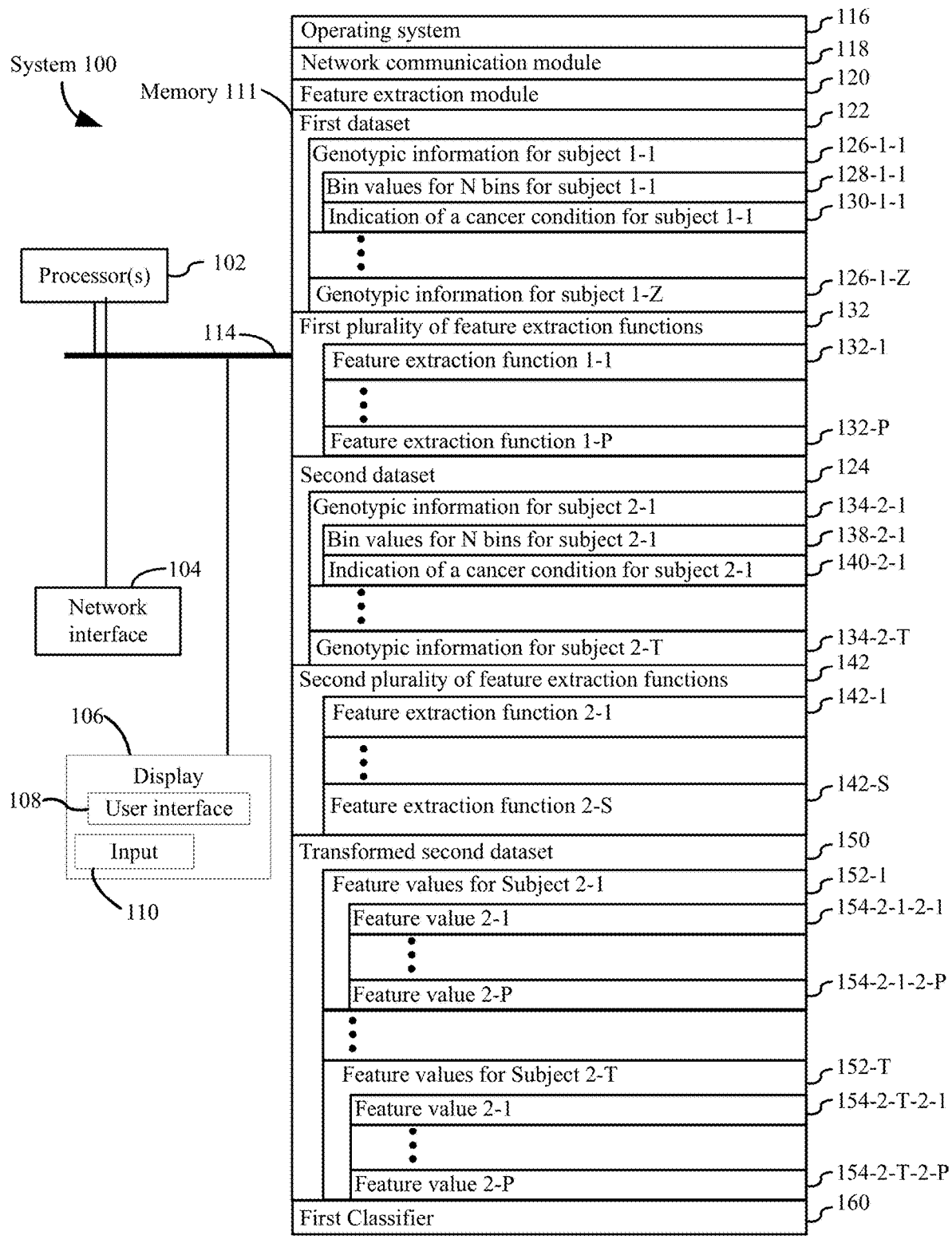
FIG. 1 is a block diagram illustrating an example of a computing system in accordance with some embodiments of the present disclosure.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

The implementations described herein provide various technical solutions for training a classifier to discriminate between cancer conditions in a cancer condition set. The described techniques use a transfer learning approach where feature extraction functions are learned from one dataset and are applied to a new dataset to derive values. The values characterize the data in the new dataset and can be used as a basis to train a classifier that assigns labels to subjects from which the new dataset is obtained. Examples of the values include an indication that data from a biological sample is indicative of cancer or an indication that data from a biological sample is not indicative of cancer (e.g., "non-cancer").

Definitions

As used herein, the term "abnormal methylation pattern" or "anomalous methylation pattern" refers to a methylation state vector or a methylation status of a DNA molecule having the methylation state vector that is expected to be found in a sample less frequently than a threshold value. In a particular embodiment provided herein, the expectedness of finding a specific methylation state vector in a healthy control group comprising healthy individuals is represented by a p-value. A low p-value score, thereby, generally corresponds to a methylation state vector which is relatively unexpected in comparison to other methylation state vectors within samples from healthy individuals in the healthy control group. A high p-value score generally corresponds to a methylation state vector which is relatively more expected in comparison to other methylation state vectors found in samples from healthy individuals in the healthy control group. A methylation state vector having a p-value lower than a threshold value (e.g., 0.1, 0.01, 0.001, 0.0001, etc.) can be defined as an abnormal methylation pattern. Various methods known in the art can be used to calculate a p-value or expectedness of a methylation pattern or a methylation state vector. Exemplary methods provided herein involve use of a Markov chain probability that assumes methylation statuses of CpG sites to be dependent on methylation statuses of neighboring CpG sites. Alternate methods provided herein calculate the expectedness of observing a specific methylation state vector in healthy individuals by utilizing a mixture-model including multiple mixture components, each being an independent-sites model where methylation at each CpG site is assumed to be independent of methylation statuses at other CpG sites. Methods provided herein use genomic regions having an anomalous methylation pattern. A genomic region can be determined to have an anomalous methylation pattern when cfDNA fragments corresponding to or originated from the genomic region have methylation state vectors that appear less frequently than a threshold value in reference samples. The reference samples can be samples from control subjects or healthy subjects. The frequency for a methylation state vector to appear in the reference samples can be represented as a p-value score. When cfDNA fragments corresponding to or originated from the genomic region do not have a single, uniform methylation state vector, the genomic region can have multiple p-value scores for multiple methylation state vectors. In this case, the multiple pvalues cores can be summed or averaged before being compared to the threshold value. Various methods known in the art can be adopted to compare p-value scores corresponding to the genomic region and the threshold value, including but not limited to arithmetic mean, geometric mean, harmonic mean, median, mode, etc.

As used herein, the term "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the art. "About" can mean a range of ±20%, ±10%, ±5%, or ±1% of a given value. The term "about" or "approximately" can mean within an order of magnitude, within 5-fold, or within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to ±5%.

As used herein, the term "biological sample," "patient sample," or "sample" refers to any sample taken from a subject, which can reflect a biological state associated with the subject, and that includes cell free DNA. Examples of biological samples include, but are not limited to, blood, whole blood, plasma, serum, urine, cerebrospinal fluid, fecal, saliva, sweat, tears, pleural fluid, pericardial fluid, or peritoneal fluid of the subject. A biological sample can include any tissue or material derived from a living or dead subject. A biological sample can be a cell-free sample. A biological sample can comprise a nucleic acid (e.g., DNA or RNA) or a fragment thereof. The term "nucleic acid" can refer to deoxyribonucleic acid (DNA), ribonucleic acid (RNA) or any hybrid or fragment thereof. The nucleic acid in the sample can be a cell-free nucleic acid. A sample can be a liquid sample or a solid sample (e.g., a cell or tissue sample). A biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. A biological sample can be a stool sample. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). A biological sample can be treated to physically disrupt tissue or cell structure (e.g., centrifugation and/or cell lysis), thus releasing intracellular components into a solution which can further contain enzymes, buffers, salts, detergents, and the like which can be used to prepare the sample for analysis.

As used herein, the term "cancer" or "tumor" refers to an abnormal mass of tissue in which the growth of the mass surpasses and is not coordinated with the growth of normal tissue. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites.

As used herein, the term "cancer condition" refers to breast cancer, lung cancer, prostate cancer, colorectal cancer, renal cancer, uterine cancer, pancreatic cancer, cancer of the esophagus, a lymphoma, head/neck cancer, ovarian cancer, a hepatobiliary cancer, a melanoma, cervical cancer, multiple myeloma, leukemia, thyroid cancer, bladder cancer, and gastric cancer. The term "cancer condition" also refers to a "non-cancer" condition of not having cancer or non-cancerous condition. A cancer condition can be a predetermined stage of a breast cancer, a predetermined stage of a lung cancer, a predetermined stage of a prostate cancer, a predetermined stage of a colorectal cancer, a predetermined stage of a renal cancer, a predetermined stage of a uterine cancer, a predetermined stage of a pancreatic cancer, a predetermined stage of a cancer of the esophagus, a predetermined stage of a lymphoma, a predetermined stage of a head/neck cancer, a predetermined stage of a ovarian cancer, a predetermined stage of a hepatobiliary cancer, a predetermined stage of a melanoma, a predetermined stage of a cervical cancer, a predetermined stage of a multiple myeloma, a predetermined stage of a leukemia, a predetermined stage of a thyroid cancer, a predetermined stage of a bladder cancer, or a predetermined stage of a gastric cancer. A cancer condition can also be a survival metric, which can be a predetermined likelihood of survival for a predetermined period of time. For example, the survival metric can be defined as the difference in time (e.g., years or months) between the date of the initial diagnosis of a disease or condition (e.g., cancer) until the date of expiry of the patient due to that disease or condition.

The term "classification" can refer to any number(s) or other characters(s) that are associated with a particular property of a sample. For example, a "+" symbol (or the word "positive") can signify that a sample is classified as having deletions or amplifications. In another example, the term "classification" can refer to an amount of tumor tissue in the subject and/or sample, a size of the tumor in the subject and/or sample, a stage of the tumor in the subject, a tumor load in the subject and/or sample, and presence of tumor metastasis in the subject. The classification can be binary (e.g., positive or negative) or have more levels of classification (e.g., a scale from 1 to 10 or 0 to 1). The terms "cutoff" and "threshold" can refer to predetermined numbers used in an operation. For example, a cutoff size can refer to a size above which fragments are excluded. A threshold value can be a value above or below which a particular classification applies. Either of these terms can be used in either of these contexts.

As used herein, the terms "cell free nucleic acid," "cell free DNA," and "cfDNA" interchangeably refer to nucleic acid fragments that circulate in a subject's body (e.g., bloodstream) and originate from one or more healthy cells and/or from one or more cancer cells.

As used herein, the term "cell-free nucleic acids" refers to nucleic acid molecules that can be found outside cells, in bodily fluids such as blood, whole blood, plasma, serum, urine, cerebrospinal fluid, fecal, saliva, sweat, sweat, tears, pleural fluid, pericardial fluid, or peritoneal fluid of a subject. Cell-free nucleic acids are used interchangeably as circulating nucleic acids. Examples of the cell-free nucleic acids include but are not limited to RNA, mitochondrial DNA, or genomic DNA.

As used herein, the terms "control," "control sample," "reference," "reference sample," "normal," and "normal sample" describe a sample from a subject that does not have a particular condition, or is otherwise healthy. In an example, a method as disclosed herein can be performed on a subject having a tumor, where the reference sample is a sample taken from a healthy tissue of the subject. A reference sample can be obtained from the subject, or from a database. The reference can be, e.g., a reference genome that is used to map sequence reads obtained from sequencing a sample from the subject. A reference genome can refer to a haploid or diploid genome to which sequence reads from the biological sample and a constitutional sample can be aligned and compared. An example of constitutional sample can be DNA of white blood cells obtained from the subject. For a haploid genome, there can be only one nucleotide at each locus. For a diploid genome, heterozygous loci can be identified; each heterozygous locus can have two alleles, where either allele can allow a match for alignment to the locus.

As used herein, the term "CpG site" refers to a region of a DNA molecule where a cytosine nucleotide is followed by a guanine nucleotide in the sequence of bases along its 5' to 3' direction. "CpG" is a shorthand for 5'-C-phosphate-G-3' that is cytosine and guanine separated by only one phosphate group; phosphate links any two nucleotides together in DNA. Cytosines in CpG dinucleotides can be methylated to form 5-methylcytosine.

As used herein, the term "false positive" (FP) refers to a subject that does not have a condition. False positive can refer to a subject that does not have a tumor, a cancer, a precancerous condition (e.g., a precancerous lesion), a localized or a metastasized cancer, a non-malignant disease, or is otherwise healthy. The term false positive can refer to a subject that does not have a condition, but is identified as having the condition by an assay or method of the present disclosure.

As used herein, the term "false negative" (FN) refers to a subject that has a condition. False negative can refer to a subject that has a tumor, a cancer, a precancerous condition (e.g., a precancerous lesion), a localized or a metastasized cancer, or a non-malignant disease. The term false negative can refer to a subject that has a condition, but is identified as not having the condition by an assay or method of the present disclosure.

As used herein, the phrase "healthy" refers to a subject possessing good health. A healthy subject can demonstrate an absence of any malignant or non-malignant disease. A "healthy individual" can have other diseases or conditions, unrelated to the condition being assayed, which can normally not be considered "healthy."

As used herein, the term "hypomethylated" or "hypermethylated" refers to a methylation status of a DNA molecule containing multiple CpG sites (e.g., more than 3, 4, 5, 6, 7, 8, 9, 10, etc.) where a high percentage of the CpG sites (e.g., more than 80%, 85%, 90%, or 95%, or any other percentage within the range of 50%-100%) are unmethylated or methylated, respectively.

As used herein, the term "level of cancer" refers to whether cancer exists (e.g., presence or absence), a stage of a cancer, a size of tumor, presence or absence of metastasis, an estimated tumor fraction concentration, a total tumor mutational burden value, the total tumor burden of the body, and/or other measure of a severity of a cancer (e.g., recurrence of cancer). The level of cancer can be a number or other indicia, such as symbols, alphabet letters, and colors. The level can be zero. The level of cancer can also include premalignant or precancerous conditions (states) associated with mutations or a number of mutations. The level of cancer can be used in various ways. For example, screening can check if cancer is present in someone who is not known previously to have cancer. Assessment can investigate someone who has been diagnosed with cancer to monitor the progress of cancer over time, study the effectiveness of therapies or to determine the prognosis. In one embodiment, the prognosis can be expressed as the chance of a subject dying of cancer, or the chance of the cancer progressing after a specific duration or time, or the chance of cancer metastasizing. Detection can comprise 'screening' or can comprise checking if someone, with suggestive features of cancer (e.g., symptoms or other positive tests), has cancer. A "level of pathology" can refer to level of pathology associated with a pathogen, where the level can be as described above for cancer. When the cancer is associated with a pathogen, a level of cancer can be a type of a level of pathology.

As used herein, the term "methylation state vector" or "methylation status vector" refers to a vector comprising multiple elements, where each element indicates methylation status of a methylation site in a DNA molecule comprising multiple methylation sites, in the order they appear from 5' to 3' in the DNA molecule. For example, <Mx, Mx+J, Mx+2>, <Mx, Mx+1, Ux+2>, . . . , <Ux, Ux+1, Ux+2> can be methylation vectors for DNA molecules comprising three methylation sites, where M represents a methylated methylation site and U represents an unmethylated methylation site.

As used herein a "methylome" can be a measure of the amount or extent of DNA methylation at a plurality of sites or loci in a genome. The methylome can correspond to all of a genome, a substantial part of a genome, or relatively small portion(s) of a genome. A "tumor methylome" can be a methylome of a tumor of a subject (e.g., a human). A tumor methylome can be determined using tumor tissue or cell-free tumor DNA in plasma. A tumor methylome can be one example of a methylome of interest. A methylome of interest can be a methylome of an organ that can contribute nucleic acid, e.g., DNA into a bodily fluid (e.g., a methylome of brain cells, a bone, lungs, heart, muscles, kidneys, etc.). The organ can be a transplanted organ.

As used herein the term "methylation index" for each genomic site (e.g., a CpG site) can refer to the proportion of sequence reads showing methylation at the site over the total number of reads covering that site. The "methylation density" of a region can be the number of reads at sites within a region showing methylation divided by the total number of reads covering the sites in the region. The sites can have specific characteristics, (e.g., the sites can be CpG sites). The "CpG methylation density" of a region can be the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of unconverted cytosines (which can correspond to methylated cytosine) at CpG sites as a proportion of all CpG sites covered by sequence reads mapped to the 100-kb region. This analysis can also be performed for other bin sizes, e.g., 50-kb or 1-Mb, etc. A region can be an entire genome or a chromosome or part of a chromosome (e.g., a chromosomal arm). A methylation index of a CpG site can be the same as the methylation density for a region when the region only includes that CpG site. The "proportion of methylated cytosines" can refer the number of cytosine sites, "C's," that are shown to be methylated (for example unconverted after bisulfite conversion) over the total number of analyzed cytosine residues, e.g., including cytosines outside of the CpG context, in the region. The methylation index, methylation density and proportion of methylated cytosines are examples of "methylation levels."

As used herein, the term "methylation profile" (also called methylation status) can include information related to DNA methylation for a region. Information related to DNA methylation can include a methylation index of a CpG site, a methylation density of CpG sites in a region, a distribution of CpG sites over a contiguous region, a pattern or level of methylation for each individual CpG site within a region that contains more than one CpG site, and non-CpG methylation. A methylation profile of a substantial part of the genome can be considered equivalent to the methylome. "DNA methylation" in mammalian genomes can refer to the addition of a methyl group to position 5 of the heterocyclic ring of cytosine (e.g., to produce 5-methylcytosine) among CpG dinucleotides. Methylation of cytosine can occur in cytosines in other sequence contexts, for example 5'-CHG-3' and 5'-CHH-3', where H is adenine, cytosine or thymine. Cytosine methylation can also be in the form of 5-hydroxymethylcytosine. Methylation of DNA can include methylation of non-cytosine nucleotides, such as N6-methyladenine.

As used herein, the "negative predictive value" or "NPV" can be calculated by TN/(TN+FN) or the true negative fraction of all negative test results. Negative predictive value can be inherently impacted by the prevalence of a condition in a population and pre-test probability of the population intended to be tested. The term "positive predictive value" or "PPV" can be calculated by TP/(TP+FP) or the true positive fraction of all positive test results. PPV can be inherently impacted by the prevalence of a condition in a population and pre-test probability of the population intended to be tested. See, e.g., O'Marcaigh and Jacobson, "Estimating The Predictive Value of a Diagnostic Test, How to Prevent Misleading or Confusing Results," Clin. Ped. 1993, 32(8): 485-491, which is entirely incorporated herein by reference.

As used herein, the terms "nucleic acid" and "nucleic acid molecule" are used interchangeably. The terms refer to nucleic acids of any composition form, such as deoxyribonucleic acid (DNA, e.g., complementary DNA (cDNA), genomic DNA (gDNA) and the like), and/or DNA analogs (e.g., containing base analogs, sugar analogs and/or a non-native backbone and the like), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, supercoiled, single-stranded, double-stranded and the like). A nucleic acid in some embodiments can be from a single chromosome or fragment thereof (e.g., a nucleic acid sample may be from one chromosome of a sample obtained from a diploid organism). In certain embodiments nucleic acids comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with protein or other molecules. Nucleic acids also include derivatives, variants and analogs of DNA synthesized, replicated or amplified from single-stranded ("sense" or "antisense," "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. A nucleic acid may be prepared using a nucleic acid obtained from a subject as a template.

As used herein, the term "reference genome" refers to any particular known, sequenced or characterized genome, whether partial or complete, of any organism or virus that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As used herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). In some embodiments, sequence reads (e.g., single-end or paired-end reads) can be generated from one or both strands of a targeted nucleic acid fragment. The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

As used herein, the terms "sequencing," "sequence determination," and the like as used herein refers generally to any and all biochemical processes that may be used to determine the order of biological macromolecules such as nucleic acids or proteins. For example, sequencing data can include all or a portion of the nucleotide bases in a nucleic acid molecule such as a DNA fragment.

As used herein, the term "sequencing breadth" refers to what fraction of a particular reference genome (e.g., human reference genome) or part of the genome has been analyzed. The denominator of the fraction can be a repeat-masked genome, and thus 100% can correspond to all of the reference genome minus the masked parts. A repeat-masked genome can refer to a genome in which sequence repeats are masked (e.g., sequence reads align to unmasked portions of the genome). Any parts of a genome can be masked, and thus one can focus on any particular part of a reference genome. Broad sequencing can refer to sequencing and analyzing at least 0.1% of the genome.

As used herein, the term "sequencing depth" refers to the number of times a locus is covered by a consensus sequence read corresponding to a unique nucleic acid target molecule aligned to the locus; e.g., the sequencing depth is equal to the number of unique nucleic acid target molecules covering the locus. The locus can be as small as a nucleotide, or as large as a chromosome arm, or as large as an entire genome. Sequencing depth can be expressed as "Y×", e.g., 50×, 100×, etc., where "Y" refers to the number of times a locus is covered with a sequence corresponding to a nucleic acid target; e.g., the number of times independent sequence information is obtained covering the particular locus. In some embodiments, the sequencing depth corresponds to the number of genomes that have been sequenced. Sequencing depth can also be applied to multiple loci, or the whole genome, in which case Y can refer to the mean or average number of times a loci or a haploid genome, or a whole genome, respectively, is sequenced. When a mean depth is quoted, the actual depth for different loci included in the dataset can span over a range of values. Ultra-deep sequencing can refer to at least 100× in sequencing depth at a locus.

As used herein, the term "sensitivity" or "true positive rate" (TPR) refers to the number of true positives divided by the sum of the number of true positives and false negatives. Sensitivity can characterize the ability of an assay or method to correctly identify a proportion of the population that truly has a condition. For example, sensitivity can characterize the ability of a method to correctly identify the number of subjects within a population having cancer. In another example, sensitivity can characterize the ability of a method to correctly identify the one or more markers indicative of cancer.

As used herein, the term "single nucleotide variant" or "SNV" refers to a substitution of one nucleotide at a position (e.g., site) of a nucleotide sequence, e.g., a sequence corresponding to a target nucleic acid molecule from an individual, to a nucleotide that is different from the nucleotide at the corresponding position in a reference genome. A substitution from a first nucleobase X to a second nucleobase Y may be denoted as "X>Y." For example, a cytosine to thymine SNV may be denoted as "C>T." In some embodiments, an SNV does not result in a change in amino acid expression (a synonymous variant). In some embodiments, an SNV results in a change in amino acid expression (a non-synonymous variant).

As used herein, the terms "size profile" and "size distribution" can relate to the sizes of DNA fragments in a biological sample. A size profile can be a histogram that provides a distribution of an amount of DNA fragments at a variety of sizes. Various statistical parameters (also referred to as size parameters or just parameter) can distinguish one size profile to another. One parameter can be the percentage of DNA fragment of a particular size or range of sizes relative to all DNA fragments or relative to DNA fragments of another size or range.

As used herein, the term "specificity" or "true negative rate" (TNR) refers to the number of true negatives divided by the sum of the number of true negatives and false positives. Specificity can characterize the ability of an assay or method to correctly identify a proportion of the population that truly does not have a condition. For example, specificity can characterize the ability of a method to correctly identify the number of subjects within a population not having cancer. In another example, specificity characterizes the ability of a method to correctly identify one or more markers indicative of cancer.

As used herein, the term "subject" refers to any living or non-living organism, including but not limited to a human (e.g., a male human, female human, fetus, pregnant female, child, or the like), a non-human animal, a plant, a bacterium, a fungus or a protist. Any human or non-human animal can serve as a subject, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. In some embodiments, a subject is a male or female of any age (e.g., a man, a women or a child).

As used herein, the term "tissue" can correspond to a group of cells that group together as a functional unit. More than one type of cell can be found in a single tissue. Different types of tissue may consist of different types of cells (e.g., hepatocytes, alveolar cells or blood cells), but also can correspond to tissue from different organisms (mother vs. fetus) or to healthy cells vs. tumor cells. The term "tissue" can generally refer to any group of cells found in the human body (e.g., heart tissue, lung tissue, kidney tissue, nasopharyngeal tissue, oropharyngeal tissue). In some aspects, the term "tissue" or "tissue type" can be used to refer to a tissue from which a cell-free nucleic acid originates. In one example, viral nucleic acid fragments can be derived from blood tissue. In another example, viral nucleic acid fragments can be derived from tumor tissue.

As used herein, the term "true positive" (TP) refers to a subject having a condition. "True positive" can refer to a subject that has a tumor, a cancer, a precancerous condition (e.g., a precancerous lesion), a localized or a metastasized cancer, or a non-malignant disease. "True positive" can refer to a subject having a condition, and is identified as having the condition by an assay or method of the present disclosure.

As used herein, the term "true negative" (TN) refers to a subject that does not have a condition or does not have a detectable condition. True negative can refer to a subject that does not have a disease or a detectable disease, such as a tumor, a cancer, a precancerous condition (e.g., a precancerous lesion), a localized or a metastasized cancer, a non-malignant disease, or a subject that is otherwise healthy. True negative can refer to a subject that does not have a condition or does not have a detectable condition, or is identified as not having the condition by an assay or method of the present disclosure.

The terminology used herein is for the purpose of describing particular cases only and is not intended to be limiting. As used herein, the singular forms "a," "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Exemplary System Embodiments

Details of an exemplary system are now described in conjunction with FIG. 1. FIG. 1 is a block diagram illustrating a system 100 in accordance with some implementations. The system 100 in some implementations includes at least one or more processing units CPU(s) 102 (also referred to as processors), one or more network interfaces 104, a display 106 having a user interface 108, an input device 110, a memory 111, and one or more communication buses 114 for interconnecting these components. The one or more communication buses 114 optionally include circuitry (sometimes called a chipset) that interconnects and controls communications between system components. The memory 111 may be a non-persistent memory, a persistent memory, or any combination thereof. The non-persistent memory typically includes high-speed random access memory, such as DRAM, SRAM, DDR RAM, ROM, EEPROM, flash memory, whereas the persistent memory typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. Regardless of its specific implementation, the memory 111 comprises at least one non-transitory computer-readable storage medium, and it stores thereon computer-executable executable instructions which can be in the form of programs, modules, and data structures.

In some embodiments, as shown in FIG. 1, the memory 111 stores the following:

an operating system 116, which includes procedures for handling various basic system services and for performing hardware-dependent tasks;

an optional network communication module (or instructions) 118 for connecting the system 100 with other devices and/or to a communication network;

a feature extraction module 120 for extracting feature extraction functions from datasets;

a first dataset 122 comprising, for each subject of a first plurality of subjects (subject 1-1, subject 1-2, . . . subject 1-Z), first genotypic information (126-1-1, . . . 126-1-Z) comprising a first plurality of bin values (e.g., bin counts) (128-1-1, . . . ) with each respective bin value corresponding to a bin in a plurality of bins (1, 2, . . . , N), and an indication of a cancer condition (130-1-1, . . . ) of the respective subject (subject 1-1, subject 1-2, . . . subject 1-Z) in a cancer condition set;

a first plurality of feature extraction functions 132 that are based on the first dataset 122, each feature extraction function (132-1, . . . , 132-P) in the first plurality of feature extraction functions independently encoding a linear or nonlinear function of bin values (128-1-1, . . . ) of all or a subset of the plurality of bins;

a second dataset 124 comprising, for each subject of a second plurality of subjects (subject 2-1, . . . subject 2-T), second genotypic information (134-2-1, . . . 134-2-T) comprising a second plurality of bin values (e.g., bin counts) (138-2-1, . . . ) with each respective bin value corresponding to a bin in the plurality of bins (1, 2, . . . , N), and an indication of a cancer condition (140-2-1, . . . ) of the respective subject (subject 2-1, subject 2-2, . . . subject 2-T) in the cancer condition set;

a second plurality of feature extraction functions 142 that are based on the second dataset 124, each feature extraction function (142-1, . . . , 142-S) in the second plurality of feature extraction functions independently encodes a linear or nonlinear function of bin values (138-2-1, . . . ) of all or a subset of the plurality of bins;

a transformed second dataset 150 comprising a respective plurality of feature values, also referred to herein as features (feature value 152-1, . . . , feature value 152-T), for each corresponding subject in the second plurality of subjects (subject 2-1, . . . subject 2-T), the transformed second dataset 150 generated based on the respective second plurality of bin values (e.g., bin counts) (138-2-1, . . . ) of each corresponding subject in the second plurality of subjects (subject 2-1, . . . subject 2-T) against the respective feature extraction function in the first plurality of feature extraction functions 132. As shown in FIG. 1, the feature values (feature value 152-1, . . . , feature value 152-T) comprise a plurality of feature values for each subject, e.g., feature values 152-1 for the subject 2-1 include features 154-2-1-2-1, . . . , 154-2-1-2-P, and feature values 152-T for the subject 2-T include features 154-2-T-2-1, . . . , 154-2-T-2-P), such that the transformed second dataset has the full set of feature values for each subject in the second dataset; and a first classifier 160 trained on at least a pair of cancer conditions in the cancer condition set.

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the memory 111 optionally stores a subset of the modules and data structures identified above. Furthermore, in some embodiments, the memory stores additional modules and data structures not described above. In some embodiments, one or more of the above identified elements are stored in a computer system other than the system 100, that is addressable by the system 100 so that the system 100 may retrieve all or a portion of such data when needed.

Although FIG. 1 depicts a "system 100," the figure is intended more as a functional description of the various features that may be present in computer systems than as a structural schematic of the implementations described herein. In practice, and as recognized by those of ordinary skill in the art, items shown separately could be combined and some items can be separate. Moreover, although FIG. 1 depicts certain data and modules in the memory 111 (which can be non-persistent or persistent memory), it should be appreciated that these data and modules, or portion(s) thereof, may be stored in more than one memory. For example, in some embodiments, at least the first dataset 122, the second dataset 124, the first plurality of feature extraction functions 132, and the second plurality of feature extraction functions 142 are stored in a remote storage device that can be a part of a cloud-based infrastructure. In some embodiments, at least the first dataset 122 and the second dataset 124 are stored on a cloud-based infrastructure. In some embodiments, the transformed second dataset 150 and the first classifier 160 can also be stored in the remote storage device(s).

While an example of a system in accordance with the present disclosure has been disclosed with reference to FIG.

1, methods in accordance with the present disclosure are now detailed. Any of the methods in accordance with embodiments of the present disclosure can make use of any of the assays, algorithms, or techniques, or combinations thereof, disclosed in U.S. patent application Ser. No. 15/793,830, filed Oct. 25, 2017 and/or International Patent Application No. PCT/US17/58099, filed Oct. 24, 2017, the content of each of which is hereby incorporated herein by reference in its entirety, in order to determine a cancer condition in a test subject or a likelihood that the subject has the cancer condition.

Figure 2:
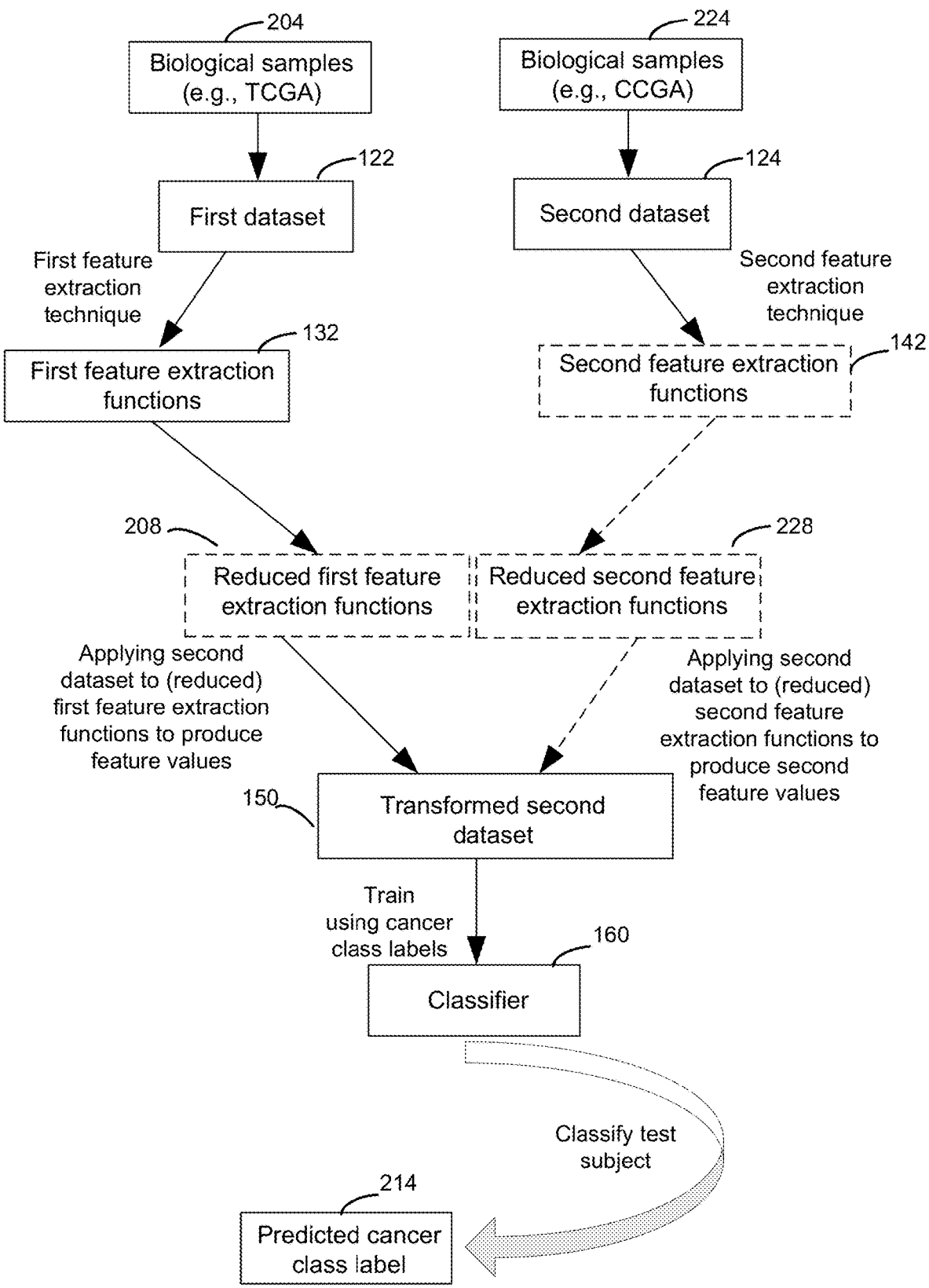
FIG. 2 is a schematic diagram of processing performed in accordance with some embodiments of the present disclosure.

FIG. 2 illustrates an overview of the techniques in accordance with some embodiments of the present disclosure. In the described embodiments, a transfer learning approach is employed where feature extraction functions obtained from a first dataset are used to train a classifier for classifying a cancer condition based on data from a second dataset. In some embodiments, the first dataset is obtained from the TCGA (Example 1), and the second dataset is obtained from the CCGA (Example 2). However, it should be appreciated that embodiments in accordance with the present disclosure are not limited to specific datasets. For example, in some embodiments, transfer learning is used between a first dataset that is binned fragment copy number count to a second dataset that is binned aberrant methylation fragment count (e.g., upon application of a p-value filter as disclosed herein).

Regardless of the specific type(s) of datasets employed in accordance with the described techniques, in some embodiments, feature extraction functions are learned on the first dataset, and the feature extraction functions are used to extract features based on the second dataset. The techniques can be implemented in any suitable computer system comprising at least one processor and a memory storing at least one program for execution by the at least one processor. As shown in FIG. 2, in some embodiments, a first dataset 122 is used that is generated using biological samples 204 obtained from each respective subject in a first plurality of subjects. The first dataset 122 can include, for each respective subject in a first plurality of subjects of a species (e.g., human), corresponding first genotypic information, such as, e.g., genotyping information 126-1-1, ..., 126-1-Z shown in FIG. 1. The genotyping information in the first dataset comprises (i) a corresponding first plurality of bin values, each respective bin value in the corresponding first plurality of bin values for a corresponding bin in a plurality of bins and (ii) an indication of a cancer condition of the respective subject in the cancer condition set, where each bin in the plurality of bins represents a portion of a reference genome of the species. Thus, FIG. 3 illustrates an example of the first dataset comprising, for each subject 1-1, 1-2, ..., 1-Z in the first plurality of subjects, a corresponding first plurality of bin values for each subject ($cnt_{1-1-1}$, $cnt_{1-1-2}$, $cnt_{1-1-3}$, ..., $cnt_{1-1-N}$ for subject 1-1; $cnt_{1-2-1}$, $cnt_{1-1-2-2}$, $cnt_{1-2-3}$, ..., $cnt_{1-2-N}$ for subject 1-2; ...; $cnt_{1-Z-1}$, $cnt_{1-Z-2}$, $cnt_{1-Z-3}$, ..., $cnt_{1-Z-N}$ for subject 1-Z) and a respective indication of a cancer condition (a "value" or a "label") ($L_{1-1}$, $L_{1-2}$, ..., $L_{1-Z}$) for each subject.

Figure 23:
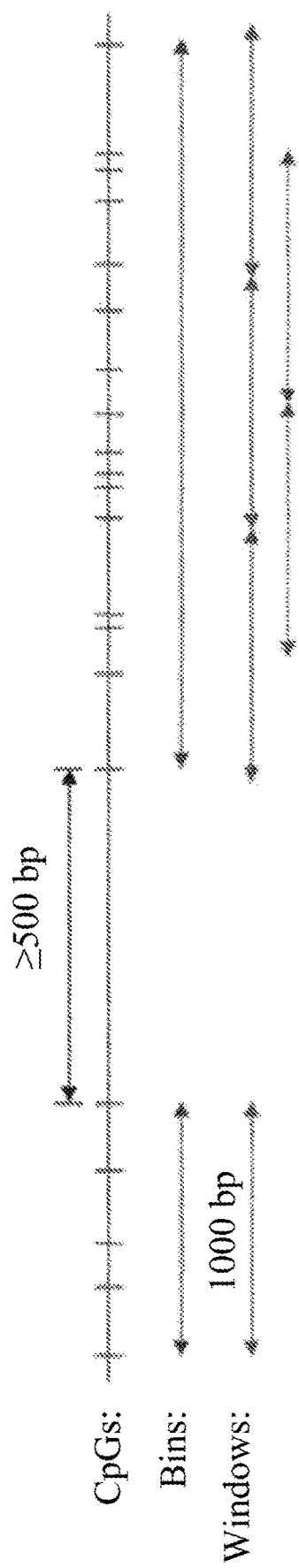
FIG. 23 is an illustration of bins (blocks) of a reference genome, in accordance with an aspect of the present disclosure.

FIG. 23 is an illustration of bins of a reference genome, according to some embodiments of the present disclosure. A reference genome (or a subset of the reference genome) is partitioned in one or more stages, e.g., for use cases involving a targeted methylation assay (e.g., where the first and/or second dataset included binned methylation data). For instance, in some embodiments, the reference genome is divided into bins (blocks) of CpG sites. In some such embodiments, each bin is defined when there is a separation between two adjacent CpG sites that exceeds a threshold, e.g., greater than 200 base pairs (bps), 300 bps, 400 bps, 500 bps, 600 bps, 700 bps, 800 bps, 900 bps, or 1,000 bps, among other values. Bins can vary in size of base pairs. In the case where the first or second dataset is methylation data from targeted sequencing, a common size for bins is around 200 bps, with a range from about 30 bps to about 1000 bps or greater. In some embodiments, each bin is between 30 bps and 5000 bps. In some embodiments, when a respective bin in a plurality of bins is larger than a threshold size (e.g., 900 bps, 1000 bps, 1100 bps, etc.) the respective bin is subdivided into windows of a certain length, e.g., 500 bps, 600 bps, 700 bps, 800 bps, 900 bps, 1,000 bps, 1,100 bps, 1,200 bps, 1,300 bps, 1,400 bps, or 1,500 bps, among other values and each such window receives its own independent bin value. In other embodiments, the windows can be from 200 bps to 10 kilobase pairs (kbp), from 500 bp to 2 kbp, or about 1 kbp in length. Windows (e.g., that are adjacent) can overlap by a number of base pairs or a percentage of the length, e.g., 10%, 20%, 30%, 40%, 50%, or 60%, among other values. In embodiments, where a bin is divided into a plurality of windows, each feature extraction function of the present disclosure independently encodes a linear or non-linear function of window values for each of the windows of the respective bin. In some embodiments, rather than dividing larger bins into windows, such larger bins are divided into smaller bins. In some embodiments, such smaller bins overlap each other while in other embodiments they do not overlap each other.

Figure 10A:
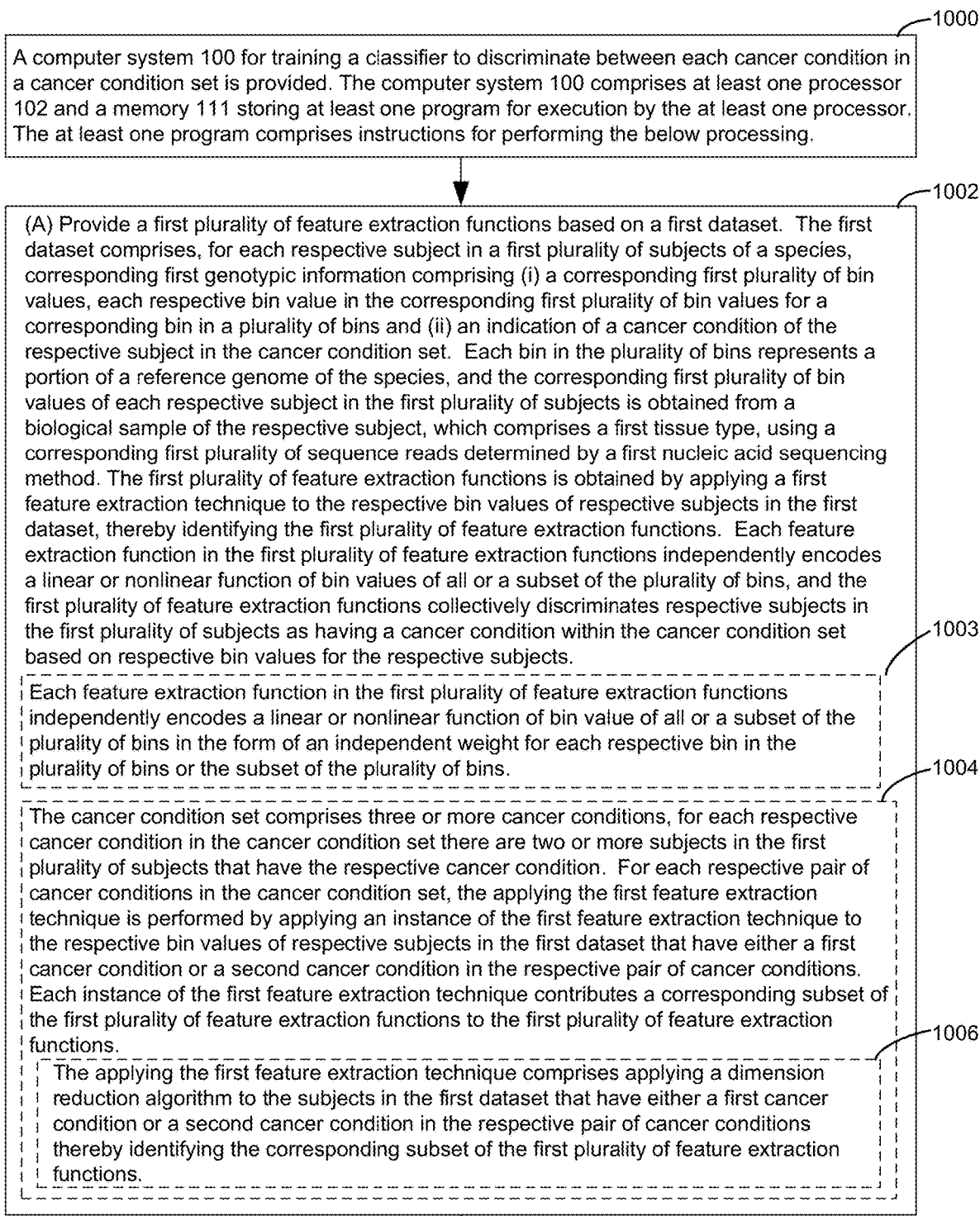

Continuing with block 1002 of FIG. 10A, each sample in the biological samples 204 of the first subjects can comprise a first tissue type, and the corresponding first plurality of bin values of each respective subject in the first plurality of subjects can be generated using a corresponding first plurality of sequence reads determined by a first nucleic acid sequencing method.

Figure 4:
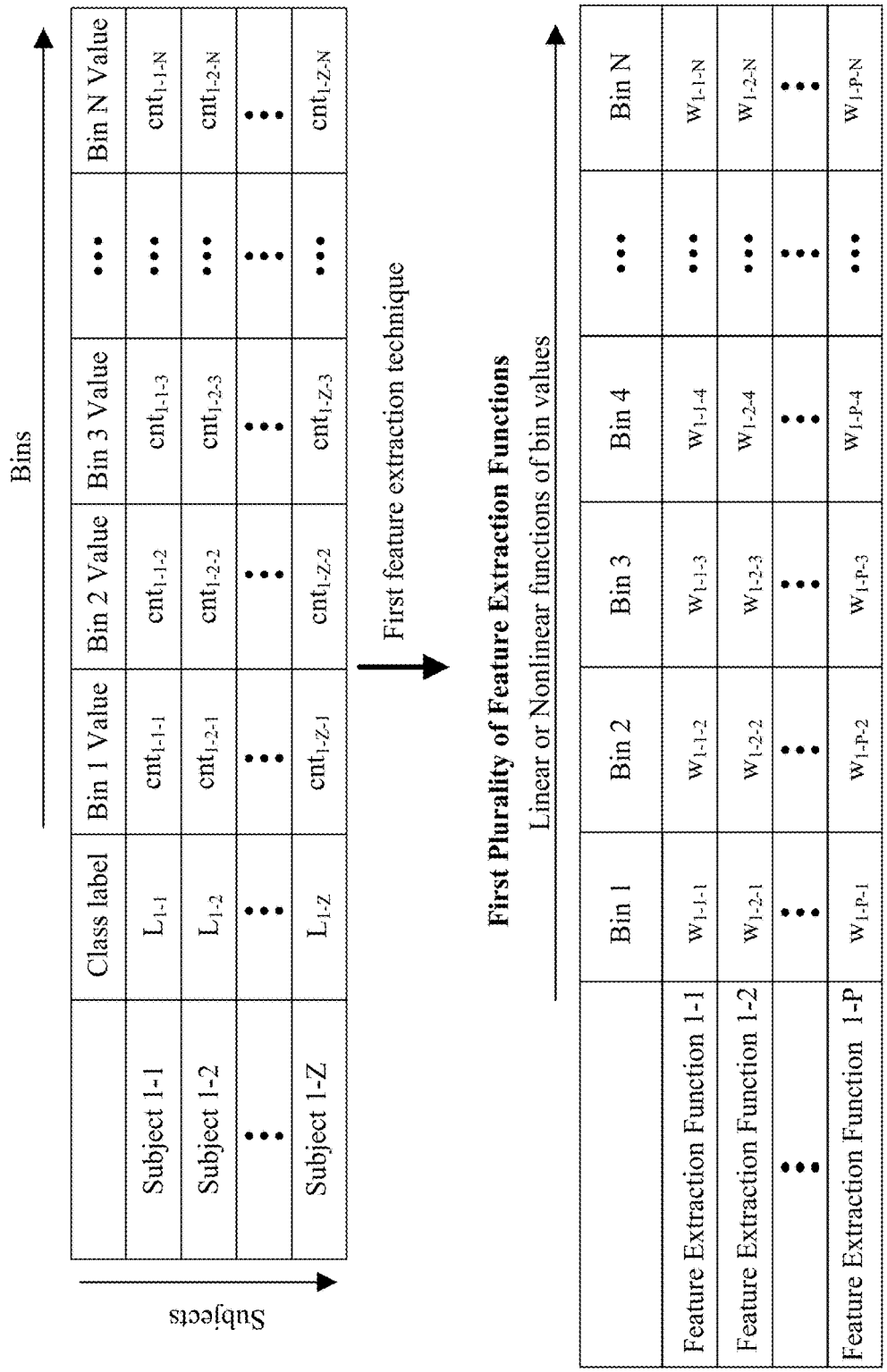
FIG. 4 illustrates an example of the first dataset of FIG. 3, and an example of a first plurality of feature extraction functions generated by applying a first feature extraction technique to the first dataset, in accordance with some embodiments of the present disclosure.

As shown schematically in FIG. 2, a first plurality of feature extraction functions ("First feature extraction functions") 132 can be obtained, and provided, based on the first dataset 122. The first plurality of feature extraction functions 132 can be obtained by applying a first feature extraction technique to the respective bin values of respective subjects in the first dataset 122. In some embodiments, each feature extraction function in the first plurality of feature extraction functions 132 independently encodes a linear or nonlinear function of bin values of all or a subset of the plurality of bins. FIG. 4 illustrates an example of the first plurality of feature extraction functions 132, where each feature extraction function 1-1, 1-2, ..., 1-P is schematically shown to be based on respective bin values, such that each feature extraction function encodes a linear or nonlinear function of the respective bin values of all or a subset of the bins 1, ..., N. Thus, in this example, feature extraction function 1-1 is based on values $w_{1-1-1}*(bin\ 1)$, $w_{1-1-2}*(bin\ 2)$, $w_{1-1-3}*(bin\ 3)$, $w_{1-1-4}*(bin\ 4)$, ..., $w_{1-1-N}*(bin\ N)$, where, in some embodiments, $w_{1-1-1}$, $w_{1-1-2}$, $w_{1-1-3}$, $w_{1-1-4}$, ..., $w_{1-1-N}$ are respective weights of the feature extraction function, and bin 1 ... bin N are the measured bin counts of corresponding bins 1 ... N. In this example, feature extraction function 1-2 is based on values $w_{1-2-1}*(bin\ 1)$, $w_{1-2-2}*(bin\ 2)$, $w_{1-2-3}*(bin\ 3)$, $w_{1-2-4}*(bin\ 4)$, ..., $w_{1-2-N}*(bin\ N)$; and feature extraction function 1-P is based on values $w_{1-P-1}*(bin\ 1)$, $w_{1-P-2}*(bin\ 2)$, $w_{1-P-3}*(bin\ 3)$, $w_{1-P-4}*(bin\ 4)$, ..., $w_{1-P-N}*(bin\ N)$. It will be appreciated that these are linear examples of feature extraction functions and that the present disclosure further encompasses nonlinear examples of feature extraction functions.

Regardless of the specific way in which the feature extraction functions are generated, in some embodiments, the first plurality of feature extraction functions collectively discriminate respective subjects in the first plurality of subjects as having a cancer condition within a cancer condition set based on respective bin values for the respective subjects. In some embodiments, the described methods allow discriminating a subject as having a cancer condition in the cancer condition set versus another cancer condition in the cancer condition set. In some embodiments, the described methods allow discriminating a subject as having a cancer condition in the cancer condition set versus all other conditions (cancer or non-cancer) in the cancer condition set.

In some embodiments, applying the first feature extraction technique comprises applying a dimension reduction algorithm to the subjects in the first dataset 122.

FIG. 2 also illustrates that a second dataset 124 can be used that is generated using biological samples 224 obtained from each respective subject in a second plurality of subjects. The second dataset 124 can include, for each respective subject in a second plurality of subjects of a species (e.g., human), corresponding second genotypic information, such as, e.g., genotyping information 134-2-1, ..., 134-1-T shown in FIG. 1. The genotyping information in the second dataset 124 comprises (i) a corresponding second plurality of bin values, each respective bin value in the corresponding second plurality of bin values for a corresponding bin in a plurality of bins and (ii) an indication of a cancer condition of the respective subject in the cancer condition set, where each bin in the plurality of bins represents a portion of a reference genome of the species. Thus, FIG. 3, lower panel, illustrates an example of the second dataset comprising, for each subject 2-1, 2-2, ..., 2-T in the second plurality of subjects, a corresponding second plurality of bin values for each subject ($cnt_{2-1-1}$, $cnt_{2-1-2}$, $cnt_{2-1-3}$, ..., $cnt_{2-1-N}$ for subject 2-1; $cnt_{2-2-1}$, $cnt_{2-2-2}$, $cnt_{2-2-3}$, ..., $cnt_{2-2-N}$ for subject 2-2; ...; $cnt_{2-T-1}$, $cnt_{2-T-2}$, $cnt_{2-T-3}$, ..., $cnt_{2-T-N}$ for subject 2-T) and an indication of a cancer condition (a value or a "label") ($L_{2-1}$, $L_{2-2}$, ..., $L_{2-T}$) for each subject.

In some embodiments, each sample in the biological samples 224 of the second subjects can comprise a second tissue type, and a second sequencing method can be used to generate the corresponding second plurality of bin values of each respective subject in the second plurality of subjects. Further, in some embodiments, the first sequencing method differs from the second sequencing method or the first tissue type differs from the second tissue type. For example, in some embodiments, the first sequencing method is whole genome or targeted sequencing and the bin information of the first dataset comprises fragment copy number counts of cell free nucleic acid and the second dataset is whole genome or targeted genome bisulfite sequencing and the second dataset comprises aberrant methylation fragment counts, where such aberrant methylation fragment counts are determined using the methods disclosed herein, such as those of Examples 5 and 10 below.

Figure 5:
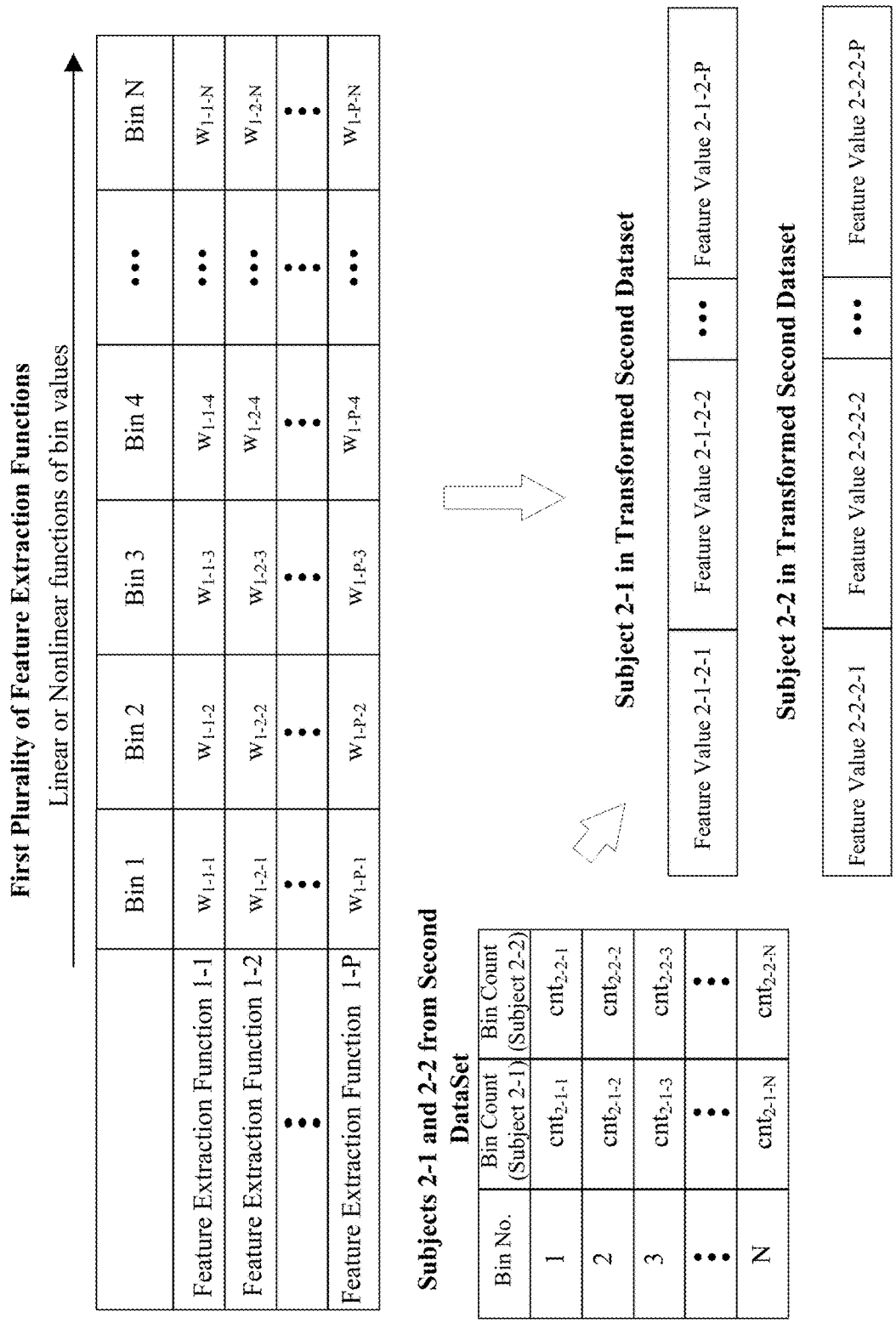
FIG. 5 illustrates partial generation of a transformed second dataset, using the first plurality of feature extraction functions and bin counts for subjects in the second dataset, in accordance with some embodiments of the present disclosure.

In some embodiments, the feature extraction functions learned on the first dataset are applied onto the second dataset to extract features from the second dataset. In some embodiments, as mentioned above, the first dataset is obtained from the TCGA and the second dataset is obtained from the CCGA, though other type(s) of datasets can be used additionally or alternatively. As shown in FIG. 2, a transformed second dataset 150 can be generated based on the first plurality of feature extraction functions 132 by applying the first plurality of feature extraction functions 132 onto the respective second plurality of bin values of each corresponding subject in the second plurality of subjects (the second dataset 124). The respective second plurality of bin values of each corresponding subject in the second plurality of subjects are transformed against the respective feature extraction function from the first plurality of feature extraction functions 132. The transformed second dataset comprises a respective plurality of features (or feature values) for each corresponding subject. In this way, FIG. 5 shows by way of example schematic representations of feature values (2-1-2-1, 2-1-2-2, ..., 2-1-2-P) for subject 2-1 and feature values (2-2-2-1, 2-2-2-2, ..., 2-2-2-P) for subject 2-2 in the transformed second dataset 150. The feature values are similarly generated for each of the subjects.

In some embodiments, a feature (also referred to herein as a "feature value") is the computational result of the inputting of bin counts (or other bin values) into a feature extraction function. As discussed above, a feature extraction function can be a linear or nonlinear combination of bin values. The feature values collectively may determine a vector for the subject. For example, in embodiments in which each feature extraction function is a principal component, each feature value includes the bin values projected onto the particular principal component.

Figure 8:
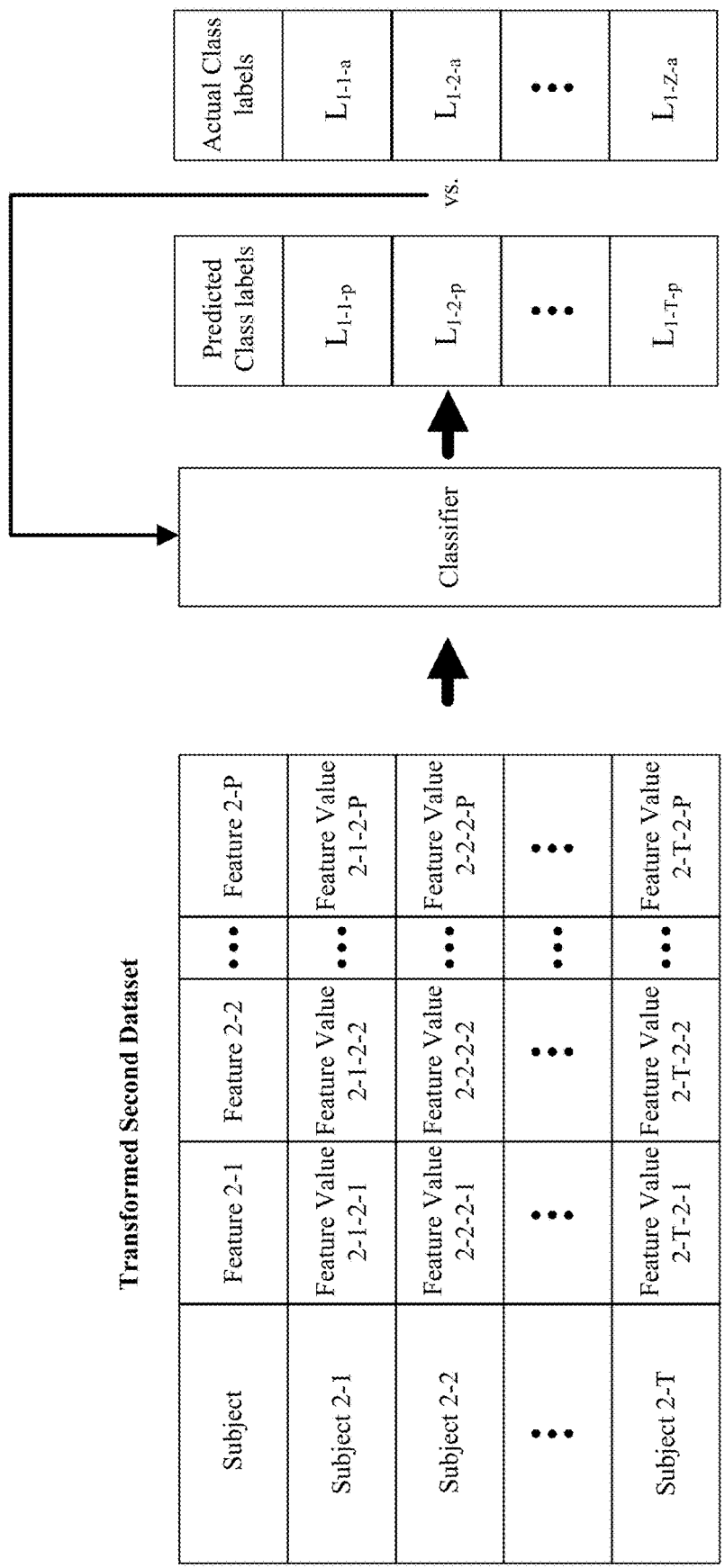
FIG. 8 illustrates the transformed second dataset that is used to train a classifier, in accordance with some embodiments of the present disclosure.

The transformed second dataset 150 is used, in conjunction with the indication of the cancer condition of respective subjects in the second plurality of subjects (second dataset 124, FIGS. 2 and 3) to train a classifier 160 on at least a pair of cancer conditions in the cancer condition set. As shown in FIG. 2, the classifier 160 (e.g., first classifier 160 of FIG. 1), which can comprise one or more classifiers (including classifiers of different types), is trained using cancer class labels for genotypic information obtained from a biological sample from each subject in the second dataset, e.g., class labels $L_{2-1}$, $L_{2-2}$, ..., $L_{2-T}$ (FIG. 3) for each subject. FIG. 8 illustrates an example of a transformed second dataset including feature values for subject 2-1 (feature values 2-1-2-1, 2-1-2-2, ..., 2-1-2-P), subject 2-2 (feature values 2-2-2-1, 2-2-2-2, ..., 2-2-2-P), ..., subject 2-T (feature values 2-T-2-1, 2-T-2-2, ..., 2-T-2-P). As also shown schematically in FIG. 8, the transformed second dataset is applied, along with actual class labels ($L_{1-1-a}$, $L_{1-2-a}$, ..., $L_{1-Z-a}$), to train a classifier such that it can generate predicted class labels ($L_{1-1-p}$, $L_{1-2-p}$, ..., $L_{1-T-p}$).

The classifier 160 can be a classifier of any suitable type. For example, the classifier 160 can be regression (e.g., multivariate logistic regression), a neural network, a convolutional neural network, a support vector machine, a decision tree, or a clustering technique.

In some such embodiments, such classifiers output a single cancer condition for a given cancer condition set upon inputting the feature values for a respective subject in the transformed second dataset. In some such embodiments, such classifiers output a separate probability of each cancer condition in the given cancer condition set upon inputting the feature values for a respective subject in the transformed second dataset. The cancer condition (or cancer condition probability of each cancer condition in the cancer condition set outputted by the classifier during training are compared to the actual cancer conditions of the subjects in the transformed second dataset. In some embodiments, particularly classifiers in the form of convolutional neural networks, errors in cancer condition assignment made by the classifier, as verified against the transformed second dataset, are then back-propagated through the weights of the classifier in order to train the classifier. For instance, in the example case where the classifier is a convolutional neural network, the filter weights of respective filters in the convolutional layers of the network are adjusted in such back-propagation. In an exemplary embodiment, the classifier is a neural network trained against the errors in the cancer condition assignments made by the classifier, in view of the actual cancer conditions of the subjects of the transformed second dataset, by stochastic gradient descent with the AdaDelta adaptive learning method (Zeiler, 2012 "ADADELTA: an adaptive learning rate method," CoRR, vol. abs/1212.5701, which is hereby incorporated by reference), and the back propagation algorithm provided in Rumelhart et al., 1988, "Neurocomputing: Foundations of research," ch. Learning Representations by Back-propagating Errors, pp. 696-699, Cambridge, MA, USA: MIT Press, which is hereby incorporated by reference.

The trained classifier 160 is used to classify a test subject to a cancer condition using as input to the classifier genotypic information on the test subject, the genotyping information being based on sequence read data in a test biological sample obtained from the test subject. In this way, the classifier 160 is used to predict a cancer-related value (e.g., a label indicating a cancer/non-cancer condition, a stage of the cancer, survival time, etc.) 214 for the test subject, as shown in FIG. 2.

Figure 6:
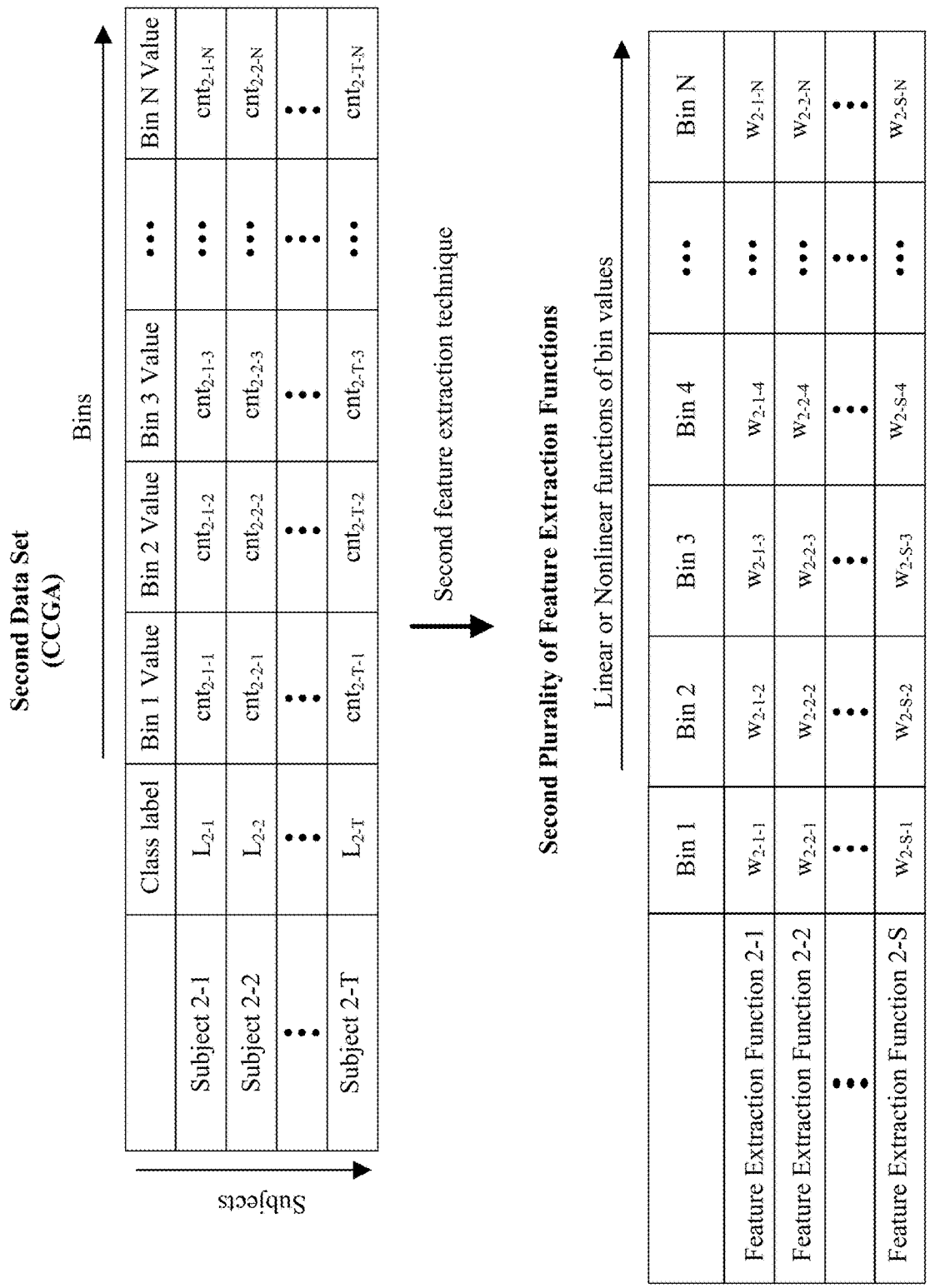
FIG. 6 illustrates an example of the second dataset of FIG. 3, and an example of a second plurality of feature extraction functions generated by applying a second feature extraction technique to the second dataset, in accordance with some embodiments of the present disclosure.

Furthermore, as also shown in FIG. 2, in some embodiments, in addition to applying the first feature extraction technique to the respective bin values of respective subjects in the first dataset 122, a second feature extraction technique is applied to the respective bin values of respective subjects in the second dataset 124, thereby identifying a second plurality of feature extraction functions ("Second feature extraction functions") 142. FIG. 6 illustrates an example of the second plurality of feature extraction functions 142, where each feature extraction function 2-1, 2-2, ..., 2-S is schematically shown to be based on respective bin values, such that each feature extraction function encodes a linear or nonlinear function of the respective bin values of all or a subset of the bins 1, ..., N. Each feature extraction function in the second plurality of feature extraction function independently encodes a linear or nonlinear function of bin values of all or a subset of the plurality of bins. In this example, feature extraction function 2-1 is based on bin values $W_{2-1-1}$*(bin 1), $w_{2-1-2}$*(bin 2), $w_{2-1-3}$*(bin 3), $w_{2-1-4}$*(bin 4), ..., $w_{2-1-N}$*(bin N); feature extraction function 2-2 is based on bin values $w_{2-2-1}$*(bin 1), $w_{2-2-2}$*(bin 2), $w_{2-2-3}$*(bin 3), $w_{2-2-4}$*(bin 4), ..., $w_{2-2-N}$*(bin N); and feature extraction function 2-S is based on bin values $w_{2-S-1}$*(bin 1), $w_{2-S-2}$*(bin 2), $W_{2-S-3}$*(bin 3), $W_{2-S-4}$*(bin 4), ..., $W_{2-S-N}$*(bin N). It will be appreciated that these are linear examples of feature extraction functions and that the present disclosure further encompasses nonlinear examples of feature extraction functions. The second plurality of feature extraction functions collectively discriminate respective subjects in the second plurality of subjects as having a cancer condition within the cancer condition set based on respective bin values for the respective subjects.

Figure 7:
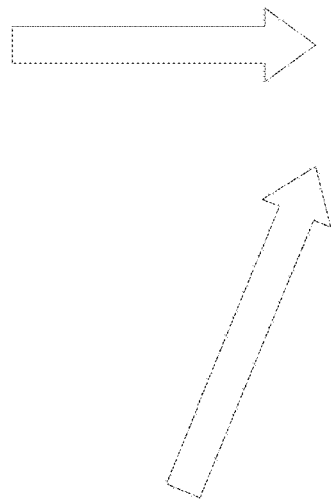
FIG. 7 illustrates the transformed second dataset and the second features (shown partially) obtained using the second plurality of feature extraction functions, in accordance with some embodiments of the present disclosure.
Figure 9:
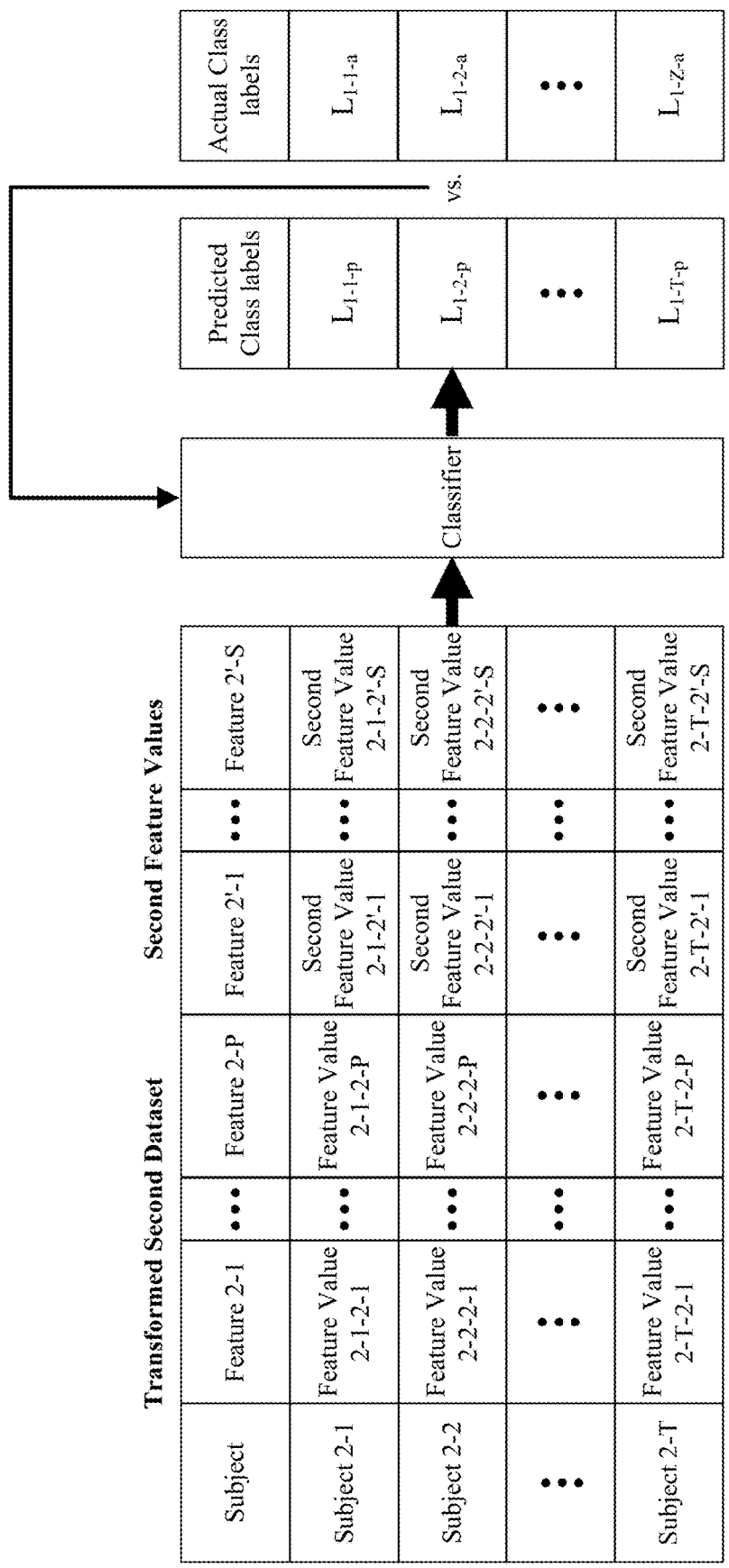
FIG. 9 illustrates the transformed second dataset and the second plurality of feature extraction functions that are used together to train a classifier, in accordance with some embodiments of the present disclosure.

In some embodiments, as shown in FIG. 2, features, or feature values, obtained using the second plurality of feature extraction functions 142 are included in the transformed second dataset 150 to train the classifier 160. FIG. 7 illustrates the second features obtained using the second plurality of feature extraction functions 142 for subject 2-1 and used together with the transformed second dataset 150. As shown, second feature values (2-1-2'-1, ..., 2-1-2'-S) (or the second plurality of feature values) obtained using the second feature extraction functions 142 are appended to feature values (2-1-2-1, ..., 2-1-2-P) in the transformed second dataset 150 that were obtained based on the first feature extraction functions 132. FIG. 9 illustrates an example of a transformed second dataset including feature values for subject 2-1 (feature values 2-1-2-1, ..., 2-1-2-P), subject 2-2 (feature values 2-2-2-1, ..., 2-2-2-P), ..., subject 2-T (feature values 2-T-2-1, ..., 2-T-2-P), combined with second feature values for subject 2-1 (feature values 2-1-2'-1, ..., 2-1-2'-S), subject 2-2 (feature values 2-2-2'-1, ..., 2-2-2'-S), ..., subject 2-T (feature values 2-T-2'-1, ..., 2-T-2'-S). As also shown schematically in FIG. 9, the transformed second dataset and the second plurality of feature values are applied, along with actual values or labels ($L_{1-1-a}$, $L_{1-2-a}$, ..., $L_{1-Z-a}$), to train a classifier so that it can generate predicted values or labels ($L_{1-1-p}$, $L_{1-2-p}$, ..., $L_{1-T-p}$).

The second dataset 124 can be applied to the second feature extraction functions 142 to produce the second features (or the second feature values) that can be used in addition to the transformed second dataset 150 to train the classifier 160 in different ways. In this way, the transformed second dataset 150 can comprise the second feature values. For example, in embodiments in which the first dataset is a TCGA dataset and the second dataset is a CCGA dataset, TCGA-based feature extraction functions and CCGA-based feature extraction functions are applied separately to the CCGA data before being combined as input into the classifier. In alternative embodiments in which the first dataset is a TCGA dataset and the second dataset is a CCGA dataset, using the second plurality of feature extraction functions in addition to the transformed second dataset to train the first classifier involves applying the second plurality of feature extraction functions against the transformed second dataset prior to training the classifier. In other words, TCGA-based feature extraction functions are applied to CCGA data to obtain processed CCGA data, and CCGA-based feature extraction functions are then applied to the already processed CCGA data.

In some embodiments, the first feature extraction functions 132 can be pruned to generate reduced number of feature extraction functions 208, as shown in FIG. 2. This can be done using the first feature extraction functions 132 and respective indications of the cancer condition of respective subjects in the first plurality of subjects thereby removing a number of feature extraction functions from the first feature extraction functions 132. The pruning can comprise applying to the first feature extraction functions 132 a regression technique, such as, e.g., logic regression such as regularized logistic regression. In embodiments in which the pruning of the first feature extraction functions 132 is performed, the reduced number of first feature extraction functions 208 is used in generating the transformed second dataset, as shown in FIG. 2. The second feature extraction functions 142 can be similarly pruned to generate reduced number of second feature extraction functions 228, as also shown in FIG. 2. In this way, the second dataset can be applied to the reduced number of second feature extraction functions 228 thereby generating the second feature values that can be used to train the classifier 160. Thus, FIG. 2 illustrates schematically that the transformed second dataset 150 can be generated based on the feature values obtained by applying the second dataset 124 to the reduced number of first feature extraction functions 208, and based on the second feature values obtained by applying the second dataset 124 to the reduced number of second feature extraction functions 228.

FIGS. 10A-10H illustrate an example of a method in accordance with some embodiments of the present disclosure.

Data Blocks 1000-1020

As shown at block 1000, the method can be implemented by the computer system 100 (FIG. 1) for training a classifier to discriminate between each cancer condition in a cancer condition set. The computer system 100 comprises at least one processor 102 and the memory 111 storing at least one program for execution by the at least one processor. The at least one program comprises instructions for performing the processing shown in FIGS. 10A-10H and described in detail below.

At block 1002 of FIG. 10A, a first plurality of feature extraction functions 132 based on a first dataset 122 are provided. The first dataset 122 comprises, for each respective subject in a first plurality of subjects (e.g., 10 or more subjects, 20 or more subjects, 50 or more subjects, 100 or more subjects) of a species (e.g., human), corresponding first genotypic information (126-1-1, . . . , 126-1-Z) comprising (i) a corresponding first plurality of bin values (e.g., bin values 128-1-1, . . . , for N bins for subject 1-1, as shown in FIG. 1), each respective bin value in the corresponding first plurality of bin values for a corresponding bin in a plurality of bins and (ii) an indication of a cancer condition of the respective subject in the cancer condition set (e.g., an indication 130-1-1 of a cancer condition for subject 1-1, as shown in FIG. 1).

Each bin in the plurality of bins represents a portion of a reference genome of the species, and the corresponding first plurality of bin values of each respective subject in the first plurality of subjects is obtained from a biological sample of the respective subject, which comprises a first tissue type, using a corresponding first plurality of sequence reads determined by a first nucleic acid sequencing method using a first sequencing method. Example 10 provides one example of a first sequence method in which methylation information is derived from the sequence reads and used to form bin values.

The first plurality of feature extraction functions is obtained by applying a first feature extraction technique to the respective bin values of respective subjects in the first dataset, thereby identifying the first plurality of feature extraction functions, where each feature extraction function in the first plurality of feature extraction functions independently encodes a linear or nonlinear function of bin values of all or a subset of the plurality of bins, and the first plurality of feature extraction functions collectively discriminate respective subjects in the first plurality of subjects as having a cancer condition within the cancer condition set based on respective bin values for the respective subjects. The species can be human, though it should be appreciated that the described methods can be applied to other types of species.

The bin values in the corresponding first plurality of bin values of a subject in the first plurality of subjects can be obtained in various ways, including using sequence reads and/or microarray technologies that use relative quantitation in which the intensity of a signal (at a spot (e.g., a DNA spot)) is compared to the intensity of the signal of the same spot under a different condition, and the identity of the feature is known by its position. Any suitable number of sequence reads can be used. For example, in some embodiments, the corresponding first plurality of bin values of a respective subject in the first plurality of subjects is determined using more than 1000, more than 3000, more than 5000, more than 10000, or more than 20000, more than 50000, or more than 100000 sequence reads that are collectively taken from the biological sample of the respective subject in accordance with the first sequencing method.

Sequence reads used to form the first plurality of bin values of a respective subject in the first plurality of subjects across the genome of the species can be at least 10×, at least 20×, or at least 40×. In some embodiments, each respective sequence read used to form the first plurality of bin values of a respective subject in the first plurality of subjects includes (i) a first portion mappable onto the genome of the species and (ii) a second portion. In some embodiments, the sequence reads used to form the first plurality of bin values of a respective subject in the first plurality of subjects are filtered so that only sequence reads whose first portion is less than 160 nucleotides are used to form the bin values.

In some embodiments, the genotypic information is obtained by whole genome sequencing or targeted panel sequencing of a biological sample from subjects. For example, the sequencing can be performed by whole genome sequencing and the average coverage rate of the plurality of sequence reads taken from a biological sample from a training subject is at least 1×, 2×, 3×, 4×, 5×, 6×, 7×, 8×, 9×, 10×, at least 20×, at least 30×, at least 40×, at least 50×, at least 100×, or at least 200× across the genome of the test subject. When sequencing (methylation- or nonmethylation-based) using a targeted panel is performed, the average coverage rate of the plurality of sequence reads taken from a biological sample from a training subject is at least 200×, 200×, 500×, 1,000×, at least 2,000×, at least 3,000×, or at least 4,000×, at least 5,000×, at least 10,000×, at least 20,000×, at least 30,000×, or at least 50,000× across selected regions in the genome of the test subject.

In some embodiments, the biological sample is plasma. In some embodiments, the biological sample comprises blood, whole blood, plasma, serum, urine, cerebrospinal fluid, fecal, saliva, sweat, tears, pleural fluid, pericardial fluid, or peritoneal fluid of the subject. In some embodiments, the biological sample consists of blood, whole blood, plasma, serum, urine, cerebrospinal fluid, fecal, saliva, sweat, tears, pleural fluid, pericardial fluid, or peritoneal fluid of the subject.

In some embodiments, the biological sample is processed to extract cell-free nucleic acids in preparation for sequencing analysis. By way of a non-limiting example, in some embodiments, cell-free nucleic acid is extracted from a blood sample collected from a subject in K2 EDTA tubes. Samples are processed within two hours of collection by double spinning of the blood first at ten minutes at 1000 g then plasma ten minutes at 2000 g. The plasma is then stored in 1 ml aliquots at −80° C. In this way, a suitable amount of plasma (e.g. 1-5 ml) is prepared from the biological sample for the purposes of cell-free nucleic acid extraction. In some such embodiments cell-free nucleic acid is extracted using the QIAamp Circulating Nucleic Acid kit (Qiagen) and eluted into DNA Suspension Buffer (Sigma). In some embodiments, the purified cell-free nucleic acid is stored at −20° C. until use. See, for example, Swanton et al., 2017, "Phylogenetic ctDNA analysis depicts early stage lung cancer evolution," Nature, 545(7655): 446-451, which is hereby incorporated herein by reference in its entirety. Other equivalent methods can be used to prepare cell-free nucleic acid using biological methods for the purpose of sequencing, and all such methods are within the scope of the present disclosure.

In some embodiments, the cell-free nucleic acid that is obtained from the first biological sample is in any form of nucleic acid, or a combination thereof. For example, in some embodiments, the cell-free nucleic acid that is obtained from a biological sample is a mixture of RNA and DNA.

The time between obtaining a biological sample and performing an assay, such as a sequence assay, can be optimized to improve the sensitivity and/or specificity of the assay or method. In some embodiments, a biological sample can be obtained immediately before performing an assay. In some embodiments, a biological sample can be obtained, and stored for a period of time (e.g., hours, days or weeks) before performing an assay. In some embodiments, an assay can be performed on a sample within 1 day, 2 days, 3 days, 4 days, 5 days, 6 days, 1 week, 2 weeks, 3 weeks, 4 weeks, 5 weeks, 6 weeks, 7 weeks, 8 weeks, 3 months, 4 months, 5 months, 6 months, 1 year, or more than 1 year after obtaining the sample from the training subject.

In some embodiments, the genotypic information for each respective subject in the first plurality of subjects is obtained by targeted panel sequencing in which the sequence reads taken from a biological sample of a training subject in order to form the genotypic construct 126 have at least 50,000× coverage for this targeted panel of genes, at least 55,000× coverage for this targeted panel of genes, at least 60,000× coverage for this targeted panel of genes, or at least 70,000× coverage for this targeted panel of genes. In some such embodiments, the targeted panel of genes is between 450 and 500 genes. In some embodiments, the targeted panel of genes is within the range of 500±5 genes, within the range of 500±10 genes, or within the range 500±25 genes.

In some embodiments, the first sequencing method is a whole genome sequencing assay. A whole genome sequencing assay refers to a physical assay that generates sequence reads for a whole genome or a substantial portion of the whole genome which can be used to determine large variations such as copy number variations or copy number aberrations. Such a physical assay may employ whole genome sequencing techniques or whole exome sequencing techniques.

In some embodiments, the first sequencing method comprises whole genome bisulfite sequencing. In some of such embodiments, the whole genome bisulfite sequencing identifies one or more methylation state vectors as described, for example, in U.S. patent application Ser. No. 16/352,602, entitled "Anomalous Fragment Detection and Classification," filed Mar. 13, 2019, which is hereby incorporated by reference, or in accordance with any of the techniques disclosed in U.S. patent application Ser. No. 15/931,022, entitled "Model Based Featurization and Classification," filed May 13, 2020, which is hereby incorporated by reference.

In some embodiments, the genotypic information is generated from a TCGA dataset, as described in Example 2 below.

Figure 20:
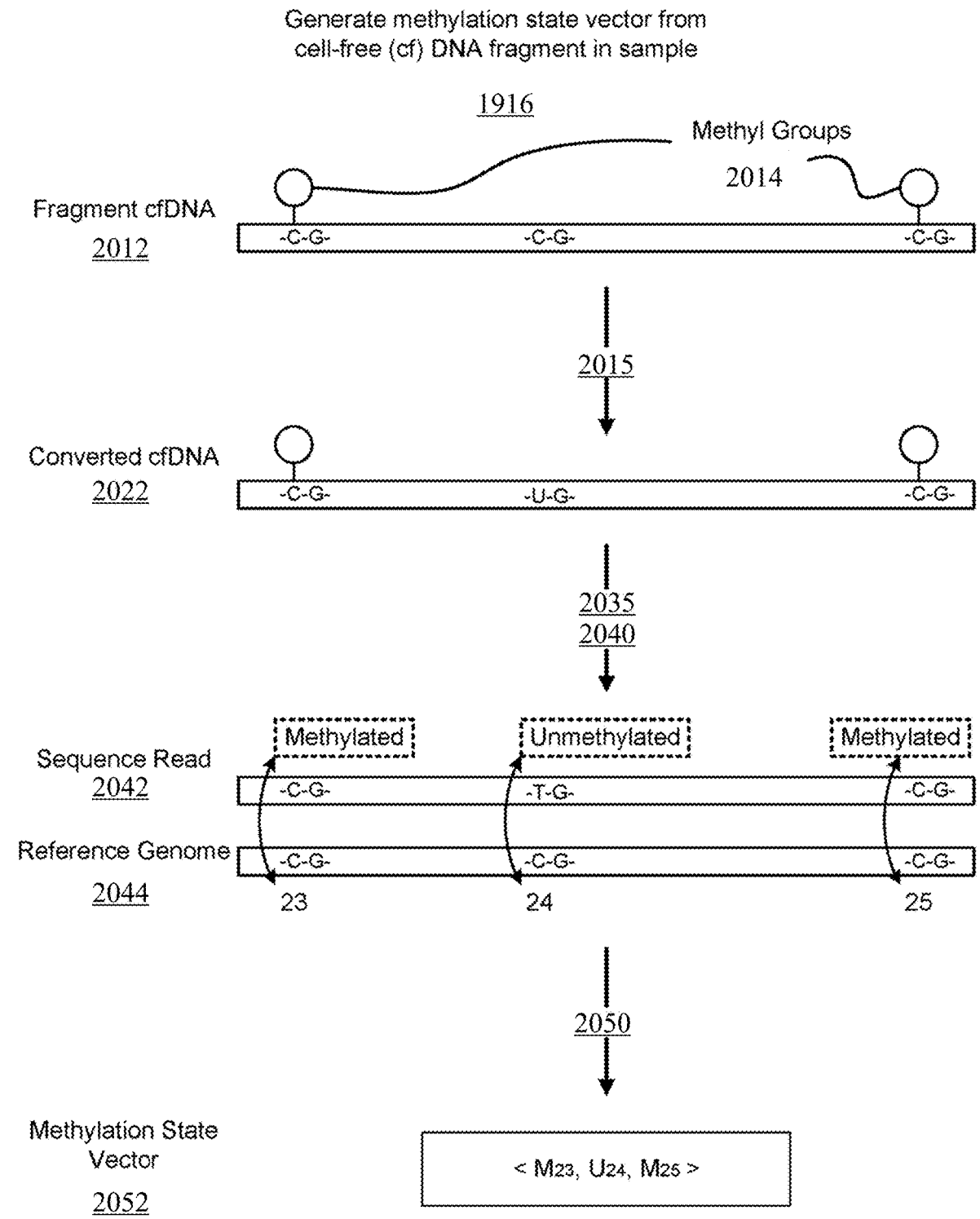
FIG. 20 is an illustration of a part of the process of sequencing nucleic acids to obtain methylation information and methylation state vectors, in accordance with an aspect of the present disclosure.

In some embodiments, the genotypic information is generated as disclosed in Examples 5 and 10 below. That is, in some embodiments, the genotypic information is in the form of a methylation state vector 2052 as described in Example 10 below in conjunction with FIG. 20. In some embodiments, the genotypic information is in the form of a methylation state vector 2052 as described in Example 10 below in conjunction with FIG. 20, provided that the methylation state vector satisfied one or more filter conditions disclosed herein, such as the p-value filter disclosed, for example, in Example 5 in conjunction with FIGS. 21 and 22.

In some embodiments, the sequence reads are pre-processed to correct biases or errors using one or more methods such as normalization, correction of GC biases, and/or correction of biases due to PCR over-amplification.

The first sequencing method can comprise any form of sequencing that can be used to obtain a number of sequence reads measured from cell-free nucleic acids, including, but not limited to, high-throughput sequencing systems such as the Roche 454 platform, the Applied Biosystems SOLID platform, the Helicos True Single Molecule DNA sequencing technology, the sequencing-by-hybridization platform from Affymetrix Inc., the single molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and nanopore sequencing also can be used to obtain sequence reads 140 from the cell-free nucleic acid obtained from the biological sample.

In some embodiments, sequencing-by-synthesis and reversible terminator-based sequencing (e.g., Illumina's Genome Analyzer; Genome Analyzer II; HISEQ 2000; HISEQ 2500 (Illumina, San Diego Calif.)) is used to obtain sequence reads from the cell-free nucleic acid obtained from a biological sample of a training subject in order to form the genotypic construct 126. In some such embodiments, millions of cell-free nucleic acid (e.g., DNA) fragments are sequenced in parallel. In one example of this type of sequencing technology, a flow cell is used that contains an optically transparent slide with eight individual lanes on the surfaces of which are bound oligonucleotide anchors (e.g., adaptor primers). A flow cell often is a solid support that is configured to retain and/or allow the orderly passage of reagent solutions over bound analytes. In some instances, flow cells are planar in shape, optically transparent, generally in the millimeter or sub-millimeter scale, and often have channels or lanes in which the analyte/reagent interaction occurs. In some embodiments, a cell-free nucleic acid sample can include a signal or tag that facilitates detection. In some such embodiments, the acquisition of sequence reads from the cell-free nucleic acid obtained from the biological sample includes obtaining quantification information of the signal or tag via a variety of techniques such as, for example, flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

In some embodiments, the first dataset comprises, for each respective subject in a first plurality of subjects of a species, corresponding first genotypic information comprising a corresponding first plurality of bin values, each respective bin value in the corresponding first plurality of bin values for a corresponding bin in a plurality of bins. In such embodiments, each respective bin in the plurality of bins represents a different and non-overlapping portion of the genome of a reference genome for the species. The bins can have the same or different sizes. Further, in such embodiments, the genotypic information for each respective subject in the first plurality of subjects comprises a first bin count for each respective bin in the first plurality of bins.

In some embodiments, genomic regions with high variability or low mappability are excluded from bin representation in the plurality of bins, for example, using the methods disclosed in Jensen et al, 2013, PLoS One 8; e57381. See also, Li and Freudenberg, 2014, Front. Genet. 5, p. 318, for analysis of mappability.

In some embodiments, bin counts are determined using any of the techniques disclosed in U.S. patent application Ser. No. 16/201,912 entitled "Models for Targeted Sequencing," filed Nov. 27, 2018 or U.S. patent application Ser. No. 16/352,214 entitled "Identifying Copy Number Aberrations," filed Mar. 13, 2019.

In some embodiments, the first bin count representative of first genotypic information is a number of fragments represented by sequence reads in sequencing information measured from cell-free nucleic acid in the biological sample that maps onto the different portion of the genome of the species represented by the respective bin. In some embodiments, such mapping allows only perfect matches. In some embodiments, such mapping allows some mismatching. In some embodiments, a program such as Bowtie 2 is used to perform such mapping. See, for example, Langmead and Salzberg, 2012, Nat Methods 9, pp. 357-359, for example disclosure on such mapping.

In some embodiments, the first bin count is determined by a number of unique nucleic acid fragments in the cell-free nucleic acid in the biological sample that map onto the different portion of the genome of the species represented by the respective bin. Depending on the sequencing method used, each such unique nucleic acid fragment may be represented by a number of sequence reads. In typical instances, this redundancy in sequence reads to unique nucleic acid fragments in the cell-free nucleic acid is resolved using multiplex sequencing techniques such as barcoding so that a bin count for a respective bin represents the number of unique nucleic acid fragments in the cell-free nucleic acid in the biological sample that map onto the different portion of the genome of the species represented by the respective bin, rather than the total number of sequence reads in the plurality of sequence reads mapping to the respective bin. See Kircher et al., 2012, Nucleic Acids Research 40, No. 1 e3, which is hereby incorporated by reference, for example disclosure on barcoding. In some such embodiments, the first bin count is in the form of B-scores, which are described, for example, in U.S. patent application Ser. No. 16/352,739, entitled "Method and System for Selecting, Managing, and Analyzing Data of High Dimensionality," filed Mar. 13, 2019, which is hereby incorporated by reference herein in its entirety.

In some embodiments, the first bin count is a number of fragments whose methylation patterns satisfy one or more filter conditions disclosed herein, such as the p-value filter of Example 5, upon generation of methylation state vectors for such fragments as disclosed, for example, in Example 10, and that map to respective bins of the plurality of bins.

In some embodiments, the sequencing data is pre-processed to correct biases or errors using one or more methods such as normalization, correction of GC biases, correction of biases due to PCR over-amplification, etc. For instance, in some embodiments, for a respective subject in the first plurality of subjects, a median bin value across the corresponding first plurality of bin values for the respective subject is obtained. Then, each respective bin value in the first plurality of bin values for the respective subject is divided by this median value thus assuring that the bin values for the respective subject are centered on a known value (e.g., on zero):

$$bv_i^* = \frac{bv_i}{\text{median}(bv_j)}$$

where,
$bv_i$=the bin value of bin i in the first plurality of bin values for the respective subject, $bv_i^*$=the normalized bin value of bin i in the first plurality of bin values for the respective subject upon this first normalization, and median($bv_j$)=the median bin value across the first plurality of unnormalized bin values for the respective subject.

In some embodiments, rather than using the median bin value across the corresponding first plurality of bin values, some other measure of central tendency is used, such as an arithmetic mean, weighted mean, midrange, midhinge, trimean, Winsorized mean, mean, or mode across the plurality of bin values of the respective subject.

In some embodiments, each respective normalized bin count $bv_i^*$ is further normalized by the median normalized value for the respective bin across the first plurality of subjects k:

$$bv_i^{**} = \log\left(\frac{bv_i^*}{\text{median}(bv_{ik}^{**})}\right)$$

where,
$bv_i^*$=the normalized bin value of bin i in the first plurality of bin values for the respective subject from the first normalization procedure described above,
$bv_i^{**}$=the normalized bin value of bin i for the respective subject upon this second normalization described here, and
median($bv_{ik}^{**}$)=the median normalized bin value $bv_i^*$ for bin i across the first plurality of subjects (k subjects).

Figure 17:
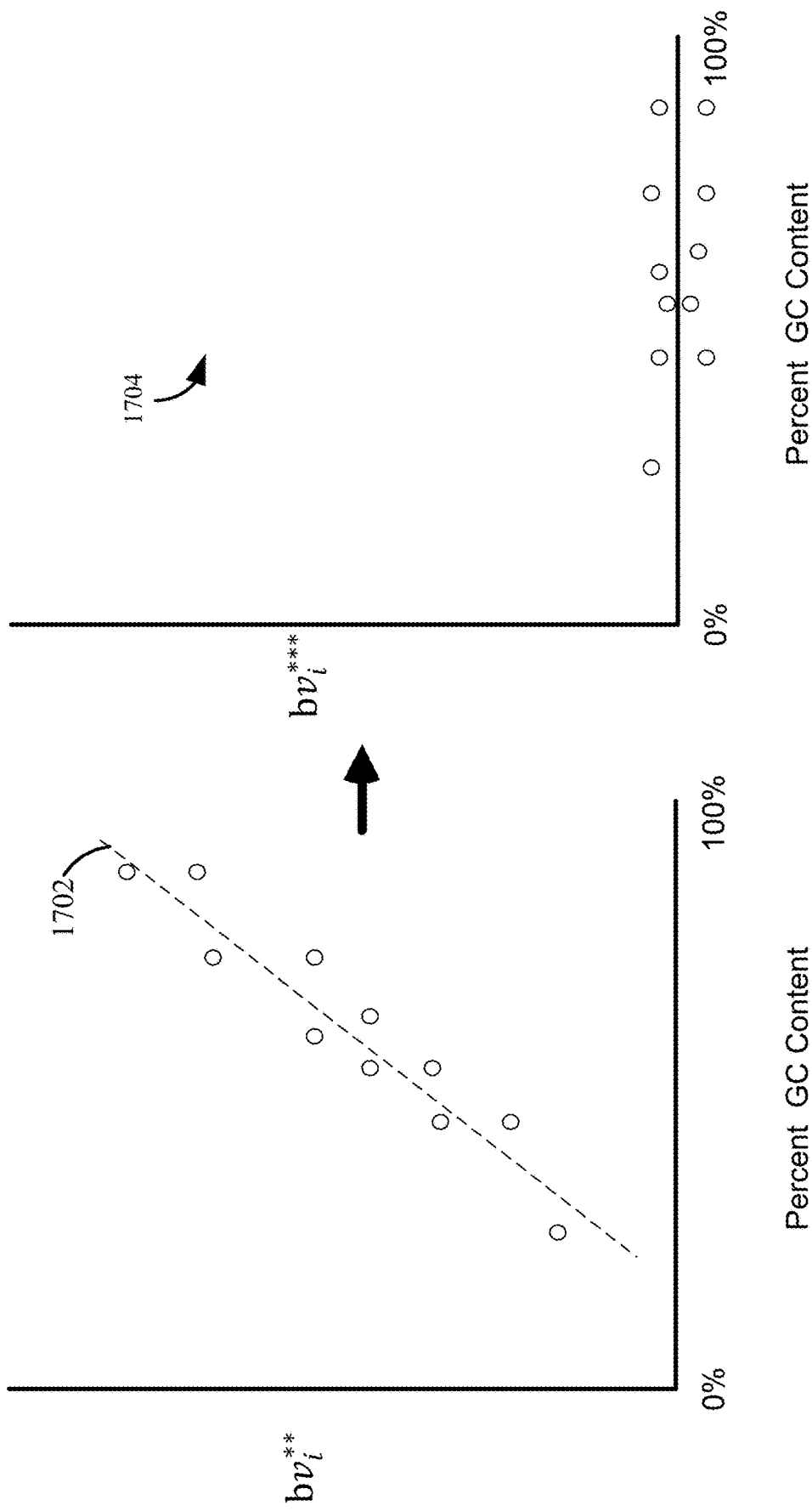
FIG. 17 illustrates GC normalization of bin counts, in accordance with the present disclosure.

In some embodiments, the un-normalized bin values $bv_i$ are GC normalized. In some embodiments, the normalized bin values $bv_i^*$ are GC normalized. In some embodiments, the normalized bin values $bv_i^{**}$ are GC normalized. In such embodiments, GC counts of respective sequence reads in the first plurality of sequence reads of each subject in the plurality of subjects are binned. A curve describing the conditional mean fragment count per GC value is estimated by such binning (Yoon et al., 2009, Genome Research 19(9):1586), or, alternatively, by assuming smoothness (Boeva et al., 2011, Bioinformatics 27(2), p. 268; Miller et al., 2011, PLoS ONE 6(1), p. e16327). The resulting GC curve determines a predicted count for each bin based on the bin's GC. These predictions can be used directly to normalize the original signal (e.g., $bv_i^*$, $bv_i$, or $bv_i^{}$). As a non-limiting example, in the case of binning and direct normalization, for each respective G+C percentage in the set {0%, 1%, 2%, 3%, ..., 100%}, the value $m_{GC}$, the median value of $bv_i^{}$ of all bins across the first plurality of subjects having this respective G+C percentage, is determined and subtracted from the normalized bin values $bv_i^{}$ of those bins having the respective G+C percentage to form GC normalized bin values $bv_i^{*}$. In FIG. 17, curve 1702 is a plot of G+C percentage versus bin value $bv_i^{}$ across the first plurality of bins across the plurality of subjects. Upon GC normalization, GC normalized bin values $bv_i^{*}$, as set forth in plot 1704 of FIG. 17, are now centered on GC content thereby removing GC bias from the bin values. In some embodiments, rather than using the median value of $bv_i^{}$ of all bins across the first plurality of subjects having this respective G+C percentage, some other form of measure of central tendency of $bv_i^{}$ of all bins across the first plurality of subjects having this respective G+C percentage is used, such as an arithmetic mean, weighted mean, midrange, midhinge, trimean, Winsorized mean, mean, or mode. In some embodiments, curve 1702 is determined using a locally weighted scatterplot smoothing model (e.g., LOESS, LOWESS, etc.). See, for example, Benjamini and Speed, 2012, Nucleic Acids Research 40(10): e72; and Alkan et al., 2009, Nat Genet 41:1061-7. For example, in some embodiments, the GC bias curve is determined by LOESS regression of count by GC (e.g., using the 'loess' R package) on a random sampling (or exhaustive sampling) of bins from the plurality of subjects. In some embodiments, the GC bias curve is determined by LOESS regression of count by GC (e.g., using the 'loess' R package), or some other form of curve fitting, on a random sampling of bins from a cohort of young healthy subjects that have been sequenced using the same sequencing techniques used to sequence the first plurality of subjects.

In some embodiments, the bin counts are normalized using principal component analysis (PCA) to remove higher-order artifacts for a population-based (healthies) correction. See, for example, Price et al., 2006, Nat Genet 38, pp. 904-909; Leek and Storey, 2007, PLoS Genet 3, pp. 1724-1735; and Zhao et al., 2015, Clinical Chemistry 61(4), pp. 608-616. Such normalization can be in addition to or instead of any of the above-identified normalization techniques. In some such embodiments, to train the PCA normalization, a data matrix comprising LOESS normalized bin counts $bv_i^{***}$ from young healthy subjects in the first plurality of subjects (or another cohort that was sequenced in the same manner as the first plurality of subjects) is used and the data matrix is transformed into principal component space thereby obtaining the top N number of principal components across the training set. In some embodiments, the top 2, the top 3, the top 4, the top 5, the top 6, the top 7, the top 8, the top 9 or the top 10 such principal components are used to build a linear regression model:

$$LM(PC_1, \ldots, PC_N)$$

Then, each bin $bv_i^{*}$ of each respective bin of each respective subject in the first plurality of subjects is fit to this linear model to form a corresponding PCA-normalized bin count $bv_i^{**}$:

$$bv_i^{**} = bv_i^{*} - \text{fit}_{LM(PC_1, \ldots, PC_N)}.$$

In other words, for each respective subject in the plurality of subjects, a linear regression model is fit between its normalized bin counts $\{bv_1^{*}, \ldots, bv_i^{*}\}$ and the top principal components from the training set. The residuals of this model serve as final normalized bin values $\{bv_1^{**}, \ldots, bv_i^{}\}$ for the respective subject. Intuitively, the top principal components represent noise commonly seen in healthy samples, and therefore removing such noise (in the form of the top principal components derived from the healthy cohort) from the bin values $bv_i^{*}$ can effectively improve normalization. See Zhao et al., 2015, Clinical Chemistry 61(4), pp. 608-616 for further disclosure on PCA normalization of sequence reads using a health population. Regarding the above normalization, it will be appreciated that all variables are standardized (e.g., by subtracting their means and dividing by their standard deviations) when necessary.

In some embodiments of the present disclosure, the human genome is under consideration. For instance, in some embodiments, the human genome is divided into roughly 30 thousand bins. Then, certain of the bins are removed from consideration using the methods disclosed in U.S. patent application Ser. No. 16/352,739, entitled "Method and System for Selecting, Managing, and Analyzing Data of High Dimensionality," filed Mar. 13, 2019, which is hereby incorporated by reference, to arrive at 23,000 bins. In such embodiments, each bin is roughly the same size, in terms of the amount of a human reference genome that corresponds to the bin.

It will be appreciated that, in instances where a bin value is a count of fragments that map to a bin, the term "bin value" refers to any form of representation of this number of nucleic fragments mapping to the given bin i, and that such bin value can be in an un-normalized (e.g., $bv_i$) or normalized form (e.g., $bv_i^*$, $bv_i^{}$, $bv_i^{*}$, $bv_i^{****}$, etc.).

In some embodiments, the plurality of bins is constructed by dividing all or a portion of a reference genome (e.g., mammalian, human, etc.) into equally sized bins, where each bin represents a unique equally sized part of the reference genome. In some embodiments, the plurality of bins is constructed by dividing all of a reference genome (e.g., mammalian, human, etc.) into equally sized bins, where each bin represents a unique equally sized part of the reference genome. In some embodiments, the plurality of bins is constructed by dividing a portion of a reference genome (e.g., mammalian, human, etc.) into equally sized bins, where each bin represents a unique equally sized part of the reference genome and the portion of the reference genome is between 1 and 22 chromosomes of the reference genome, or at least 25 percent, at least 30 percent, at least 35 percent, at least 40 percent, at least 45 percent, at least 50 percent, at least 55 percent, at least 60 percent, at least 65 percent, at least 70 percent, at least 75 percent, at least 80 percent, at least 85 percent, at least 90 percent, at least 95 percent, or at least 99 percent of the reference genome. In some such embodiments, each bin represents between 10,000 bases and 100,000 bases, between 20,000 bases and 300,000 bases, between 30,000 bases and 500,000 bases, between 40,000 bases and 1,000,000 bases between 50,000 bases and 5,000,000 bases, or between 100,000 bases and 25,000,000 bases of the reference genome.

In some embodiments, the plurality of bins is constructed by dividing all or a portion of a reference genome (e.g., mammalian, human, etc.) into equally or unequally sized bins, where each bin represents a unique part of the reference genome. In some embodiments, the plurality of bins is constructed such that at least some of regions of the human genome implicated in absence or presence of cancer (e.g., drawn from the regions identified in Examples 4, 7, 8 and/or 9) are represented by the plurality of bins whereas other regions of the reference genome are not represented by the bins. In some embodiments, the plurality of bins is constructed by dividing all of a reference genome (e.g., mammalian, human, etc.) into equally or unequally sized bins, where each bin represents a unique part of the reference genome. In some embodiments, the plurality of bins is constructed by dividing a portion of a reference genome (e.g., mammalian, human, etc.) into equally or unequally sized bins, where each bin represents a unique part of the reference genome and the portion of the reference genome is between 1 and 22 chromosomes of the reference genome, or at least 25 percent, at least 30 percent, at least 35 percent, at least 40 percent, at least 45 percent, at least 50 percent, at least 55 percent, at least 60 percent, at least 65 percent, at least 70 percent, at least 75 percent, at least 80 percent, at least 85 percent, at least 90 percent, at least 95 percent, or at least 99 percent of the reference genome. Regardless of approach, each bin represents a unique part of the reference genome. In some embodiments, particularly when the bin values for such bins represent epigenetic features of methylation data obtained from targeted sequencing for either the first or second dataset involved in transfer learning, such bins range in size between 30 bps and 5000 bps, between 30 bps and 4000 bps, between 30 bps and 3000 bps, between 30 bps and 2000 bps, between 30 bps and 1000 bps, or between 40 bps and 800 bps of the reference genome. In alternative embodiments, such bins range in size between 10,000 bps and 100,000 bps, between 20,000 bps and 300,000 bps, between 30,000 bps and 500,000 bps, between 40,000 bps and 1,000,000 bps between 50,000 bps and 5,000,000 bps, or between 100,000 bps and 25,000,000 bps of the reference genome.

In some embodiments, the plurality of bins is constructed by dividing all or a portion of a reference genome (e.g., mammalian, human, etc.) into equally or unequally sized bins, where each bin represents a corresponding part of the reference genome. In such embodiments, the corresponding part of the reference genome represented by one bin in the plurality of bins can overlap with the corresponding part of the reference genome represented by another bin in the plurality of bins. In some such embodiments, the plurality of bins is constructed by dividing all of a reference genome (e.g., mammalian, human, etc.) into equally or unequally sized bins, where each bin represents a corresponding overlapping or non-overlapping part of the reference genome. In some embodiments, the plurality of bins is constructed by dividing a portion of a reference genome (e.g., mammalian, human, etc.) into equally or unequally sized bins, where each bin represents an overlapping or non-overlapping part of the reference genome and the portion of the reference genome is between 1 and 22 chromosomes of the reference genome, or at least 25 percent, at least 30 percent, at least 35 percent, at least 40 percent, at least 45 percent, at least 50 percent, at least 55 percent, at least 60 percent, at least 65 percent, at least 70 percent, at least 75 percent, at least 80 percent, at least 85 percent, at least 90 percent, at least 95 percent, or at least 99 percent of the reference genome. In some such embodiments, each bin represents between 10,000 bases and 100,000 bases, between 20,000 bases and 300,000 bases, between 30,000 bases and 500,000 bases, between 40,000 bases and 1,000,000 bases between 50,000 bases and 5,000,000 bases, or between 100,000 bases and 25,000,000 bases of the reference genome.

In some embodiments, each of the bins represents a specific site of a reference genome that has been identified as being associated with cancer.

In some embodiments, each of the bins represents a specific region of a reference genome that has been identified as being associated with cancer through cancer- and/or tissue-specific methylation patterns in cfDNA relative to non-cancer controls. For example, Example 4 discloses 103,456 such distinct regions. Examples 7, 8, and 9 also disclose a number of distinct regions. In some embodiments, there is a one to one correspondence between such bins and these regions. In other words, in such embodiments, each bin encompasses a single unique one of the regions identified in Examples 4, 7, 8 and/or 9. In some such embodiments, each bin ranges in size between 30 bps and 5000 bps, between 30 bps and 4000 bps, between 30 bps and 3000 bps, between 30 bps and 2000 bps, between 30 bps and 1000 bps, or between 30 bps and 750 bps. In some embodiments, in the case where the regions used are drawn from Examples 4, 7, 8, and/or 9, each bin includes between 1 and 590 cytosine-guanine dinucleotides (CpGs). In some embodiments, some of the bins represent regions that are hypomethylated in the cancer-state relative to the cancer-free normal state. In some embodiments, some of the bins represent regions that are hypermethylated in the cancer-state relative to the cancer-free normal state. In some embodiments, the plurality of bins used collectively encompass at least 1000, at least 2000, at least 3000, at least 4000, at least 5000, at least 6000, at least 7000, at least 8000, at least 9000, at least 10000, at least 25000, at least 30000, at least 40000, or at least 50000 of the regions identified in Examples 4, 7, 8, and/or 9 with each bin in the plurality of bins representing a different unique region in the plurality of regions identified in Examples 4, 7, 8, and/or 9. In such embodiments, the bin value for each bin is based on a number of nucleic acid fragments, as ascertained from the corresponding first plurality of sequence reads acquired from a biological sample of a respective subject that map to the respective bin.

In some embodiments, the plurality of bins is derived from the sequences disclosed in Examples 4, 7, 8, and/or 9. In some such embodiments, adjacent and overlapping targets (genomic sequence targeted by a probe to a region of Example 4, 7, 8, and/or 9) are merged into contiguous genomic regions. In some embodiments, each of the resulting regions is used as-is as a corresponding bin in the plurality of bins if smaller than a threshold number of base pairs (e.g., 1000 base pairs), or else subdivided into sub-regions (e.g., 1000 base pair regions). It will be appreciated that the present disclosure is not limited to bins having 1000 base pair regions and that any positive integer value between 100 base pairs and 10 million base pairs can be used to define the bins. Moreover, it will be appreciated that, rather than dividing a genome by base pair values for form bins, the genome can be divided into bins based on blocks of CpG sites, such as between 1 and 1000 CpG sites per bin rather than by explicitly considering base pair lengths for such bins. In some embodiments, the bins are arranged so that consecutive bins overlap by a certain number of base pairs (e.g., in the case of 1000 base pair bins, by, for example, overlapping by 500 base pairs) which may or may not represent a certain number of CpG sites. In some embodiments, each bin ranges in size between 30 bps and 5000 bps, between 30 bps and 4000 bps, between 30 bps and 3000 bps, between 30 bps and 2000 bps, between 30 bps and 1000 bps, or between 30 bps and 750 bps.

In some embodiments, the plurality of bins is derived such that each bin encompasses one, two, three, four, five, six, seven, or eight probes described in Example 6. In some such embodiments, adjacent and overlapping targets (genomic sequence targeted by a probe of Example 6) are merged into contiguous genomic regions. In some embodiments, each of the resulting regions is used as-is as a corresponding bin in the plurality of bins if smaller than a threshold number of base pairs (e.g., 1000 base pairs), or else subdivided into sub-regions (e.g., 1000 base pair regions). It will be appreciated that the present disclosure is not limited to bins having 1000 base pair regions and that any positive integer value between 100 base pairs and 10 million base pairs can be used to define the bins. In some embodiments, the bins are arranged so that consecutive bins overlap by a certain number of base pairs (e.g., in the case of 1000 base pair bins, by, for example, overlapping by 500 base pairs). In some such embodiments, each bin ranges in size between 30 bps and 5000 bps, between 30 bps and 4000 bps, between 30 bps and 3000 bps, between 30 bps and 2000 bps, between 30 bps and 1000 bps, or between 30 bps and 750 bps.

In some embodiments, the plurality of bins is derived such that each bin encompasses a region of the genome described in Example 4. In some such embodiments, each bin ranges in size between 30 bps and 5000 bps, between 30 bps and 4000 bps, between 30 bps and 3000 bps, between 30 bps and 2000 bps, between 30 bps and 1000 bps, or between 30 bps and 750 bps.

In some embodiments, the plurality of bins is derived such that each bin encompasses a region of the genome described in Example 7. In some such embodiments, each bin ranges in size between 30 bps and 5000 bps, between 30 bps and 4000 bps, between 30 bps and 3000 bps, between 30 bps and 2000 bps, between 30 bps and 1000 bps, or between 30 bps and 750 bps.

In some embodiments, the plurality of bins is derived such that each bin encompasses a region of the genome described in Example 8. In some such embodiments, each bin ranges in size between 30 bps and 5000 bps, between 30 bps and 4000 bps, between 30 bps and 3000 bps, between 30 bps and 2000 bps, between 30 bps and 1000 bps, or between 30 bps and 750 bps.

In some embodiments, the plurality of bins is derived such that each bin encompasses a region of the genome described in Example 9. In some such embodiments, each bin ranges in size between 30 bps and 5000 bps, between 30 bps and 4000 bps, between 30 bps and 3000 bps, between 30 bps and 2000 bps, between 30 bps and 1000 bps, or between 30 bps and 750 bps.

In some embodiments, the plurality of bins is derived from any combination of the bins disclosed in Examples 4, 7, 8, or 9. In some such embodiments, each bin ranges in size between 30 bps and 5000 bps, between 30 bps and 4000 bps, between 30 bps and 3000 bps, between 30 bps and 2000 bps, between 30 bps and 1000 bps, or between 30 bps and 750 bps.

In some embodiments, each bin represents all or a portion of an enhancer, promoter, 5' UTR, exon, exon/inhibitor boundary, intron, intron/exon boundary, 3' UTR region, CpG shelf, CpG shore, or CpG island in a reference genome. See, for example, Cavalcante and Santor, 2017, "annotatr: genomic regions in context," Bioinformatics 33(15) 2381-2383, for suitable definitions of such regions and where such annotations are documented for a number of different species.

In some embodiments, a reference genome (or a subset of the reference genome) is partitioned in one or more stages, e.g., for use cases involving a targeted methylation assay. For instance, the reference genome is separated into blocks (bins) of CpG sites. As used herein, in this context, the terms "bins" and "blocks" are used interchangeably. In some such embodiments, each bin (block) is defined when there is a separation between two adjacent CpG sites that exceeds a threshold, e.g., greater than 200 base pairs (bp), 300 bp, 400 bp, 500 bp, 600 bp, 700 bp, 800 bp, 900 bp, or 1,000 bp, among other values. Thus, bins (blocks) in such embodiments can vary in size of base pairs. For each respective bin (block), the respective bin is divided into windows of a certain length, e.g., 500 bp, 600 bp, 700 bp, 800 bp, 900 bp, 1,000 bp, 1,100 bp, 1,200 bp, 1,300 bp, 1,400 bp, or 1,500 bp, among other values. In other embodiments, the windows can be from 200 bp to 10 kilobase pairs (kbp), from 500 bp to 2 kbp, or about 1 kbp in length. Windows (e.g., that are adjacent) can overlap by a number of base pairs or a percentage of the length, e.g., 10%, 20%, 30%, 40%, 50%, or 60%, among other values.

Sequence reads derived from DNA fragments are then analyzed using a windowing process in some embodiments. In particular, a sequence processor scans through the bins window-by-window and reads fragments within each window. Such windows of bins are illustrated in FIG. 23. In some embodiments, the fragments originate from tissue and/or high-signal cfDNA. High-signal cfDNA samples can be determined by a binary classification model, by cancer stage, or by another metric. By partitioning the reference genome (e.g., using bins and windows), computational parallelization if facilitated. Moreover, computational resources, to process a reference genome by targeting the sections of base pairs that include CpG sites, while skipping other sections that do not include CpG sites, are reduced. See, for example, U.S. patent application Ser. No. 15/931,022, entitled "Model Based Featurization and Classification," filed May 13, 2020, which is hereby incorporated by reference.

In some embodiments, each respective bin value in the corresponding first plurality of bin values for a corresponding bin in a plurality of bins for a respective subject is determined by identifying the number for nucleic acid fragments represented in a corresponding first plurality of sequence reads obtained from a biological sample of the respective subject, that map to the genomic region represented by the corresponding bin.

In some embodiments, each respective bin value in the corresponding first plurality of bin values for a corresponding bin in a plurality of bins for a respective subject is the number of nucleic acid fragments represented in a corresponding first plurality of sequence reads obtained from a biological sample of the respective subject, that map to the genomic region represented by the corresponding bin.

In some embodiments, each respective bin value in the corresponding first plurality of bin values for a corresponding bin in a plurality of bins for a respective subject is the number of nucleic acid fragments represented in a corresponding first plurality of sequence reads, obtained from a biological sample of the respective subject, that (i) map to the genomic region represented by the corresponding bin and (ii) satisfy one or more filter conditions. Non-limiting examples of filter conditions are provided below.

P-value filtering based on methylation vectors. In some embodiments, a filter condition in the one or more filter conditions is a requirement that each fragment have a p-value that is below a threshold value, where the p-value is determined by p-value filtering as described in Example 5. The goal of such a filter condition is to accept and use anomalously methylated fragments based on their methylation state vectors. For example, for each fragment in a sample, a determination is made as to whether the fragment is anomalously methylated (via analysis of sequence reads derived therefrom), relative to an expected methylation state vector from a healthy sample using the methylation state vector corresponding to the fragment. In some embodiments, the p-value for each methylation state vector describing a probability of observing that methylation state vector or other methylation state vectors even less probable in the healthy control group (as described, for example, in U.S. Pat. Appl. Pub. No. 2019/0287652, which is incorporated herein by reference), is calculated. The process for calculating a p-value is discussed in Example 5. In some embodiments, the threshold value is 0.01 (e.g., p must be <0.01 in such embodiments, as determined by the methods described in Example 5, in such embodiments). In some embodiments, the threshold is 0.001, 0,005, 0.01, 0.015, 0.02, 0.05, or 0.10. In some embodiments, the threshold is between 0.0001 and 0.20. In such embodiments, only those fragments that have a p-value below the threshold value contribute to bin count. In some embodiments, a Markov model (e.g., a Hidden Markov Model "HMM") is used to determine the probability that a sequence of methylation states (comprising, e.g., "M" or "U") will be observed for each respective fragment represented by the plurality of sequence reads, given a set of probabilities that determine, for each state in the nucleic acid sequence of the respective fragment, the likelihood of observing the next state in the sequence. In some embodiments, the set of probabilities are obtained by training the HMM. Such training involves computing statistical parameters (e.g., the probability that a first state will transition to a second state (the transition probability) and/or the probability that a given methylation state will be observed for a respective CpG site (the emission probability)), given an initial training dataset of observed methylation state sequences (e.g., methylation patterns) obtained from a cohort of non-cancer subjects. In some embodiments, the HMM is trained using supervised training (e.g., using samples where the underlying sequence as well as the observed states are known). In some alternative embodiments, the HMM is trained using unsupervised training (e.g., Viterbi learning, maximum likelihood estimation, expectation-maximization training, and/or Baum-Welch training). For example, an expectation-maximization algorithm such as the Baum-Welch algorithm estimates the transition and emission probabilities from observed sample sequences and generates a parameterized probabilistic model that best explains the observed sequences. Such algorithms iterate the computation of a likelihood function until the expected number of correctly predicted states is maximized. See, e.g., Yoon, 2009, "Hidden Markov Models and their Applications in Biological Sequence Analysis," Curr. Genomics. September; 10(6): 402-415, doi: 10.2174/138920209789177575. See also Example 5 for additional discussion of Markov models.

Figure 18:
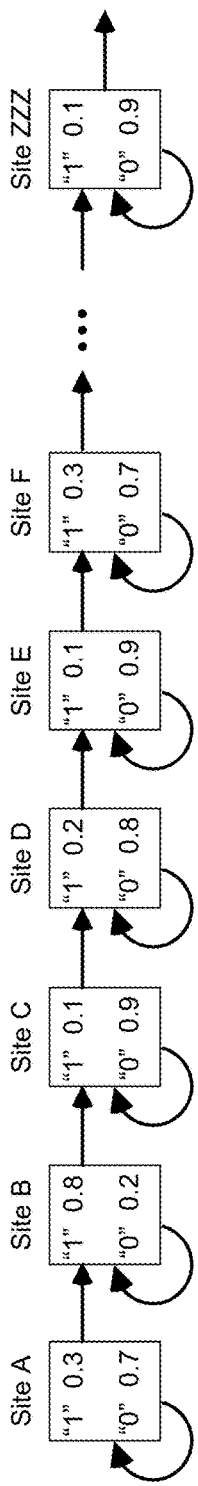
FIG. 18 illustrates the use of a p-value cutoff to select certain fragments for contribution to bin counts, where the p-value is computed using a Markov model trained using the methylation fragments of a cohort of non-cancer subjects, in accordance with an aspect of the present disclosure.

FIG. 18 illustrates the filtering of fragments represented by a plurality of sequence reads obtained from a subject by removing each represented fragment that fails to satisfy a p-value threshold, in accordance with some embodiments of the present disclosure. The filter is applied to the methylation pattern of each respective fragment represented by the respective first plurality of sequence reads of a corresponding subject, using the methylation patterns observed across a training population of non-cancer subjects such as disclosed in Example 5. Each respective methylation pattern of each respective fragment (e.g., Fragment One, . . . , Fragment N) comprises a corresponding one or more methylation sites (e.g., CpG sites) identified with a methylation site identifier and a corresponding methylation pattern, represented as a sequence of 1's and 0's, where each "1" represents a methylated CpG site in the one or more CpG sites and each "0" represents an unmethylated CpG site in the one or more CpG sites. The methylation patterns observed across the fragments of the non-cancer training population, such as disclosed in Example 5, are used to build a methylation state distribution for the CpG site states collectively represented by the fragments of the non-cancer training population (e.g., CpG site A, CpG site B, CpG site ZZZ).

As depicted in FIG. 18, transition probabilities between states for a Hidden Markov Model (HMM) are represented by the arrows in the illustration, and can be determined using the methylation state distribution for the CpG site states (e.g., using an expectation-maximization algorithm such as the Baum-Welch algorithm), thereby training the HMM. For each respective fragment represented by the respective plurality of sequence reads of a subject, the trained HMM is used to determine the likelihood of occurrence of the methylation pattern of the respective fragment (e.g., using a forward algorithm). Fragments whose likelihoods of occurrence fail to satisfy a first threshold value of the first threshold filter (e.g., their methylation patterns are too common among the fragments in the reference population) are discarded (e.g., do not contribute to bin count).

Minimum bag-size. In some embodiments, a filter condition in the one or more filter conditions is a requirement that each fragment have a bag-size greater than a threshold integer. In other words, that each fragment be represented by more than the threshold integer of sequence reads in the plurality of sequence reads. For example, in the case where the threshold integer is one, each fragment must be represented by more than one sequence read in the plurality of sequence reads. In some embodiments, the threshold integer is 1, 2, 3, 4, 5, 6, 7, 8, 9, 10, or an integer between 10 and 100.

Minimum number of CpG sites. In some embodiments, a filter condition in the one or more filter conditions is a requirement that each fragment cover a first threshold number of CpG sites and be less than a second threshold length in terms of base pairs. For example, in the case where the first threshold is 1 CpG site and the second threshold 1000 base pairs, each fragment must cover more than one CpG site and be less than 1000 base pairs in length. In some embodiments, each fragment must cover at least 1, 2, 3, 4, 5, 6, 7, 8, 9 or 10 CpG sites. In some embodiments, each fragment must be less than 1 thousand, 2 thousand, 3 thousand, or 4 thousand contiguous base pairs in length.

Hypermethylation or Hypomethylation. In some embodiments, a filter condition in the one or more filter conditions is a requirement that each fragment is hypermethylated. In some embodiments, a filter condition in the one or more filter conditions is a requirement that each fragment is hypomethylated. In some embodiments, the filter condition is bin dependent. For instance, International Patent Publication No. WO2019/195268, entitled "Methylation Markers and Targeted Methylation Probe Panels," filed Apr. 2, 2019, which is hereby incorporated by reference, discloses a number of regions of the human genome that have a hypermethylated state that is associated with one or more cancer conditions as well as a number of regions of the human genome that have a hypomethylated that is associated with one or more cancer conditions. Accordingly, in some embodiments of the present disclosure one or more bins in the plurality of bins each represent a corresponding genomic region in the regions disclosed in WO2019/19528 and the filter condition in the one or more filter conditions (a) requires selection of fragments that are hypermethylated when selecting fragments that map to a bin representing a region of the human genome that has a hypermethylated state that is associated with one or more cancer conditions of CpG sites as indicated by WO2019/195268 and (b) requires selection of fragments that are hypomethylated when selecting fragments that map to a bin representing a region of the human genome that has a hypomethylated state that is associated with one or more cancer conditions of CpG sites as indicated by WO2019/195268.

As another example, International Application No. PCT/US2020/015082, entitled "Detecting Cancer, Cancer Tissue or Origin, or Cancer Type," filed Jan. 24, 2020, which is hereby incorporated by reference, also discloses a number of regions of the human genome that have a hypermethylated state that is associated with one or more cancer conditions as well as a number of regions of the human genome that have a hypomethylated that is associated with one or more cancer conditions. Accordingly, in some embodiments of the present disclosure one or more bins in the plurality of bins each represent a corresponding genomic region in the regions disclosed in International Application No. PCT/US2020/015082 and the filter condition in the one or more filter conditions (a) requires selection of fragments that are hypermethylated when selecting fragments that map to a bin representing a region of the human genome that has a hypermethylated state that is associated with one or more cancer conditions of CpG sites as indicated by International Application No. PCT/US2020/015082 and (b) requires selection of fragments that are hypomethylated when selecting fragments that map to a bin representing a region of the human genome that has a hypomethylated state that is associated with one or more cancer conditions of CpG sites as indicated by International Application No. PCT/US2020/015082. In some embodiments, the one or more filter conditions require the p-value threshold is satisfied and that fragment is hypermethylated. In some embodiments, the one or more filter conditions require the p-value threshold is satisfied and that fragment is hypomethylated. In some embodiments, the one or more filter conditions are different for each bin. For instance, for one bin in the plurality of bins, the one or more filter conditions require the p-value threshold is satisfied and that fragment is hypomethylated, while for a second bin in the plurality of bins, the one or more filter conditions require the p-value threshold is satisfied and that fragment is hypermethylated In some embodiments, any combination of the disclosed filter conditions is imposed. For example, in some embodiments, each respective bin value in the corresponding first plurality of bin values for a corresponding bin in a plurality of bins for a respective subject is the number of nucleic acid fragments represented in a corresponding first plurality of sequence reads, obtained from a biological sample of the respective subject, that (i) map to the genomic region represented by the corresponding bin (ii) have a p-value less than 0.01 upon application of the methylation pattern to a trained Markov model, (iii) have a bag-size greater than one, (iv) covers at least 1 CpG site, and (v) is less than 1000 base pairs in length. While discussion of filter conditions have been presented in relation to the subjects of a first dataset that is used in transfer learning (i.e., application to the subjects of a second dataset), it will be appreciated that application of such filter conditions is typically applied to both the subjects in the training dataset (the first dataset) and the dataset that is subjected to transfer learning (the second dataset). In some embodiments, the filter conditions that are applied to the fragments of the first dataset are different than the filter conditions that are applied to the fragments of the second dataset.

Bin overlap. In some embodiments, when a fragment overlaps multiple bins, it is assigned (contributes to the count) in each bin it overlaps. In some embodiments, when a fragment overlaps multiple bins, it is assigned (contributes to the count) of the bin it overlaps the most.

Referring back to FIG. 10A, with reference to block 1003, each feature extraction function in the first plurality of feature extraction functions independently encodes a linear or nonlinear function of bin value of all or a subset of the plurality of bins in the form of an independent weight for each respective bin in the plurality of bins or the subset of the plurality of bins.

In some embodiments, as discussed above, each feature extraction function in the first plurality of feature extraction functions (obtained using the first dataset) can be a feature extraction function that is a linear or nonlinear function. An example of a nonlinear feature extraction function (which can be applied to, e.g., the second dataset) is:

Feature Extraction Function $1 = A^*([\text{bin count of bin } B]^*[\text{bin count of bin } C]) + E^*(\text{bin count of bin } F)$, where A and E are weights that each take the form of a real positive or negative value, and B, C, and F are bins in the plurality of bins.

An example of a linear feature extraction function (which can be applied to, e.g., the second dataset) is:

Feature Extraction Function $2 = G^*[\text{bin count of bin } H] + I^*[\text{bin count of bin } J] + K^*(\text{bin count of bin } L)$, where G, I, and K are weights that each take the form of a real positive or negative value, and H, J, and L are bins in the plurality of bins.

Of course, the above example are feature extraction functions in which only a few bins have been specified. In practice, the feature extraction functions specify many more bins than the few exemplified here. For instance, in some embodiments, bin values and weights for 50, 100, 200, 1000, or 2000 or more bins or combinations thereof are specified by a feature extraction function. In some embodiments, bin values and weights for at least ten percent, twenty percent, forty percent, sixty percent, eighty-five percent or all of the applicable bins are specified by a feature extraction function. In such embodiments, some of the bins have zero weight.

A feature (also referred to herein as a feature value) that is obtained using a feature extraction function can be the computational result of inputting the bin counts (from the second dataset) into that feature extraction function. For example, continuing with the simplified example above, an example of a feature, such as Feature 2-1 for subject 2-1 of the second dataset, extracted using Feature Extraction Function 1 can be:

Feature $2\text{-}1 = A \times [\text{bin count of bin } B \text{ for subject } 2\text{-}1]^* [\text{bin count of bin } C \text{ for subject } 2\text{-}1] + E^*(\text{bin count of bin } F \text{ for subject } 2\text{-}1)$.

In some embodiments, the feature values collectively determine a vector for the subject. For example, in embodiments in which each feature extraction function is a principal component, each feature value includes the bin values projected onto the particular principal component.

In some embodiments, as shown at block 1004, the cancer condition set comprises three or more cancer conditions. For each respective cancer condition in the cancer condition set, there are two or more subjects in the first plurality of subjects that have the respective cancer condition, and for each respective pair of cancer conditions in the cancer condition set, the applying the first feature extraction technique is performed by applying an instance of the first feature extraction technique to the respective bin values of respective subjects in the first dataset that have either a first cancer condition or a second cancer condition in the respective pair of cancer conditions. Each instance of the first feature extraction technique contributes a corresponding subset of the first plurality of feature extraction functions to the first plurality of feature extraction functions. The cancer condition set can consist of at least five, or at least ten, or at least 20 unique cancer conditions. In some embodiments, the cancer condition set consists of 22 unique cancer conditions. The cancer condition set can include any suitable number of unique cancer conditions. In some embodiments, each corresponding subset of the first plurality of feature extraction functions consists of between four and one hundred feature extraction functions.

The first feature extraction technique can involve any suitable technique. For example, with reference to block 1006, in some embodiments, the applying the first feature extraction technique comprises applying a dimension reduction algorithm to the subjects in the first dataset that have either a first cancer condition or a second cancer condition in the respective pair of cancer conditions thereby identifying the corresponding subset of the first plurality of feature extraction functions. In some embodiments, once the subsets contributing to the first plurality of feature extraction functions are combined, the first plurality of feature extraction functions can be between 500 and 20,000 functions, between 500 and 15,000 functions, between 500 and 10,000 functions, between 500 and 5,000 functions, between 500 and 4,000 functions, between 500 and 3,000 functions, between 500 and 2,000 functions, or between 500 and 1,000 functions. In some embodiments, the first plurality of feature extraction functions can include fewer than 500 functions, fewer than 200 functions, or even fewer than 100 functions. Furthermore, in some embodiments, each corresponding subset of the first plurality of feature extraction functions has a smaller number of functions—e.g., it consists of between 2 and 100 feature extraction functions. In such embodiments, methods focusing on classification a limited number of cancers (e.g., a specific cancer type) can include a small number of feature extraction functions.

Figure 10B:
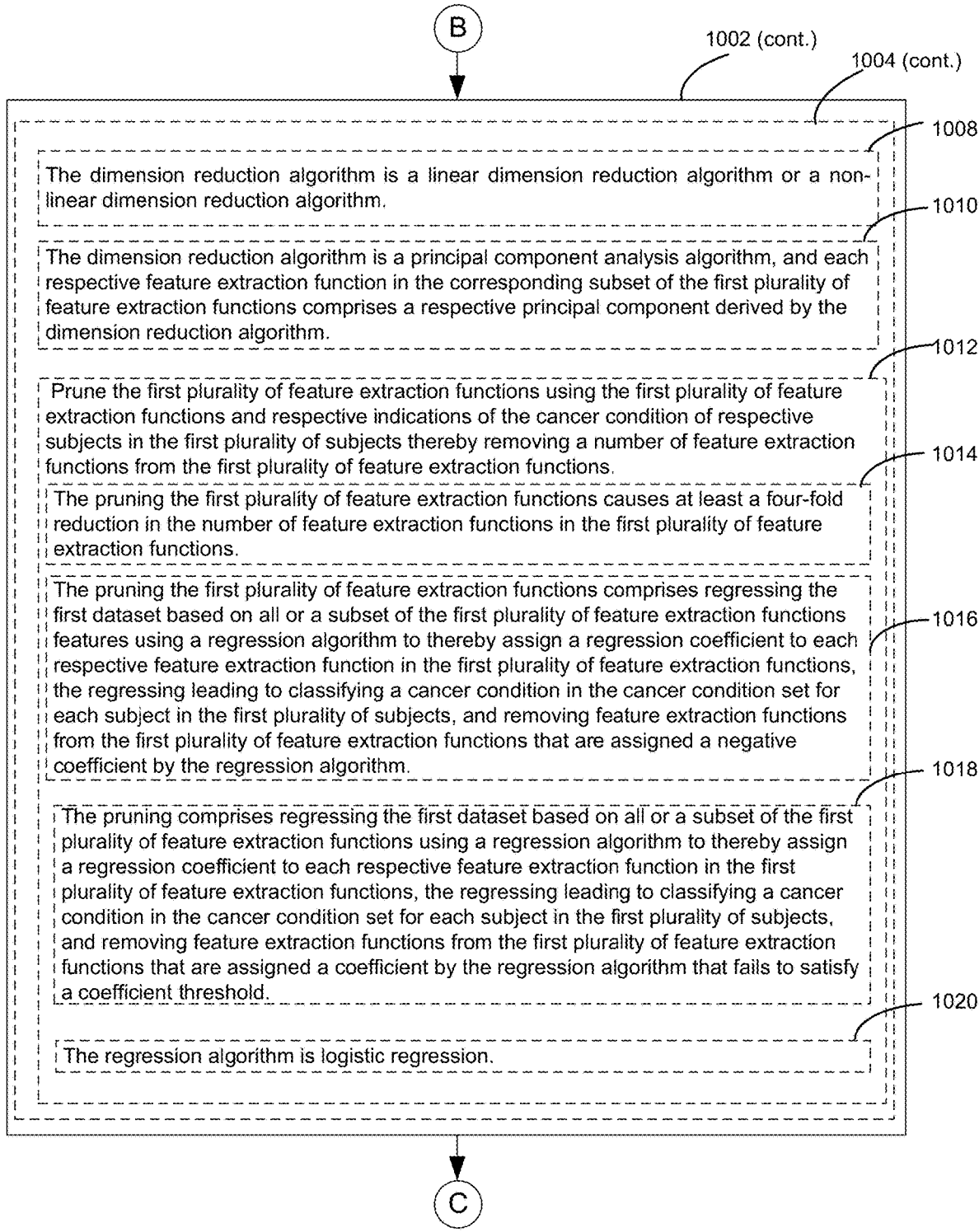

The dimension reduction algorithm can be a linear dimension reduction algorithm or a non-linear dimension reduction algorithm, as shown at block 1008 of FIG. 10B. In some embodiments, the dimension reduction algorithm is principal component analysis algorithm, a factor analysis algorithm, Sammon mapping, curvilinear components analysis, a stochastic neighbor embedding (SNE) algorithm, an Isomap algorithm, a maximum variance unfolding algorithm, a locally linear embedding algorithm, a t-SNE algorithm, a non-negative matrix factorization algorithm, a kernel principal component analysis algorithm, a graph-based kernel principal component analysis algorithm, a linear discriminant analysis algorithm, a generalized discriminant analysis algorithm, a uniform manifold approximation and projection (UMAP) algorithm, a LargeVis algorithm, a Laplacian Eigenmap algorithm, or a Fisher's linear discriminant analysis algorithm. See, for example, Fodor, 2002, "A survey of dimension reduction techniques," Center for Applied Scientific Computing, Lawrence Livermore National, Technical Report UCRL-ID-148494; Cunningham, 2007, "Dimension Reduction," University College Dublin, Technical Report UCD-CSI-2007-7, Zahorian et al., 2011, "Nonlinear Dimensionality Reduction Methods for Use with Automatic Speech Recognition," Speech Technologies. doi:10.5772/16863. ISBN 978-953-307-996-7; and Lakshmi et al. (18 Aug. 2016). 2016 IEEE 6th International Conference on Advanced Computing (IACC). pp. 31-34. doi:10.1109/IACC.2016.16, ISBN 978-1-673-8286-1, each of which is hereby incorporated by reference. Accordingly, with reference to block 1010, in some embodiments, the dimension reduction algorithm is a principal component analysis (PCA) algorithm, and each respective feature extraction function in the corresponding subset of the first plurality of feature extraction functions comprises a respective principal component derived by the PCA. In such embodiments, the corresponding subset of the first plurality of feature extraction functions can be limited to a threshold number of principal components calculated by the PCA algorithm. The threshold number of principal components can be, for example, 50, 100, 1000, 1500, or any other number. In some embodiments, each principal component calculated by the PCA algorithm is assigned an eigenvalue by the PCA algorithm, and the corresponding subset of the first plurality of feature extraction functions is limited to the threshold number of principal components assigned the highest eigenvalues.

In some embodiments, with reference to block 1012, the described techniques involve pruning the first plurality of feature extraction functions using the first plurality of feature extraction functions and respective indications of the cancer condition of respective subjects in the first plurality of subjects, thereby removing a number of feature extraction functions from the first plurality of feature extraction functions. Computational techniques (e.g., regularized regression/regularized logistic regression, etc.) are used to determine which features are more informative for the purposes of discriminating between different types of cancer using the described approach. In this way, a number of the first plurality of feature extraction functions is reduced, as also shown at block 208 of FIG. 2.

The pruning causes a certain degree of reduction in the number of feature extraction functions in the first plurality of feature extraction functions. For example, with reference to block 1014, the pruning can cause at least a four-fold reduction in the number of feature extraction functions in the first plurality of feature extraction functions. In some embodiments, the pruning can result in at least 6-, at least 7-, or at least 8-fold reduction. For example, in an embodiment, the first plurality of feature extraction functions can have 50 features per each cancer condition pair, and pruning can result in 6 or 7 features. Such pruning advantageously enriches the dataset (reduces sparsity), and further reduces the dataset which serves to improve efficiency and concomitantly reduces the amount of computer resources needed to handle the dataset.

Accordingly, in some embodiments, the pruning of the first plurality of feature extraction functions comprises regressing the first dataset based on all or a subset of the first plurality of feature extraction functions using a regression algorithm, to thereby assign a regression coefficient to each respective feature extraction function in the first plurality of feature extraction functions. The regressing can lead to classifying a cancer condition in the cancer condition set for each subject in the first plurality of subjects. Regression coefficients, which can have positive or negative values, assigned to each feature extraction function can be used to determine which feature extraction function of the first plurality of feature extraction functions to keep for further processing. For example, with reference to block 1016, in some implementations, feature extraction functions that are assigned a negative coefficient by the regression algorithm can be removed.

In some embodiments, with reference to block 1018, the pruning using a regression algorithm involves assigning a regression coefficient to each respective feature extraction function in the first plurality of feature extraction functions, such that feature extraction functions that are assigned a coefficient that fails to satisfy a certain coefficient threshold are removed.

In some embodiments, applying a regression algorithm comprises splitting the first dataset into a plurality of sets, where each set in the plurality of sets includes two or more subjects that are afflicted with a first cancer condition and two or more subjects that are afflicted with a second cancer condition, independently regressing each respective set in the plurality of sets based on all or a subset of the first plurality of feature extraction functions across the subjects of the respective set against the respective indication of cancer condition across the subject of the respective set using a regression algorithm to thereby assign a corresponding regression coefficient, in a plurality of regression coefficients, to each respective feature in the first plurality of feature extraction functions. Further, the features in the first plurality of feature extraction functions that are assigned a coefficient that satisfies a coefficient threshold for at least a threshold percentage of the plurality of sets. The plurality of sets can consist of between five and fifty sets, ten sets, or any other number of sets. The coefficient threshold can be zero or it can be greater than zero.

The regression algorithm can be any type of regression. For example, in some embodiments, with reference to block 1020 of FIG. 10B, the regression algorithm is logistic regression. Logistic regression algorithms are disclosed in Agresti, *An Introduction to Categorical Data Analysis*, 1996, Chapter 5, pp. 103-144, John Wiley & Son, New York, which is hereby incorporated by reference. In some embodiments, the logistic regression assumes:

$$P(x_i) = \frac{\exp(\beta_0 + \beta_1 x_{i1} + \ldots + \beta_k x_{ik})}{1 + \exp\exp(\beta_0 + \beta_1 x_{i1} + \ldots + \beta_k x_{ik})},$$

where, $x_i=(x_{i1}, x_{i2}, \ldots, x_{ik})$ are the corresponding plurality of feature values for the $i^{th}$ corresponding subject 126/134, where the $i^{th}$ corresponding subject has either a first cancer condition (Y=1) or a second cancer condition (Y=0);

$Y \in \{0, 1\}$ is a class label that has the value "1" when the corresponding subject i has the first cancer condition and has the value "0" when the corresponding subject i has the second cancer condition, $\beta_0$ is an intercept, and $\beta_j=(j=1, \ldots k)$ is a plurality of regression coefficients, where each respective regression coefficient in the plurality of regression coefficients is for a corresponding feature extraction function in the first plurality of feature extraction functions.

In some embodiments, the logistic regression is logistic least absolute shrinkage and selection operator (LASSO) regression. In such embodiments, the logistic LASSO estimator $\widehat{\beta_0}, \ldots, \widehat{\beta_k}$ is defined as the minimizer of the negative log likelihood:

$$\min(\Sigma_{i=1}^n[-y_i(\beta_0+\beta_1 x_i+ \ldots +\beta_k x_{ik})+\log(1+\exp(\beta_0+\beta_1 x_i+ \ldots +\beta_k x_{ik}))]),$$

subject to the constraint $\Sigma_{j=1}^k |\beta_j| \leq \lambda$, where $\lambda$ is a constant optimized for any given dataset.

In some embodiments, the regression algorithm is logistic regression with L1 or L2 regularization.

As noted in the above equations, each $x_i=(x_{i1}, x_{i2}, \ldots, x_{ik})$ are the corresponding plurality of feature values for the $i^{th}$ corresponding subject and, as such, each $x_i$ represents a corresponding feature extraction function. Moreover, each $\beta_j=(j=1, \ldots k)$ is the regression coefficient for a corresponding feature extraction function. In some embodiments, those feature extraction functions that have a corresponding regression coefficient that fails to satisfy a threshold value are pruned (removed from) the plurality of feature extraction functions. In some embodiments, this threshold value is zero. Thus, in such embodiments, those feature extraction functions that have a corresponding regression coefficient that is zero from the above-described regression are removed from the plurality of feature extraction functions prior to training the classifier. In some embodiments, the threshold value is 0.1. Thus, in such embodiments, those feature extraction functions that have a corresponding regression coefficient whose absolute value is less than 0.1 from the above-described regression are removed from the plurality of feature extraction functions prior to training the classifier. In some embodiments, the threshold value is a value between 0.1 and 0.3. An example of such embodiments is the case where the threshold value is 0.2. In such embodiments, those feature extraction functions that have a corresponding regression coefficient whose absolute value is less than 0.2 from the above-described regression are removed from the plurality of feature extraction functions prior to training the classifier.

While the above equations are with reference to just two cancer conditions, it will be appreciated that they can be pairwise applied to more than two cancer conditions. For instance, consider the case in which there are three cancer conditions, A, B, and C. As such, there are three unique pairs to be evaluated: A versus B, A versus C, and B versus C. It will be recollected that in such embodiments where there are multiple pairs of cancer conditions, the feature extraction can likewise be done in a pairwise fashion. Thus, in some embodiments where there are multiple cancer conditions and the feature extraction functions were deduced on a pairwise basis, the pruning may also occur on a pairwise basis, where each pruning only operates to prune from the subset of feature extraction functions that were obtained for a given pair of cancer conditions. For example, in the case where there are three cancer conditions A, B, and C, the pruning for those feature extraction functions obtained for A versus B can take the form:

$$P(x_i) = \frac{\exp(\beta_0 + \beta_1 x_{i1} + \ldots + \beta_k x_{ik})}{1 + \exp\exp(\beta_0 + \beta_1 x_{i1} + \ldots + \beta_k x_{ik})},$$

where, $x_i=(x_{i1}, x_{i2}, \ldots, x_{ik})$ are the corresponding plurality of feature values for the $i^{th}$ corresponding subject 126/134, where the $i^{th}$ corresponding subject has either a cancer condition A (Y=1) or cancer condition B (Y=0);

$Y \in \{0, 1\}$ is a class label that has the value "1" when the corresponding subject i has the cancer condition A and has the value "0" when the corresponding subject i has cancer condition B, $\beta_0$ is an intercept, and $\beta_j=(j=1, \ldots, k)$ is a plurality of regression coefficients, where each respective regression coefficient in the plurality of regression coefficients is for a corresponding feature extraction function in the subset of the first plurality of feature extraction functions, where each feature extraction function in the subset of functions was obtained by dimension reduction using the set of subjects that has cancer condition A or B. In some embodiments, the logistic regression is logistic least absolute shrinkage and selection operator (LASSO) regression. In such embodiments, the logistic LASSO estimator $\widehat{\beta_0}, \ldots, \widehat{\beta_k}$ is defined as the minimizer of the negative log likelihood:

$$\min(\Sigma_{i=1}^n[-y_i(\beta_0+\beta_1 x_i+ \ldots +\beta_k x_{ik})+\log(1+\exp(\beta_0+\beta_1 x_i+ \ldots +\beta_k x_{ik}))]),$$

subject to the constraint $\Sigma_{j=1}^k |\beta_j| \leq \lambda$, where $\lambda$ is a constant optimized for any given dataset.

Here, each $x_i=(x_{i1}, x_{i2}, \ldots, x_{ik})$ is the corresponding subset of the plurality of feature values for the $i^{th}$ corresponding subject and, as such, each $x_i$ represents a corresponding feature extraction function. Moreover, each $\beta_j$ ($j=1, \ldots k$) is the regression coefficient for a corresponding feature extraction function. In some embodiments, those feature extraction functions that have a corresponding regression coefficient that fails to satisfy a threshold value are pruned (removed from) the plurality of feature extraction functions. Such regression is likewise repeated for the other pairs of cancer conditions to prune the subject of feature extraction functions associated with their cancer conditions. In this way, a final set of feature extraction functions is culled together from the analysis of each pair of cancer conditions. For instance, the feature extraction functions for A versus B that survey pruning, the feature extraction functions for A versus C that survey pruning, and so forth.

While the determination of feature extraction functions can be determined and pruned on a pairwise basis, the present disclosure is not so limited. In some alternative embodiments, the determination of feature extraction functions and subsequent pruning is performed on a multivariate basis instead of a pairwise basis.

Data Blocks 1022-1044

Figure 10C:
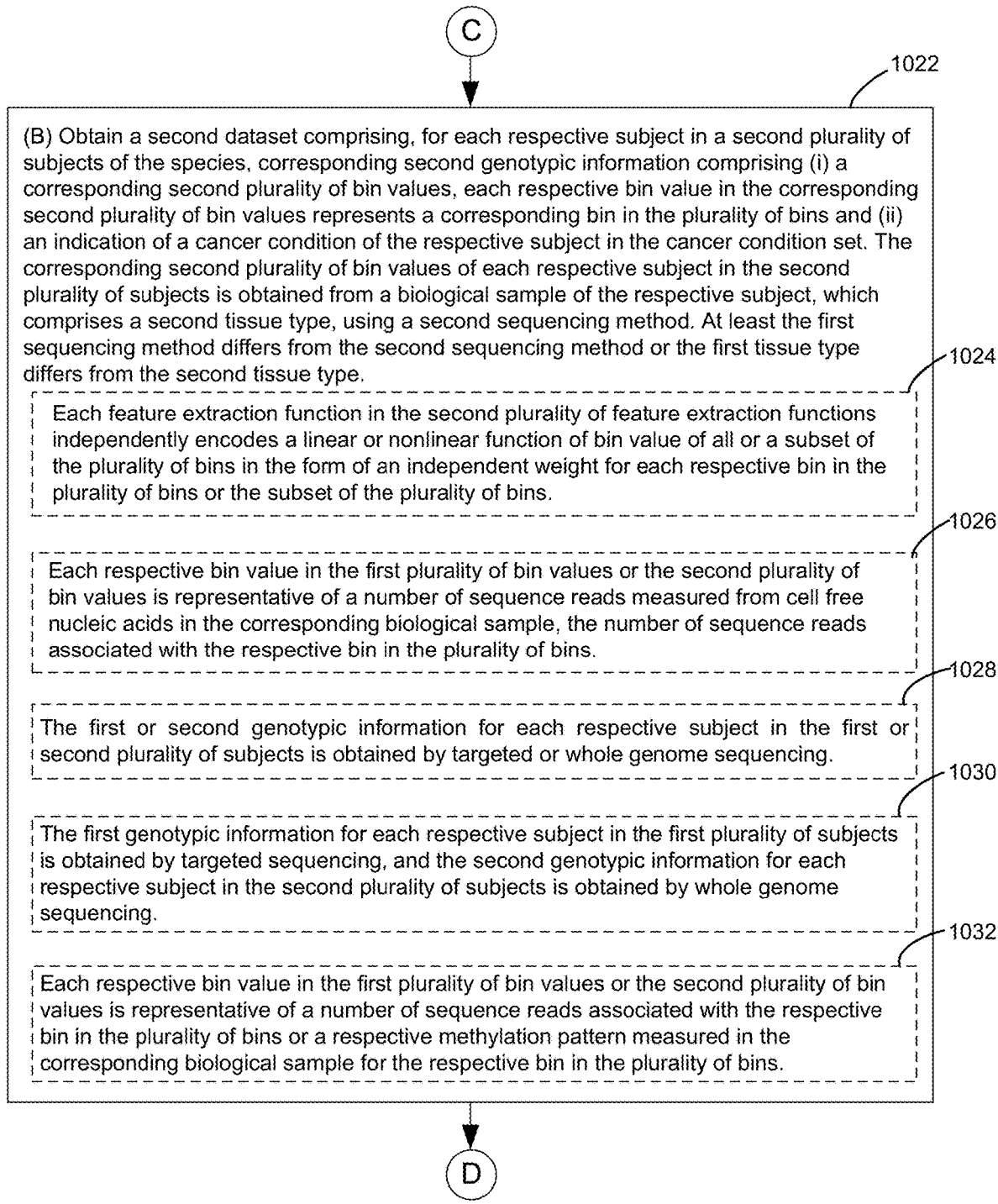

In some embodiments, with reference to block 1022 of FIG. 10C, a second dataset 124 is obtained that comprises, for each respective subject in a second plurality of subjects of the species, corresponding second genotypic information. The second genotypic information (e.g., 134-2-1, . . . , 134-1-T) comprises, as shown schematically in an example of the second dataset of FIG. 3, (i) a corresponding second plurality of bin values, each respective bin value in the corresponding second plurality of bin values represents a corresponding bin in the plurality of bins, and (ii) an indication of a cancer condition of the respective subject in the cancer condition set. The corresponding second plurality of bin values of each respective subject in the second plurality of subjects is obtained from a biological sample of the respective subject, as shown by way of example with reference to FIG. 2 (second dataset 124 is obtained from biological samples 224).

As discussed above (block 1002) in connection with the first dataset (e.g., in some embodiments, a TCGA dataset), the corresponding first plurality of bin values of each respective subject in the first plurality of subjects is obtained from a biological sample obtained from that subject, where the sample comprises a first tissue type, using a first sequencing method. In the illustrated embodiments of the present disclosure, the biological sample of the respective subject in the second plurality of subjects comprises a second tissue type, and the second plurality of bin values of each respective subject are obtained using a second sequencing method. Thus, in the some embodiments, at least the first sequencing method differs from the second sequencing method, or the first tissue type differs from the second tissue type. For example, in some embodiments, the second dataset is a CCGA dataset. However, it should be appreciated that embodiments in accordance with the present disclosure are not limited to any specific first and second datasets, or to any specific cancer conditions. Moreover, in some embodiments the first and second datasets are obtained by the same sequencing method. In some embodiments, the bin values in the second dataset are normalized in the same manner that the bins values in the first dataset were normalized. Moreover, in some embodiments, it will be appreciated that all variables are standardized (e.g., by subtracting their means and dividing by their standard deviations) when necessary. In some embodiments, the first dataset is fragment copy number counts obtained by targeted or whole genome sequencing whereas the second dataset is abnormal methylation fragment count as determined, for example by Examples 5 and 10 in conjunction with any combination of the one or more fragment filters disclosed herein such as the p-value filter relative to a non-cancer cohort.

In some embodiments, with reference to block 1024, each feature extraction function in the second plurality of feature extraction functions independently encodes a linear or non-linear function of bin value of all or a subset of the plurality of bins in the form of an independent weight for each respective bin in the plurality of bins or the subset of the plurality of bins.

The bin values in the first plurality of bin values of the first genotyping information in the first dataset and the second plurality of bin values of the second genotyping information in the second dataset can be obtained in a number of various ways. For example, in some embodiments, with reference to block 1026, each respective bin value in the first plurality of bin values or the second plurality of bin values is representative of a number of cell free fragments measured in the corresponding biological sample that map to a respective bin in the plurality of bins.

In some embodiments, the first or second genotypic information for each respective subject in the first or second plurality of subjects is obtained by targeted or whole genome sequencing, with reference to block 1028. The targeted or whole genome sequencing comprises regular non-methylation sequencing or methylation sequencing (e.g., based on bisulfite conversion or enzymatic conversion of CpG sites). In some embodiments, this whole genome sequencing is used to sequence a portion of the genome. In some embodiments this portion of the genome is at least 10 percent, 20 percent, 30 percent, 40 percent, 50 percent, 60 percent, 70 percent, 80 percent, 90 percent, 95 percent, 99 percent, 99.9 percent or all of a genome. In some embodiments, the whole genome sequencing obtains sequence reads having a sequence length of 1000 base pairs or less with a coverage of the portion of the genome that is at least 5×, at least 10×, at least 15×, at least 20×, at least 25×, at least 30×, or at least 50× across the portion of the genome. In some embodiments, the whole genome sequencing obtains sequence reads has a coverage of at least 5×, at least 10×, at least 15×, at least 20×, at least 25×, at least 30×, at least 50×, or at least 100× across the entire genome.

In some embodiments, the first genotypic information for each respective subject in the first plurality of subjects is obtained by targeted sequencing, and the second genotypic information for each respective subject in the second plurality of subjects is obtained by whole genome sequencing, as shown at block 1030. Alternatively, in some embodiments, the first genotypic information is obtained by whole genome sequencing, and the second genotypic information is obtained by targeted sequencing. In some embodiments, a plurality of nucleic acid probes is used in the targeted nucleic acid sequencing. In some embodiments, these probes map onto the regions identified in Example 4. In some embodiments, at least 1000 probes, each mapping to a different unique location in the human reference genome are used. In some embodiments, at least 3000 probes, at least 4000 probes, at least 5000 probes, at least 6000 probes, at least 7000 probes, at least 8000 probes, at least 9000 probes, at least 10000 probes, at least 15000 probes, at least 20000 probes, at least 25000 probes, at least 30000 probes, or at least 4000 probes each mapping to a different unique location in the human reference genome are used in the targeted nucleic acid sequencing. In some embodiments, each probe is designed to map to a particular bin in the plurality of bins and the plurality of bins is for a respective specific region of a reference genome that has been identified as being associated with cancer through cancer- and/or tissue-specific methylation patterns in cfDNA relative to non-cancer controls as discussed above and in Example 4. In some embodiments, such probes are used for targeted sequencing (e.g., methylation sequencing) and the regions of the reference genome that these probes uniquely map to are sequenced at a coverage of at least 5×, at least 10×, at least 15×, at least 20×, at least 25×, at least 30×, at least 50×, at least 100×, at least 250×, at least 500×, or at least 1000× (for the portions of the genome to which the probes map).

In some embodiments, with reference to block 1032, each respective bin value in the first plurality of bin values or the second plurality of bin values is representative of a number of fragments mapping to a respective bin in the plurality of bins or a respective methylation pattern measured in the corresponding biological sample for the respective bin in the plurality of bins. The described technique for using transfer learning to determine whether a subject has a cancer condition can be implemented using methylation patterns measured in subjects' biological samples. Additionally or alternatively, because methylation sequencing data can provide copy number, a copy number analysis can be performed with methylation sequencing data.

In embodiments in accordance with the present disclosure, a biological sample of a respective subject in the first plurality or second plurality of subjects can be any type of a sample obtained from a subject. In some embodiments, the biological sample comprises blood, whole blood, plasma, serum, urine, cerebrospinal fluid, fecal, saliva, sweat, tears, pleural fluid, pericardial fluid, or peritoneal fluid of a respective subject. In some embodiments, the biological sample consists of blood, whole blood, plasma, serum, urine, cerebrospinal fluid, fecal, saliva, sweat, tears, pleural fluid, pericardial fluid, or peritoneal fluid of a respective subject.

In some embodiments, transfer learning is based on using different biological samples from the same subjects. Accordingly, in some embodiments, the first and second dataset can be generated based on analysis of samples acquired from the same cohort. In such embodiments, each biological sample in the first dataset is a first tissue type, and each biological sample in the second dataset is a second tissue type, and at least some of the subjects of the first dataset are in the second dataset as well. For example, tissue samples from a CCGA dataset can be used to extract features, and these features can be applied to cfDNA samples, for the same cohorts of subjects.

In some embodiments, with reference to block 1034, the first tissue type is blood and the biological sample for each respective subject in the first plurality or second plurality of subjects is blood, and the second tissue type is one of breast tissue, lung tissue, prostate tissue, colorectal tissue, renal tissue, uterine tissue, pancreatic tissue, esophagus tissue, head/neck tissue, ovarian tissue, hepatobiliary tissue, cervical tissue, thyroid tissue, bladder tissue. The biological sample for each respective subject in the second plurality of subjects consists of the second tissue type, or biological sample for each respective subject in the second plurality of subjects comprises a solid tumor of the second tissue type.

In various embodiments, a first tissue type and a biological sample for each respective subject in the first plurality of subjects can be selected from blood, any type of tissue (e.g., breast tissue, lung tissue, prostate tissue, colorectal tissue, renal tissue, uterine tissue, pancreatic tissue, esophagus tissue, head/neck tissue, ovarian tissue, hepatobiliary tissue, cervical tissue, thyroid tissue, bladder tissue, etc.), or a solid tumor of a certain type of tissue. A second tissue type and a biological sample for each respective subject in the second plurality of subjects can similarly be selected from blood, any type of tissue, or a solid tumor of a certain type of tissue. For example, in some embodiments, the biological sample for each respective subject in the first plurality of subjects comprises a solid tumor of a certain tissue type, the second tissue type is blood and the biological sample for each respective subject in the second plurality of subjects is blood. In some embodiments, each respective subject in the first plurality of subjects comprises a solid tumor of the first tissue type, and the second tissue type is blood and the biological sample for each respective subject in the second plurality of subjects is blood.

A cancer condition can be any type of a cancer condition. For example, in some embodiments, with reference to block 1036, each respective cancer condition in a cancer condition set is selected from the group consisting of non-cancer, breast cancer, lung cancer, prostate cancer, colorectal cancer, renal cancer, uterine cancer, pancreatic cancer, cancer of the esophagus, a lymphoma, head/neck cancer, ovarian cancer, a hepatobiliary cancer, a melanoma, cervical cancer, multiple myeloma, leukemia, thyroid cancer, bladder cancer, and gastric cancer.

Figure 10D:
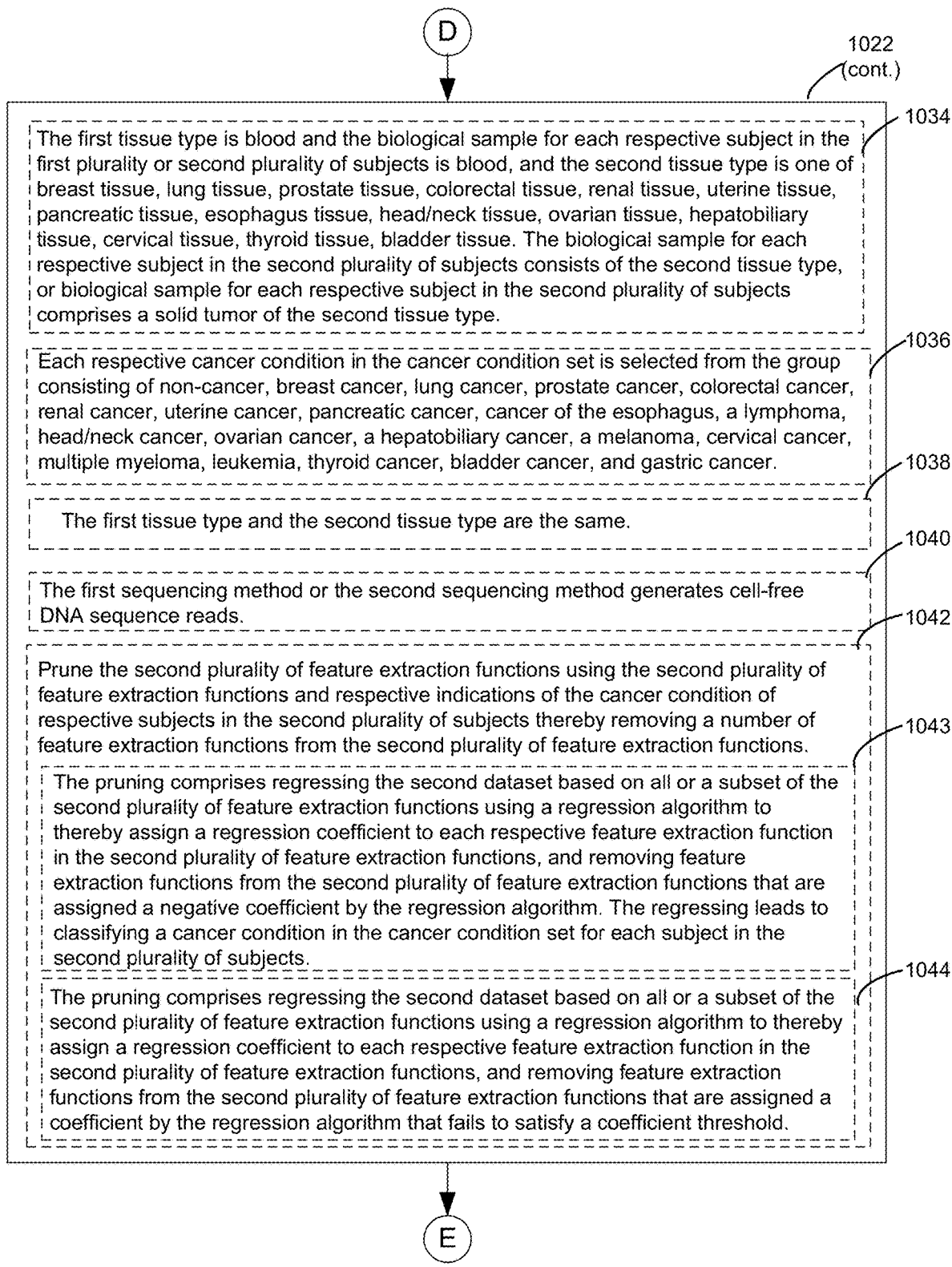

The first tissue type and the second tissue type can be the same, with reference to block 1038 of FIG. 10D. In some embodiments, however, the first tissue type and the second tissue type are different. In some embodiments, as shown at block 1040, the first sequencing method or the second sequencing method generates cell-free DNA sequence reads.

In some embodiments in accordance with the present disclosure, as described above, the number of the second plurality of feature extraction functions can be reduced. Thus, with reference to block 1042 of FIG. 10D, the second plurality of feature extraction functions can be pruned using the second plurality of feature extraction functions and respective indications of the cancer condition of respective subjects in the second plurality of subjects, thereby removing a number of feature extraction functions from the second plurality of feature extraction functions. In this way, a reduced number of feature extraction functions is identified, as shown by way of example at block 228 of FIG. 2. In some embodiments (block 1043), the pruning comprises regressing the second dataset based on all or a subset of the second plurality of feature extraction functions using a regression algorithm to thereby assign a regression coefficient to each respective feature extraction function in the second plurality of feature extraction functions, and removing feature extraction functions from the second plurality of feature extraction functions that are assigned a negative coefficient by the regression algorithm. In some embodiments (block 1044), the pruning comprises regressing the second dataset based on all or a subset of the second plurality of feature extraction functions using a regression algorithm to thereby assign a regression coefficient to each respective feature extraction function in the second plurality of feature extraction functions, and removing feature extraction functions from the second plurality of feature extraction functions that are assigned a coefficient by the regression algorithm that fails to satisfy a coefficient threshold. Regardless of its specific type, the regressing leads to classifying a cancer condition in the cancer condition set for each subject in the second plurality of subjects. In some embodiments, the feature extraction functions for the second dataset are obtained and then pruned using the techniques disclosed above for the first dataset. Further, in some such embodiments, they are obtained and subsequently pruned on a pairwise basis as discussed above for the first dataset. Further, in some alternative embodiments, they are obtained and subsequently pruned on a multivariate basis as discussed above for the first dataset.

Data Block 1044-1051

In some embodiments, as shown at block 1044 of FIG. 10E, the described systems and methods for training one or more classifiers to discriminate between each cancer condition in the cancer condition set further perform transforming, based on at least each respective feature extraction function in the first plurality of feature extraction functions, the respective second plurality of bin values of each corresponding subject in the second plurality of subjects against the respective feature extraction function, thereby contributing to a transformed second dataset comprising a respective plurality of feature values for each corresponding subject. Feature extraction functions obtained using the first dataset (which can be in the form of a reduced number of feature extraction functions generated as a result of applying pruning to the first plurality of feature extraction functions) are applied against the bin values of each corresponding subject in the second plurality of subjects. For example, in some embodiments, each feature extraction function in the first plurality of feature extraction functions can encode a linear or nonlinear function of bin values of all or a subset of the plurality of bins from the first dataset. The transforming includes applying the linear or nonlinear function, generated (or "learned") based on at least some of the bin values from the first dataset, to the bin values in the second dataset. In such embodiments, is will be appreciated that in such embodiments, the index for the plurality of bins of the first and second dataset is the same. In other words, each respective bin in the first dataset has a corresponding bin in the second dataset, where corresponding bins represent the same subset of the reference genome of the species.

In some embodiments, the transforming involves using convolutional neural networks, including deep convolutional neural networks. Thus, with reference to block 1046, in some embodiments, the first feature extraction technique is a first convolutional neural network that comprises a first plurality of convolutional layers, each respective convolutional layer in the first plurality of convolutional layers is associated with a learned weight vector that is obtained through back-propagation of the first convolutional neural network using the respective bin values and respective indications of the cancer condition of respective subjects in the first dataset, and the respective learned weight vector of each convolutional layer in a subset of the first plurality of convolutional layers collectively represent the first plurality of feature extraction functions. In such embodiments, the transforming (block 1044) comprises inputting the corresponding second plurality of bin values of a respective subject in the second plurality of subjects into a second convolutional network that comprises the subset of the first plurality of convolutional layers, where a weight vector of each respective convolutional layer in the second convolutional neural network is initialized and in some embodiments frozen at values of the learned weight vector of the corresponding convolutional layer in the first convolutional neural network. See for example, Yosinski et al., 2014, "How transferable are features in deep neural networks?", Advances in Neural Information Processing Systems 27, pages 3320-3328, which is hereby incorporated by reference. In some such embodiments, the first plurality of convolutional layers comprises any suitable number of layers. For example, in some embodiments, the first plurality of convolutional layers comprises three, four, five, six, seven, or eight convolutional layers, as shown at block 1048. As another example, in some embodiments (block 1050), the first plurality of convolutional layers comprises five convolutional layers and the subset of the first plurality of convolutional layers consists of the first three convolutional layers of the first convolutional neural network.

In some embodiments, with reference to block 1051 of FIG. 10E, the transforming (C) is based on each respective feature extraction function in the first plurality of feature extraction functions and a second plurality of feature extraction functions. The second plurality of feature extraction functions can be obtained by applying a second feature extraction technique to the respective bin values of respective subjects in the second dataset, thereby identifying a second plurality of feature extraction functions, as shown in FIG. 6. Each feature extraction function in the second plurality of feature extraction functions independently encodes a linear or nonlinear function of bin values of all or a subset of the plurality of bins, and the second plurality of feature extraction functions collectively discriminates respective subjects in the second plurality of subjects as having a cancer condition within the cancer condition set based on respective bin values for the respective subjects.

Data Blocks 1052-1076

Figure 10F:
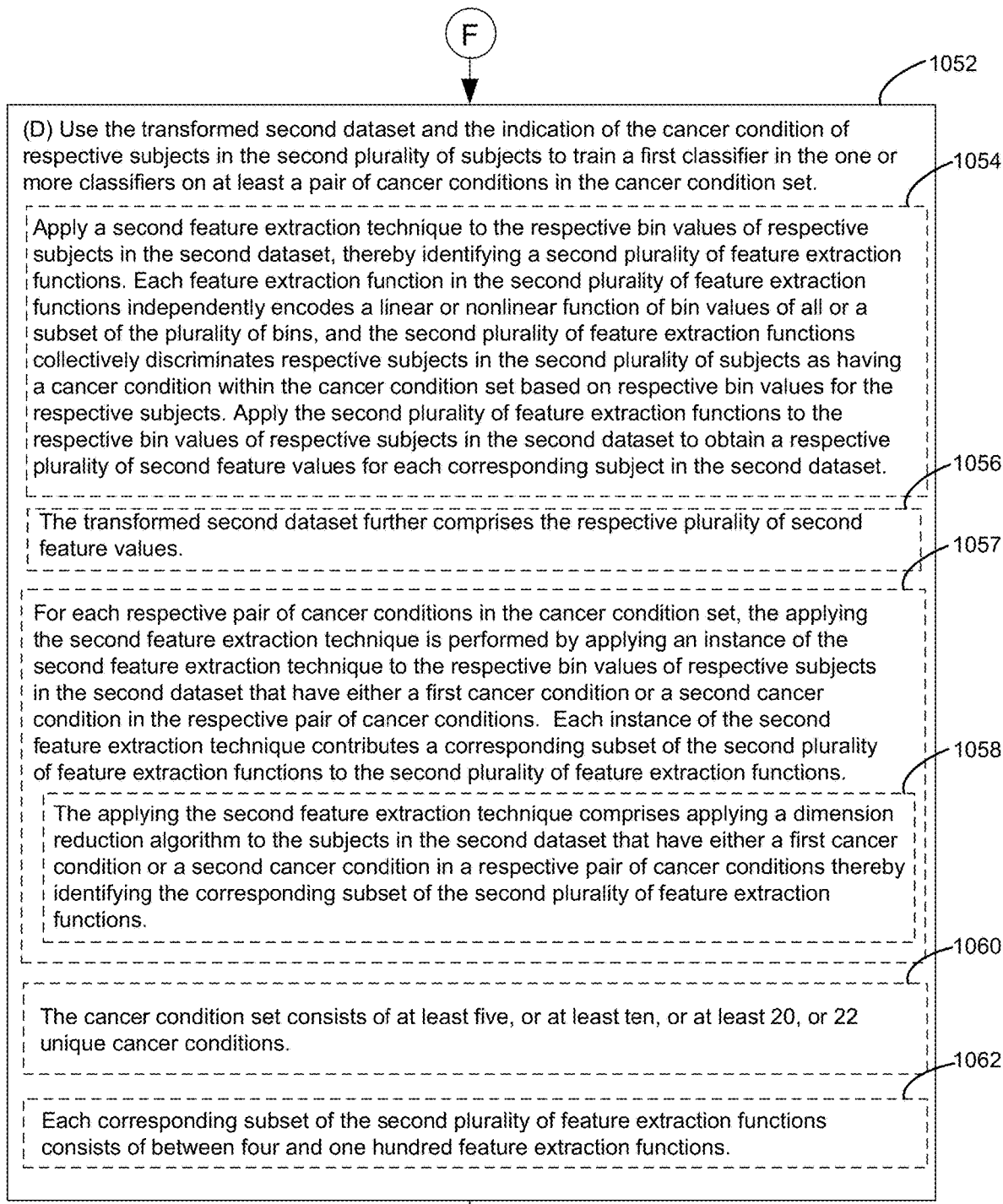

In some embodiments, as shown at block 1052 of FIG. 10F, the described systems and methods for training one or more classifiers further comprise, once the transformed second dataset is generated, using the transformed second dataset and the indication of the cancer condition of respective subjects in the second plurality of subjects to train a first classifier (also referred to herein as a "classifier") in the one or more classifiers on at least a pair of cancer conditions in the cancer condition set. FIG. 8, discussed above, illustrates training a classifier in accordance with embodiments of the present disclosure.

In some embodiments, as discussed above (FIG. 2), in addition to applying a first feature extraction technique to the first dataset to identify a first plurality of feature extraction functions, a second feature extraction technique is applied to the second dataset, e.g., to second dataset 124, to generate to identify a second plurality of feature extraction functions (e.g., second feature extraction functions 224 of FIG. 2). Thus, with reference to block 1054 of FIG. 10F, the described method performs applying a second feature extraction technique to the respective bin values of respective subjects in the second dataset, thereby identifying a second plurality of feature extraction functions. Each feature extraction function in the second plurality of feature extraction functions independently encodes a linear or nonlinear function of bin values of all or a subset of the plurality of bins, and the second plurality of feature extraction functions collectively discriminates respective subjects in the second plurality of subjects as having a cancer condition within the cancer condition set based on respective bin values for the respective subjects. The method in accordance with some embodiments of the present disclosure further includes applying the second plurality of feature extraction functions to the respective bin values of respective subjects in the second dataset to obtain a respective plurality of second feature values for each corresponding subject in the second dataset. Further, with reference to block 1056 of FIG. 10F, in embodiments in which the plurality of second feature values is obtained, the transformed second dataset comprises the respective plurality of second feature values.

Furthermore, in some embodiments, with reference to block 1057 of FIG. 10F, for each respective pair of cancer conditions in the cancer condition set, the applying the second feature extraction technique is performed by applying an instance of the second feature extraction technique to the respective bin values of respective subjects in the second dataset that have either a first cancer condition or a second cancer condition in the respective pair of cancer conditions. Each instance of the second feature extraction technique contributes a corresponding subset of the second plurality of feature extraction functions to the second plurality of feature extraction functions.

In some embodiments, as discussed above, the applying the first feature extraction technique comprises applying a dimension reduction algorithm to the subjects in the first dataset that have either a first cancer condition or a second cancer condition in the respective pair of cancer conditions thereby identifying the corresponding subset of the first plurality of feature extraction functions. Furthermore, in some embodiments, with reference to block 1058, the applying the second feature extraction technique comprises applying a dimension reduction algorithm to the subjects in the second dataset that have either a first cancer condition or a second cancer condition in a respective pair of cancer conditions, thereby identifying the corresponding subset of the second plurality of feature extraction functions. A dimension reduction algorithm can alternatively be applied to more than two cancer conditions, e.g., to three or more than three cancer conditions.

The dimension reduction algorithm can be a linear dimension reduction algorithm or a non-linear dimension reduction algorithm. Similar to a dimension reduction algorithm applied to subjects in the first dataset, the dimension reduction algorithm that can be applied to subjects in the second dataset, can be a principal component analysis algorithm, such that each respective feature extraction function in the corresponding subset of the second plurality of feature extraction functions comprises a respective principal component derived by the dimension reduction algorithm. In some embodiments, the corresponding subset of the second plurality of feature extraction functions is limited to a threshold number of principal components calculated by the principal component analysis algorithm. Also, in some embodiments, each principal component calculated by the principal component analysis algorithm is assigned an eigenvalue by the principal component algorithm, and the corresponding subset of the second plurality of feature extraction functions is limited to the threshold number of principal components assigned the highest eigenvalues.

In some embodiments, the cancer condition set consists of at least five, at least ten, at least 20 unique cancer conditions. In some embodiments, the cancer condition set consists of 22 unique cancer conditions, as shown at block 1060 of FIG. 10F. In some embodiments, the cancer condition set consists of 231 unique pairs of cancer conditions. It should be appreciated that the cancer condition set can include any other number of unique pairs of cancer conditions. With reference to block 1062, in some embodiments, each corresponding subset of the second plurality of feature extraction functions consists of between 4 and 100 feature extraction functions. In some embodiments, once the subsets contributing to the second plurality of feature extraction functions are combined, the second plurality of feature extraction functions can be between 500 and 20,000 functions, between 500 and 15,000 functions, between 500 and 10,000 functions, between 500 and 5,000 functions, between 500 and 4,000 functions, between 500 and 3,000 functions, between 500 and 2,000 functions, or between 500 and 1,000 functions.

In some embodiments, as discussed above, a feature extraction technique (either the first or second feature extraction technique) is applied to each pair of cancer conditions in a cancer condition set. In other embodiments, a feature extraction technique is concurrently applied to three, four, or more than four cancer conditions in a cancer condition set. Furthermore, in some embodiments, multinomial feature extraction is performed for all cancer conditions in a cancer condition set simultaneously.

Figure 10G:
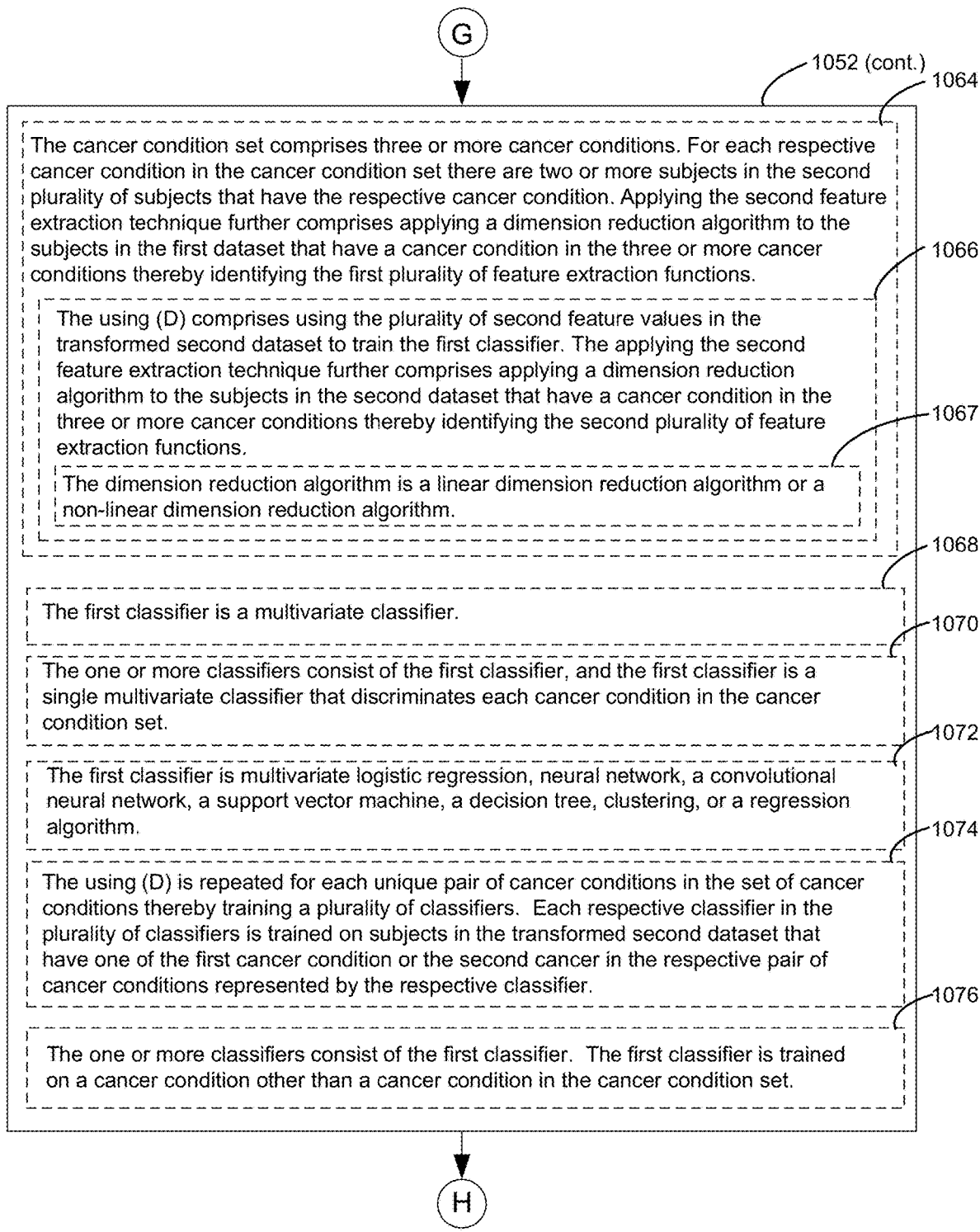

In some embodiments, with reference to block 1064 of FIG. 10G, the cancer condition set comprises three or more cancer conditions. As discussed above (block 1004), in such embodiments, for each respective cancer condition in the cancer condition set, there may be two or more subjects in the first plurality of subjects that have the respective cancer condition, the applying the first feature extraction technique further comprises applying a dimension reduction algorithm to the subjects in the first dataset that have a cancer condition in the three or more cancer conditions, thereby identifying the first plurality of feature extraction functions.

Further, with reference to block 1066, in embodiments in which the cancer condition set comprises three or more cancer conditions, the using (block 1052 of FIG. 10F) comprises using the plurality of second feature values in the transformed second dataset to train the first classifier, where the applying the second feature extraction technique further comprises applying a dimension reduction algorithm to the subjects in the second dataset that have a cancer condition in the three or more cancer conditions thereby identifying the second plurality of feature extraction functions. In some embodiments, the dimension reduction algorithm is a linear dimension reduction algorithm or a non-linear dimension reduction algorithm, as shown at block 1067 of FIG. 10G. The dimension reduction algorithm can be a principal component analysis algorithm, or any other type of a dimension reduction algorithm, which can be the same dimension reduction algorithm applied to subjects in the first dataset, or a different dimension reduction algorithm. Non-limiting examples of a dimension reduction algorithm comprise a factor analysis algorithm, Sammon mapping, curvilinear components analysis, a stochastic neighbor embedding (SNE) algorithm, an Isomap algorithm, a maximum variance unfolding algorithm, a locally linear embedding algorithm, a t-SNE algorithm, a non-negative matrix factorization algorithm, a kernel principal component analysis algorithm, a graph-based kernel principal component analysis algorithm, a linear discriminant analysis algorithm, a generalized discriminant analysis algorithm, a uniform manifold approximation and projection (UMAP) algorithm, a LargeVis algorithm, a Laplacian Eigenmap algorithm, a Fisher's linear discriminant analysis algorithm, or any other dimension reduction algorithm.

Referring back to block 1052 of FIG. 10F, the trained classifier can be any one or more of various classifiers. The classifier can be trained using the transformed second dataset and the indication of the cancer condition of respective subjects in the second plurality of subjects. In some embodiments, as discussed above in connection at least with blocks 1054 and 1056, the transformed second dataset comprises the respective plurality of second feature values.

In some embodiments, with reference to block 1068, the first classifier is a multivariate classifier. In some embodiments, with reference to block 1070, the one or more classifiers consist of the first classifier, and the first classifier is a single multivariate classifier that discriminates each cancer condition in the cancer condition set. In some embodiments, with reference to block 1072, the first classifier is multivariate logistic regression, a neural network algorithm, a convolutional neural network algorithm, a support vector machine (SVM) algorithm, a decision tree algorithm, a clustering algorithm, or a regression algorithm.

Logistic regression algorithms are disclosed in Agresti, *An Introduction to Categorical Data Analysis*, 1996, Chapter 5, pp. 103-144, John Wiley & Son, New York, which is hereby incorporated by reference.

Neural network algorithms, including convolutional neural network algorithms, are disclosed in See, Vincent et al., 2010, "Stacked denoising autoencoders: Learning useful representations in a deep network with a local denoising criterion," J Mach Learn Res 11, pp. 3371-3408; Larochelle et al., 2009, "Exploring strategies for training deep neural networks," J Mach Learn Res 10, pp. 1-40; and Hassoun, 1995, Fundamentals of Artificial Neural Networks, Massachusetts Institute of Technology, each of which is hereby incorporated by reference.

SVM algorithms are described in Cristianini and Shawe-Taylor, 2000, "An Introduction to Support Vector Machines," Cambridge University Press, Cambridge; Boser et al., 1992, "A training algorithm for optimal margin classifiers," in Proceedings of the $5^{th}$ Annual ACM Workshop on Computational Learning Theory, ACM Press, Pittsburgh, Pa., pp. 142-152; Vapnik, 1998, Statistical Learning Theory, Wiley, New York; Mount, 2001, *Bioinformatics: sequence and genome analysis*, Cold Spring Harbor Laboratory Press, Cold Spring Harbor, N.Y.; Duda, *Pattern Classification*, Second Edition, 2001, John Wiley & Sons, Inc., pp. 259, 262-265; and Hastie, 2001, *The Elements of Statistical Learning*, Springer, New York; and Furey et al., 2000, *Bioinformatics* 16, 906-914, each of which is hereby incorporated by reference in its entirety. When used for classification, SVMs separate a given set of binary labeled data training set with a hyper-plane that is maximally distant from the labeled data. For cases in which no linear separation is possible, SVMs can work in combination with the technique of 'kernels', which automatically realizes a non-linear mapping to a feature space. The hyper-plane found by the SVM in feature space corresponds to a non-linear decision boundary in the input space.

Decision trees are described generally by Duda, 2001, *Pattern Classification*, John Wiley & Sons, Inc., New York, pp. 395-396, which is hereby incorporated by reference. Tree-based methods partition the feature space into a set of rectangles, and then fit a model (like a constant) in each one. In some embodiments, the decision tree is random forest regression. One specific algorithm that can be used is a classification and regression tree (CART). Other specific decision tree algorithms include, but are not limited to, ID3, C4.5, MART, and Random Forests. CART, ID3, and C4.5 are described in Duda, 2001, *Pattern Classification*, John Wiley & Sons, Inc., New York, pp. 396-408 and pp. 411-412, which is hereby incorporated by reference. CART, MART, and C4.5 are described in Hastie et al., 2001, *The Elements of Statistical Learning*, Springer-Verlag, New York, Chapter 9, which is hereby incorporated by reference in its entirety. Random Forests are described in Breiman, 1999, "Random Forests—Random Features," Technical Report 567, Statistics Department, U.C. Berkeley, September 1999, which is hereby incorporated by reference in its entirety.

Clustering is described at pages 211-256 of Duda and Hart, *Pattern Classification and Scene Analysis*, 1973, John Wiley & Sons, Inc., New York, (hereinafter "Duda 1973") which is hereby incorporated by reference in its entirety. As described in Section 6.7 of Duda 1973, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda 1973, where it is stated that one way to begin a clustering investigation is to define a distance function and to compute the matrix of distances between all pairs of samples in the training set. If distance is a good measure of similarity, then the distance between reference entities in the same cluster will be significantly less than the distance between the reference entities in different clusters. However, as stated on page 215 of Duda 1973, clustering does not require the use of a distance metric. For example, a nonmetric similarity function s(x, x') can be used to compare two vectors x and x'. Conventionally, s(x, x') is a symmetric function whose value is large when x and x' are somehow "similar." An example of a nonmetric similarity function s(x, x') is provided on page 218 of Duda 1973.

Once a method for measuring "similarity" or "dissimilarity" between points in a dataset has been selected, clustering requires a criterion function that measures the clustering quality of any partition of the data. Partitions of the dataset that extremize the criterion function are used to cluster the data. See page 217 of Duda 1973. Criterion functions are discussed in Section 6.8 of Duda 1973.

More recently, Duda et al., *Pattern Classification*, $2^{nd}$ edition, John Wiley & Sons, Inc. New York, has been published. Pages 537-563 describe clustering in detail. More information on clustering techniques can be found in Kaufman and Rousseeuw, 1990, Finding Groups in Data: An Introduction to Cluster Analysis, Wiley, New York, N.Y.; Everitt, 1993, Cluster analysis (3d ed.), Wiley, New York, N.Y.; and Backer, 1995, Computer-Assisted Reasoning in Cluster Analysis, Prentice Hall, Upper Saddle River, New Jersey, each of which is hereby incorporated by reference. Particular exemplary clustering techniques that can be used in the present disclosure include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering. Such clustering can be on the set of first features $\{p1, \ldots, pN-K\}$ (or the principal components derived from the set of first features). In some embodiments, the clustering comprises unsupervised clustering (block 490) where no pre-conceived notion of what clusters should form when the training set is clustered are imposed.

In some embodiments, as shown at block 1074 of FIG. 10G, the using the transformed second dataset to train the classifier (block 1052) is repeated for each unique pair of cancer conditions in the set of cancer conditions thereby training a plurality of classifiers. Each respective classifier in the plurality of classifiers is trained on subjects in the transformed second dataset that have one of the first cancer condition or the second cancer in the respective pair of cancer conditions represented by the respective classifier. In some embodiments, with reference to block 1076, the one or more classifiers consist of the first classifier and the first classifier is trained on a cancer condition other than a cancer condition in the cancer condition set.

Data Blocks 1078-1088

The classifier trained in accordance with embodiments of the present disclosure is used to classify test subjects using their genotyping information, by assigning a cancer condition to each of the test subjects. In this way, with reference to block 1078 of FIG. 10H, the first classifier is used to classify a test subject to a first cancer condition using genotypic information, in electronic form, based on sequence read data in a test biological sample obtained from the test subject as input to the first classifier.

The test biological sample can be any type of a sample. For example, in some embodiments, with reference to block 1080, the test biological sample comprises blood, whole blood, plasma, serum, urine, cerebrospinal fluid, fecal, saliva, sweat, tears, pleural fluid, pericardial fluid, or peritoneal fluid of the test subject. In some embodiments, as shown at block 1082, the first cancer condition is in the set of cancer conditions.

Furthermore, in some embodiments, with reference to block 1084, the one or more classifiers are used to determine a likelihood that a test subject has each cancer condition in the cancer condition set using genotypic information, in electronic form, based on sequence read data in a test biological sample obtained from the test subject as input to each classifier in the one or more classifiers. The test biological sample can comprise blood, whole blood, plasma, serum, urine, cerebrospinal fluid, fecal, saliva, sweat, tears, pleural fluid, pericardial fluid, or peritoneal fluid of the test subject, as shown at block 1086.

Figure 10H:
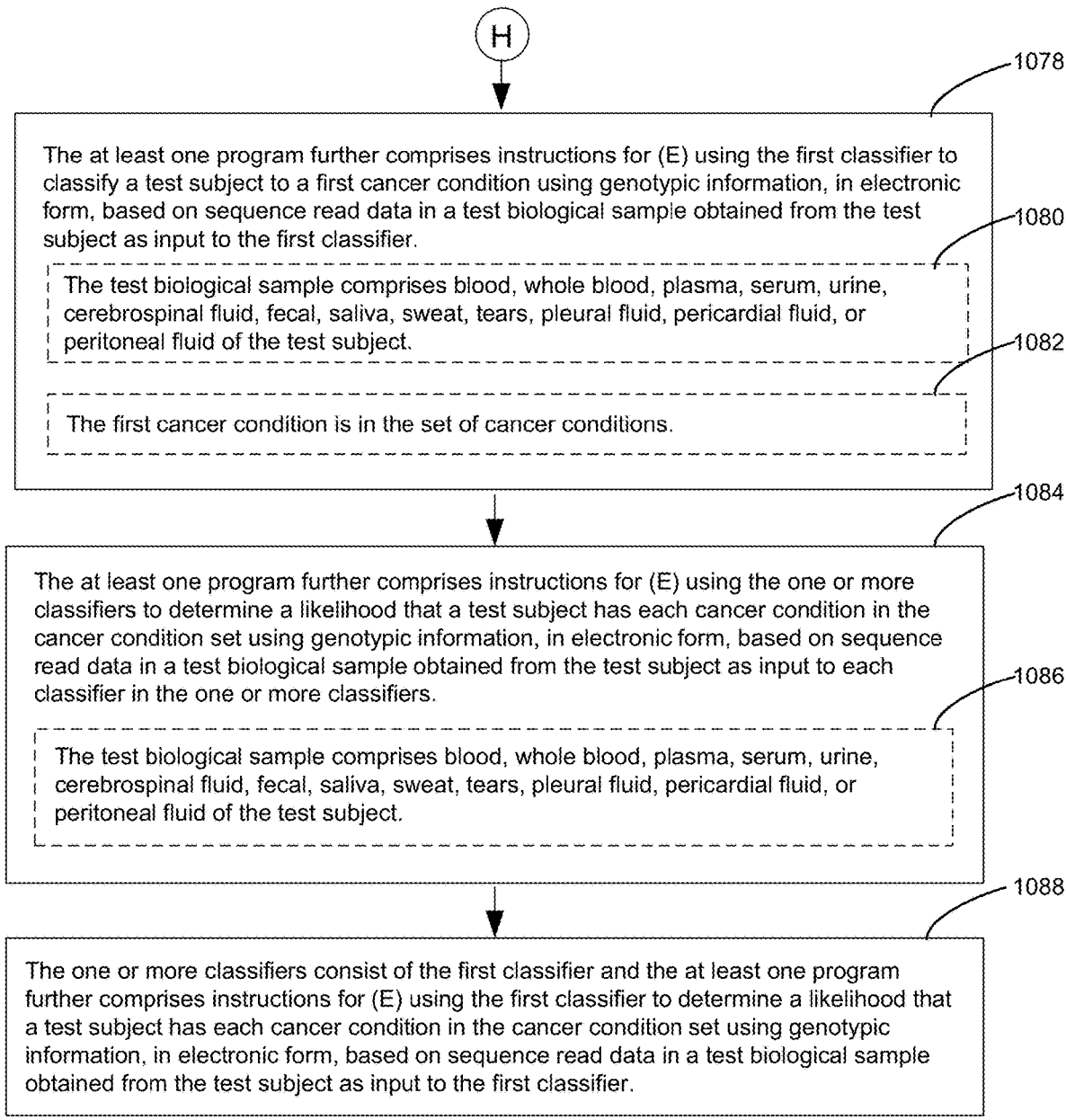

As also shown in FIG. 10H (block 1088), in some embodiments, the one or more classifiers consist of the first classifier and the at least one program further comprises instructions for using the first classifier to determine a likelihood that a test subject has each cancer condition in the cancer condition set using genotypic information, in electronic form, based on sequence read data in a test biological sample obtained from the test subject as input to the first classifier.

In some embodiments, scaling a respective first bin value for each respective bin in the plurality of bins for each respective subject in the first plurality of subjects is performed by taking a log transformation of the respective first bin value thereby forming a log transformed first bin value for the respective bin, subtracting a mean value of the respective log transformed first bin value across the first plurality of subjects from the log transformed first bin value of the respective bin thereby forming a first normalized bin value for the respective bin, and subsequently dividing the respective first normalized bin value for the respective bin by a standard deviation of the first normalized bin value across the first plurality of subjects thereby scaling the first bin value for each respective bin in the plurality of bins for each respective subject in the first plurality of subjects.

Additionally or alternatively, in some embodiments, scaling a respective second bin value for each respective bin in the plurality of bins for each respective subject in the second plurality of subjects is performed by taking a log transformation of the respective second bin value thereby forming a log transformed second bin value for the respective bin, subtracting a mean value of the respective log transformed second bin value across the second plurality of subjects from the log transformed second bin value of the respective bin thereby forming a second normalized bin value for the respective bin, and subsequently dividing the respective second normalized bin value for the respective bin by a standard deviation of the second normalized bin value across the second plurality of subjects thereby scaling the second bin value for each respective bin in the plurality of bins for each respective subject in the second plurality of subjects.

In some embodiments, the classifier trained using the transformed second dataset is used to determine and apply a treatment regimen to a test subject based at least in part, on a value of the classifier (e.g., predicted cancer condition) upon application of bin values from the test subject that are obtained in one of the ways disclosed for the first or second dataset described above. In some embodiments, the treatment regimen comprises applying an agent for cancer to the test subject based on the cancer condition determined by the classifier for the test subject. Non-limiting examples of agents for cancer that can be applied based on an output of the classifier trained using the transformed second dataset include, but are not limited to, hormones, immune therapies, radiography, and cancer drugs. Examples of cancer drugs include, but are not limited to, Lenalidomid, Pembrolizumab, Trastuzumab, Bevacizumab, Rituximab, Ibrutinib, Human Papillomavirus Quadrivalent (Types 6, 11, 16, and 18) Vaccine, Pertuzumab, Pemetrexed, Nilotinib, Nilotinib, Denosumab, Abiraterone acetate, Promacta, Imatinib, Everolimus, Palbociclib, Erlotinib, Bortezomib, and Bortezomib.

In some embodiments, the test subject has been treated with an agent for cancer and the disclosed methods further comprise using the output of the classifier trained using the transformed second dataset to evaluate a response of the test subject to the agent for cancer.

In some embodiments, the test subject has been treated with an agent for cancer and the disclosed methods further comprise using a cancer condition predicted by the classifier trained using the transformed second dataset to determine whether to intensify (e.g., increase radiation, increase drug dosage, etc.) or discontinue the agent for cancer in the subject.

In some embodiments, the subject has been subjected to a surgical intervention to address a cancer condition and the method further comprises using the cancer condition predicted by the classifier trained using the transformed second dataset to evaluate a condition of the test subject in response to the surgical intervention.

In some embodiments, the classifier trained using the transformed second dataset is, in turn, used to generate a report that is communicated to a caretaker (e.g., doctor, medical professional, insurance agency, relative) associated with a test subject based at least in part, on one or more values provided by the classifier (e.g., predicted cancer condition) upon application of bin values obtained from a test subject obtained in the same way that bin values were obtained for the subjects in the first or second datasets described herein. In some such embodiments, the one or more values of the classifier indicate that the test subject has or does not have any of the cancer conditions disclosed herein. In some such embodiments, each of the one or more values of the classifier provides a likelihood or probability that the test subject has or does not have any of the cancer conditions disclosed herein. In such embodiments, the classifier provides a likelihood or probability, for each respective cancer condition in a set of cancer conditions, of the test subject having the respective cancer condition, where the set of cancer conditions are drawn from any of the cancer conditions disclosed herein. The set of cancer conditions can be a single cancer condition, two cancer conditions, or any number of cancer conditions some of which are disclosed herein. As disclosed herein, non-limiting example cancer conditions are specific origins of cancer (e.g., breast, lung, etc.). As disclosed herein, additional non-limiting example cancer conditions are specific stages of particular cancer (e.g., stage I breast, stage II breast cancer, etc.).

Example 1: The Cancer Genome Atlas (TCGA) Study

In some embodiments, genotypic information is obtained using data from the Cancer Genome Atlas (TCGA) cancer genomics program that is led by the National Cancer Institute and the National Human Genome Research Institute. The TCGA dataset comprises, among other information, gene expression profiles from dissected tissue samples of a large number of human cancer samples. The information is obtained using high-throughput platforms including gene expression mutation, copy number, methylation, etc. The TCGA dataset is a publicly available dataset comprising more than two petabytes of genomic data for over 11,000 cancer patients, including clinical information about the cancer patients, metadata about the samples (e.g., the weight of a sample portion, etc.) collected from such patients, histopathology slide images from sample portions, and molecular information derived from the samples (e.g., mRNA/miRNA expression, protein expression, copy number, etc.). The TCGA dataset includes array-based sequencing data obtained using genome-wide array analysis using the Genome-Wide Human SNP Array 6.0 from Affymetrix for subjects. The TCGA dataset includes such data for subjects with a known particular cancer and the data for each respective subject is from the isolated and pure tissue originating the cancer in the respective subject. A total of 33 different cancers are represented in the TCGA dataset: breast (breast ductal carcinoma, bread lobular carcinoma) central nervous system (glioblastoma multiforme, lower grade glioma), endocrine (adrenocortical carcinoma, papillary thyroid carcinoma, paraganglioma & pheochromocytoma), gastrointestinal (cholangiocarcinoma, colorectal adenocarcinoma, esophageal cancer, liver hepatocellular carcinoma, pancreatic ductal adenocarcinoma, and stomach cancer), gynecologic (cervical cancer, ovarian serous cystadenocarcinoma, uterine carcinosarcoma, and uterine corpus endometrial carcinoma), head and neck (head and neck squamous cell carcinoma, uveal melanoma), hematologic (acute myeloid leukemia, Thymoma), skin (cutaneous melanoma), soft tissue (sarcoma), thoracic (lung adenocarcinoma, lung squamous cell carcinoma, and mesothelioma), and urologic (chromophobe renal cell carcinoma, clear cell kidney carcinoma, papillary kidney carcinoma, prostate adenocarcinoma, testicular germ cell cancer, and urothelial bladder carcinoma). See Blum et al., 2018, "TCGA-Analyzed Tumors," SNAPSHOT 173(2), P530, which is hereby incorporated by reference.

Example 2: The Circulating Cell-Free Genome Atlas Study (CCGA)

Subjects from the CCGA were used in the present disclosure. The CCGA (NCT02889978) CCGA is a prospective, multi-center, observational cfDNA-based, case-control early cancer detection study that has enrolled 15,254 demographically-balanced participants (44% non-cancer, 56% cancer) from 142 sites in North America with longitudinal follow-up, designed to develop a single blood test for 50+ cancer types across cancer stages. See, Liu et al., "Sensitive and specific multi-cancer detection and localization using methylation signatures in cell-free DNA," Ann. Oncol 2020, https://doi.org/10.1016/j.annonc.2020.02.011, which is hereby incorporated by reference. The CCGA study includes a plasma cell-free DNA (cfDNA)-based multi-cancer detection assay. Up to 80 ml of whole blood was collected from subjects with newly diagnosed therapy-naive cancer (C, case) and participants without a diagnosis of cancer (non-cancer [NC], control) as defined at enrollment.

All samples were analyzed by: 1) paired cfDNA and white blood cell (WBC)-targeted sequencing (60,000×, 507 gene panel); a joint caller removed WBC-derived somatic variants and residual technical noise; 2) paired cfDNA and WBC whole-genome sequencing (WGS; 35×); a novel machine learning algorithm generated cancer-related signal scores; joint analysis identified shared events; and 3) cfDNA whole-genome bisulfite sequencing (WGBS; 34×); normalized scores were generated using abnormally methylated fragments. In the targeted assay, non-tumor WBC-matched cfDNA somatic variants (SNVs/indels) accounted for 76% of all variants in NC and 65% in C. Consistent with somatic mosaicism (e.g., clonal hematopoiesis), WBC-matched variants increased with age; several were non-canonical loss-of-function mutations not previously reported. After WBC variant removal, canonical driver somatic variants were highly specific to C (e.g., in EGFR and PIK3CA, 0 NC had variants vs 11 and 30, respectively, of C). Similarly, of 8 NC with somatic copy number alterations (SCNAs) detected with WGS, four were derived from WBCs. WGBS data of the CCGA reveals informative hyper- and hypo-fragment level CpGs (1:2 ratio); a subset of which was used to calculate methylation scores. A consistent "cancer-like" signal was observed in <1% of NC participants across all assays (representing potential undiagnosed cancers). An increasing trend was observed in NC vs stages I-III vs stage IV (nonsyn, SNVs/indels per Mb [Mean±SD] NC: 1.01±0.86, stages I-III: 2.43±3.98; stage IV: 6.45±6.79; WGS score NC: 0.00±0.08, I-III: 0.27±0.98; IV: 1.95±2.33; methylation score NC: 0±0.50; I-III: 1.02±1.77; IV: 3.94±1.70). These data demonstrate the feasibility of achieving >99% specificity for invasive cancer, and support the promise of cfDNA assay for early cancer detection.

Example 3

The inventors conducted experiments demonstrating improved cancer detection using the transfer learning approach in accordance with the described embodiments, which is denoted herein as an approach using CCGA+TCGA data. The TCGA copy number variation data is generated using Affymetrix SNP 6.0 array data used to identify genomic regions that are repeated and to infer the copy number of these repeats. The Genome-Wide Human SNP Array 6.0 contains more than 946,000 probes for the detection of copy number variation. This example is described with reference to FIG. 2.

Step 122 of FIG. 2. To classify tissue-of-origin, a first dataset was obtained. In this example, the first dataset is TCGA data described in Example 1 above. The TCGA data comprises, for each respective subject in a first plurality of subjects (here, over 11,000 cancer patients) of a species (human in this example), corresponding first genotypic information comprising TCGA array-based copy number counts for the probes represented in the TCGA dataset and an indication of a cancer condition of the respective subject. In this example, the cancer condition set is the 21 different cancers that are represented in both the TCGA and CCGA datasets plus the non-cancer healthy condition. The array-based TCGA copy number counts for the probes represented in the TCGA dataset were interpolated. The interpolation from the less dense (TCGA) to the more dense representation (CCGA) of the genome is not expected to be problematic because copy number aberrations in cancer are often much longer than the spacing between array-based markers (e.g., chromosome arm scale).

Step 132 of FIG. 2. Once copy number data of the TCGA dataset were processed using interpolation as described above, the processed (interpolated) TCGA copy number data for each respective subject was binned into approximately 30,000 bins spanning the entire genome and subjected to the filtering, e.g., high/low variability filter, disclosed in U.S. patent application Ser. No. 16/352,739, entitled "Method and System for Selecting, Managing, and Analyzing Data of High Dimensionality," filed Mar. 13, 2019, which is hereby incorporated by reference, to arrive at 23,000 bins. In this way, there were a corresponding 23,000 bin values for each subject in the TCGA dataset. Each such bin value represents a copy number count. TCGA provides a pipeline for converting the array values into copy number count values.

For reach respective subject in the TCGA dataset, the corresponding 23,000 bin values of the respective subject was normalized. A median bin value across the corresponding plurality of bin values for the respective subject is obtained. Then, each respective bin value in the plurality of bin values for the respective subject is divided by this median value thus assuring that the bin values for the respective subject are centered on a known value (e.g., on zero):

$$bv_i^* = \frac{bv_i}{\text{median}(bv_j)}$$

where, $bv_i$=the bin value of bin i in the plurality of bin values for the respective subject, $bv_i^*$=the normalized bin value of bin i in the plurality of bin values for the respective subject upon this normalization, and median($bv_j$)=the median bin value across the plurality of unnormalized bin values for the respective subject. See, U.S. patent application Ser. No. 16/352,739, entitled "Method and System for Selecting, Managing, and Analyzing Data of High Dimensionality," filed Mar. 13, 2019, which is hereby incorporated by reference.

From the normalized bin values of the respective subjects in the TCGA dataset, first feature extraction functions (copy number filters) that would be useful for differentiating among cancer types were learned. This was done for each pair of cancer types under consideration.

There were 231 pairs (21+1)*21/2, where 21 is the number of cancer conditions (cancer origin in this example) and 1 represents non-cancer, under consideration. For each respective pair in the 231 pairs, all the subjects in the TCGA dataset that had one of the cancer conditions represented by the pair were collectively subjected to principal component analysis (PCA). In this way, 231 separate principal component analyses were performed. For each respective PCA, the top 1000 principal components that explain the variation in copy number count across the 23,000 bins across the subjects contributing to the PCA (one of the 231 pairs) were retained.

Step 208 of FIG. 2. Principal components analysis (PCA) reduced the dimensionality of the classification problem by producing feature extraction functions (in the form of principal components derived from the principal component analysis of each respective first plurality of bin values across the TCGA dataset) that, on inspection, corresponded to weightings of bins highlighting particular amplification and deletion events.

To increase the likelihood that PCA would identify copy number aberrations that differ among the 21 cancer types considered in this example, the top 50 principal components (PCs) were kept (through pruning) for each pair of TCGA cancers matching CCGA cancer types, and for each of the 21 cancers against non-cancer, resulting in a total of 231 sets of 50 PCs each. The number 231 is arrived at by the consideration of 231 pairs (21+1)*21/2, where 21 is the number of cancer conditions (cancer origin in this example) and 1 represents non-cancer. As such, the first plurality of feature extraction functions consisted of 231×50 PCs, or a total of 11,550 feature extraction functions 132.

Despite being fit independently on each pair of diagnostic classes, PCs were by design generated without explicit knowledge of the cancer types in each pair. To address this limitation, a determination was made as to which of the PCs were informative for tissue-of-origin classification. To reduce the set of 11,550 PCs, within TCGA data, L1 regularized logistic regression was performed to classify each of the 231 pairs, and only PCs with non-zero coefficients were retained in the first plurality of feature extraction functions. This resulted in an average of 6.5 PCs (feature extraction functions) per pair of cancer conditions, reducing to 1502 the number of PCs retained. These PCs were interpreted as the feature extraction functions that best differentiated between diagnostic classes.

Steps 224, 124, 142 and 228 of FIG. 2. An additional 20 cfDNA-specific feature extraction functions were generated by PCA (second feature extraction functions 226) on WGS data of a training set of CCGA subjects.

Step 150 of FIG. 2. The 1502 features derived from the TCGA dataset (first feature extraction functions) and the 20 features derived from the WGS of training subjects in the CCGA dataset (second feature extraction functions) were catenated together to form a total of 1522 feature extraction functions. For each respective subject in the 2000 subjects in the CCGA dataset, for each respective feature extraction function in the 1522 feature extraction functions, the dot product was taken between the normalized WGS bin values of the respective subject and the linear combination of weights of the respective feature extraction function to thereby populate the transformed dataset with a feature value for the respective subject for the respective feature extraction function. In this way, 2000 vectors were obtained for the transformed dataset (hereinafter referred to as the "TCGA+CCGA dataset" to emphasize the transfer learning occurring between the TCGA and CCGA datasets as discussed above. Each vector in the TCGA+CCGA dataset represents a subject in the 2000 subjects of the CCGA dataset and each vector includes 1522 elements, where each element represents the feature value for a corresponding feature extraction function in the 1522 feature extraction function applied to the bin values of the respective subject.

Step 160 of FIG. 2. The 2000 vectors for the 2000 subjects (training set) of the TCGA+CCGA dataset of Step 150 were used to train an L2-regularized logistic regression (first classifier 160) using the known cancer origin labels of the 2000 subjects. This classifier is referred to as the TCGA+CCGA classifier in this example.

Figure 11:
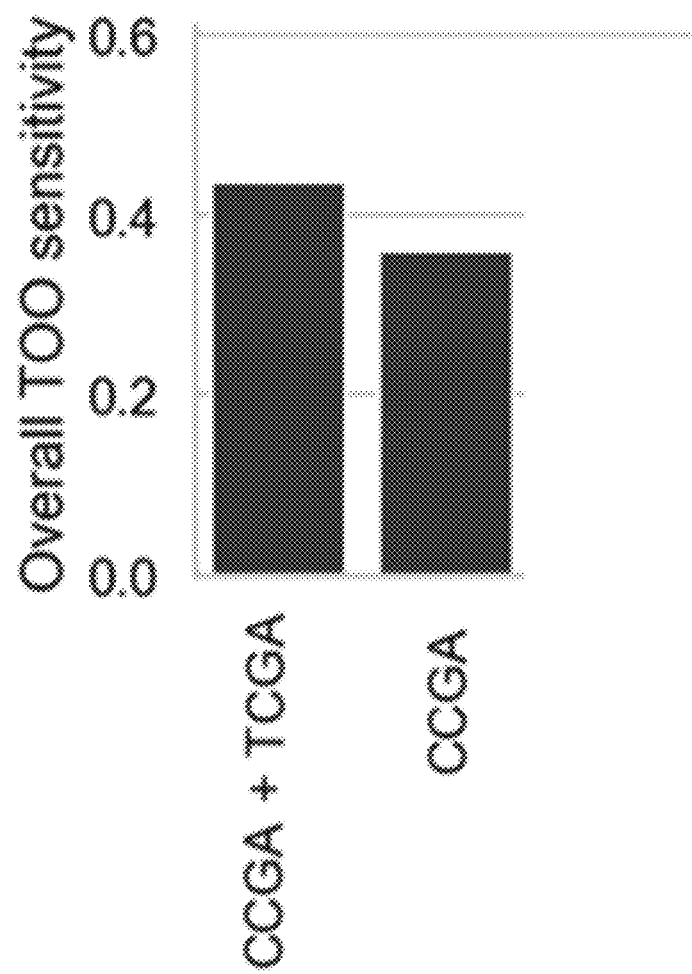
FIG. 11 is a bar chart illustrating a comparison of the ability to discern a tissue of origin (TOO) using a CCGA+ TCGA classifier (left) or a WGS CCGA classifier (right) across a test dataset drawn from the CCGA of Example 2, in accordance with some embodiments of the present disclosure.

Step 214 of FIG. 2. Once trained on the training set, the trained logistic model (TCGA+CCGA classifier) was applied to the test set to produce tissue of origin (TOO) probabilities. Test set data were pre-processed identically to those in the training set (in terms of obtaining and normalizing bin values), except with no knowledge of test set labels (i.e., cancer of origin). There were more than 160 subjects in the test set, and each of the cancers under study in this example were represented in the test set. FIG. 11 illustrates the overall sensitivity of the TCGA+CCGA classifier compared to an approach that employs a classifier trained using WGS CCGA data alone (termed the "CCGA classifier" in FIG. 11). In FIG. 11, sensitivity is scored as the probability that the classifier scored a subject for a particular cancer type given that the subject has that particular cancer type. For instance, in the case of lung cancer, the probability that the classifier identified a subject as having lung cancer when, in fact, they have cancer. For FIG. 11, the specificity is across all the types of cancers considered in the Example. As illustrated in FIG. 11, the transfer learning from the TCGA data improves the performance of the cancer of origin classifier (the TCGA+CCGA classifier in the form of a multinomial logit model from logistic regression) relative to the cancer of origin classifier trained on the WGS CCGA data without the transfer learning (the "CCGA classifier"). Similar results are expected when using a Decision Tree classifier instead of multinomial logistic regression.

FIG. 12 illustrates the results of detection of various types of cancers using the TCGA+CCGA classifier as compared to the WGS CCGA classifier. In FIG. 12, primccat scores ("primary cancer category") is shown for each cancer type. As FIG. 12 shows, in most instances, the TCGA+CCGA classifier selected the true cancer as the number one choice (primccat) more often than the WGS CCGA classifier. For instance, in the case of ovarian cancers in a test dataset drawn from the CCGA cohort, the TCGA+CCGA classifier selected ovarian cancer fifty percent of the time (0.5) when the subject had ovarian cancer whereas the WGS CCGA classifier selected ovarian cancer twenty-five percent of the time (0.25) when the subject had ovarian cancer.

Figure 13:
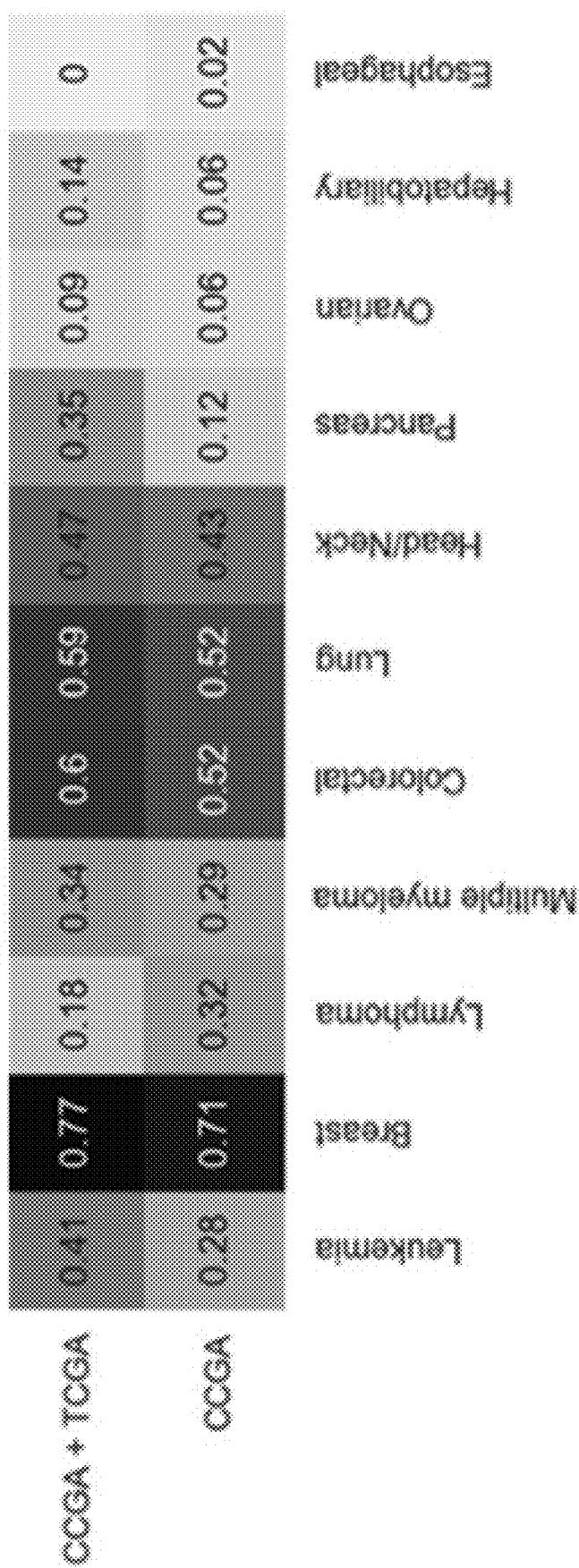
FIG. 13 illustrates positive predictive values across a test dataset drawn from the CCGA study of Example 2 for respective various cancers using a CCGA+TCGA classifier versus a WGS CCGA classifier, in accordance with some embodiments of the present disclosure.

FIG. 13 illustrates positive predictive values (the probability that subjects with a positive screening test truly have the disease) for the TCGA+CCGA classifier versus the WGS CCGA classifier for respective various cancers against a test set of subjects drawn from the CCGA cohort. For instance, of those subjects in the test set of subjects drawn from the CCGA cohort that have head/neck cancer, the TCGA+CCGA classifier identifies 47 percent of such subjects as having head/neck cancer whereas the WGS CCGA classifier identifies 43 percent of such subjects as having head/neck cancer.

Figure 14:
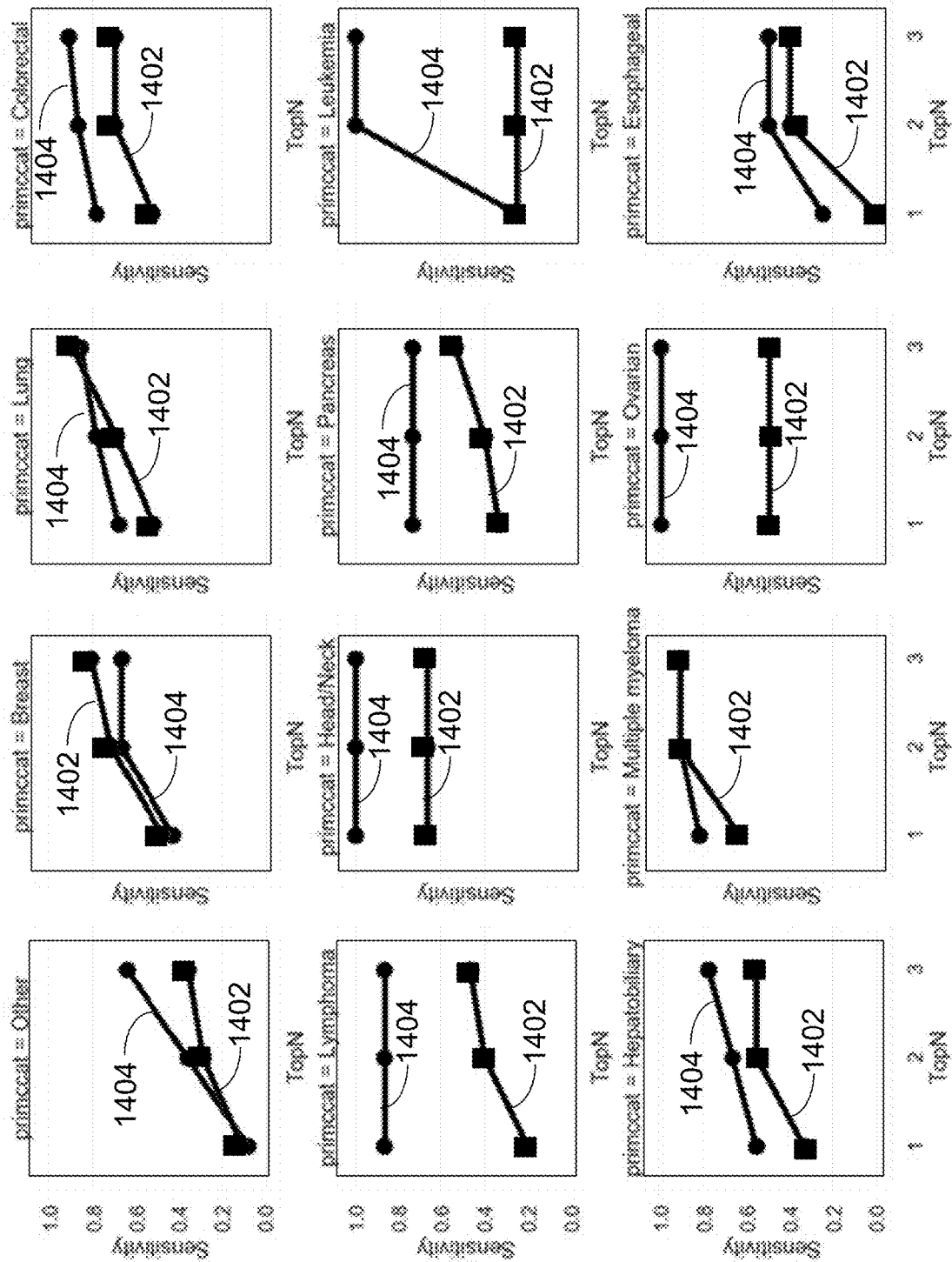
FIG. 14 are graphs illustrating sensitivity of prediction for various cancer types using a WGS CCGA+TCGA classifier versus a WGBS CCGA classifier across a test dataset drawn from the CCGA study of Example 2, in accordance with some embodiments of the present disclosure.

FIG. 14 illustrates sensitivity of prediction for the TCGA+CCGA classifier (lines 1402 in FIG. 14, with round data points) versus a CCGA classifier (lines 1404 in FIG. 14, with square data points) for respective various cancers against a test set of subjects drawn from the CCGA cohort. In FIG. 14, the TopN sensitivity is provided, where N is 1 (top 1), 2 (top 2), or 3 (top 3). For example, if there is only one cancer sample, and it is lung, and if the top three predictions of the classifier (in terms of probability of cancer origin) are 1) Breast, 2) Lung and 3) Colorectal, the top N sensitivities are: top 1: 0%, top 2: 100%, top 3: 100%. For FIG. 14, the CCGA classifier was trained using methylation sequencing data available in the CCGA dataset (WGBS data described in Example 2 above) rather than WGS data. Although the WGBS data generally improved cancer type prediction, performance using the CCGA+TCGA data (based on WGS sequencing) was comparable.

Figure 15:
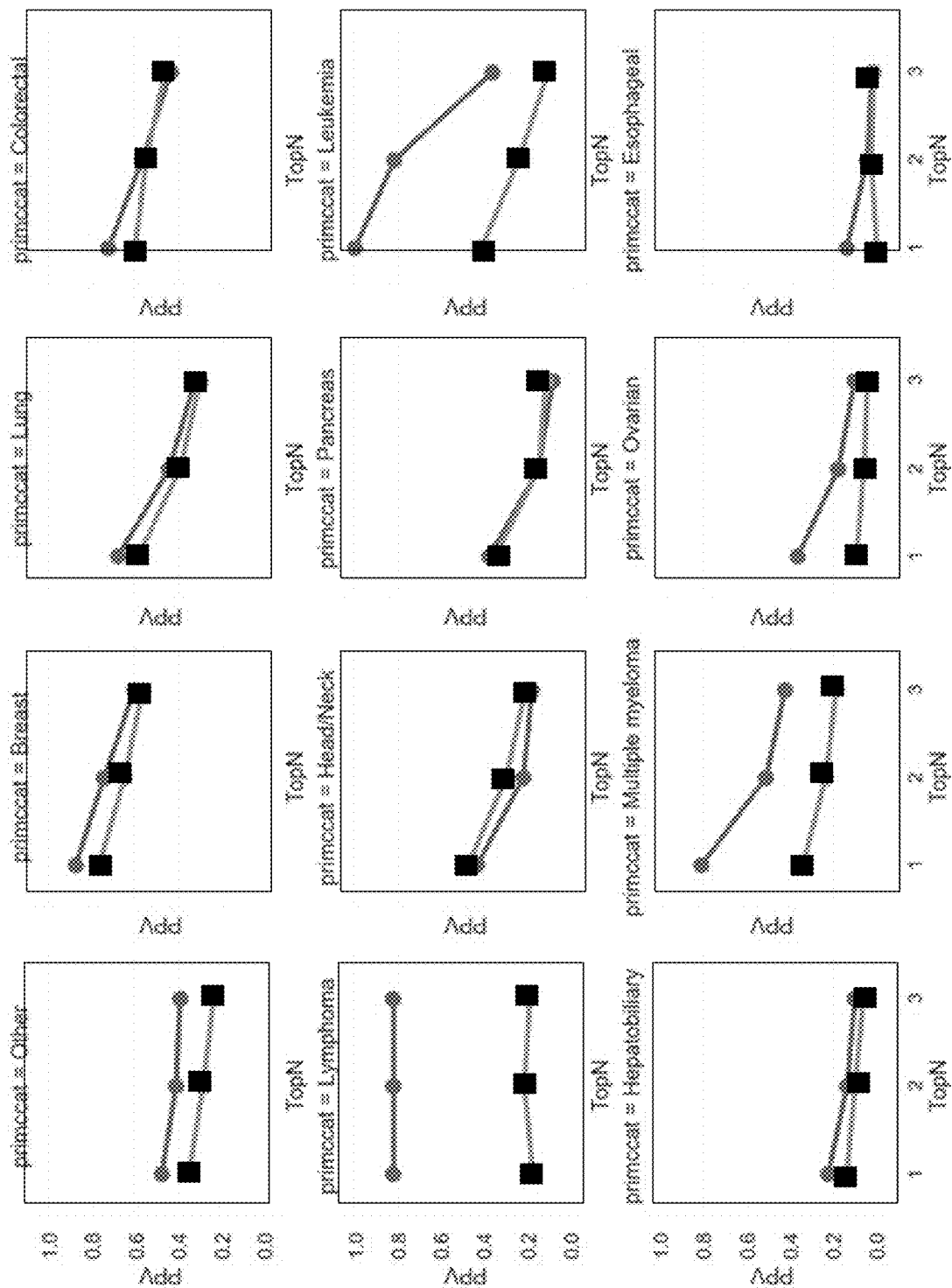
FIG. 15 are graphs illustrating positive predictive values (PPV) for various cancer types using a WGS CCGA+TCGA classifier versus a WGBS CCGA classifier across a test dataset drawn from the CCGA study of Example 2, in accordance with some embodiments of the present disclosure.

FIG. 15 illustrates TopN positive predictive values (ppV) of various cancer types, where like FIG. 14, N is 1, 2 or 3 except now the metric is ppV instead of sensitivity and where, like in FIG. 14, lines with circles represent the CCGA classifier was trained using methylation sequencing data available in the CCGA dataset (WGBS data described in Example 2 above) rather than WGS data and lines with squares represent the CCGA+TCGA (WGS) classifier. As shown, performance using the CCGA+TCGA WGS classifier is comparable to the CCGA WGBS classifier.

Figure 16:
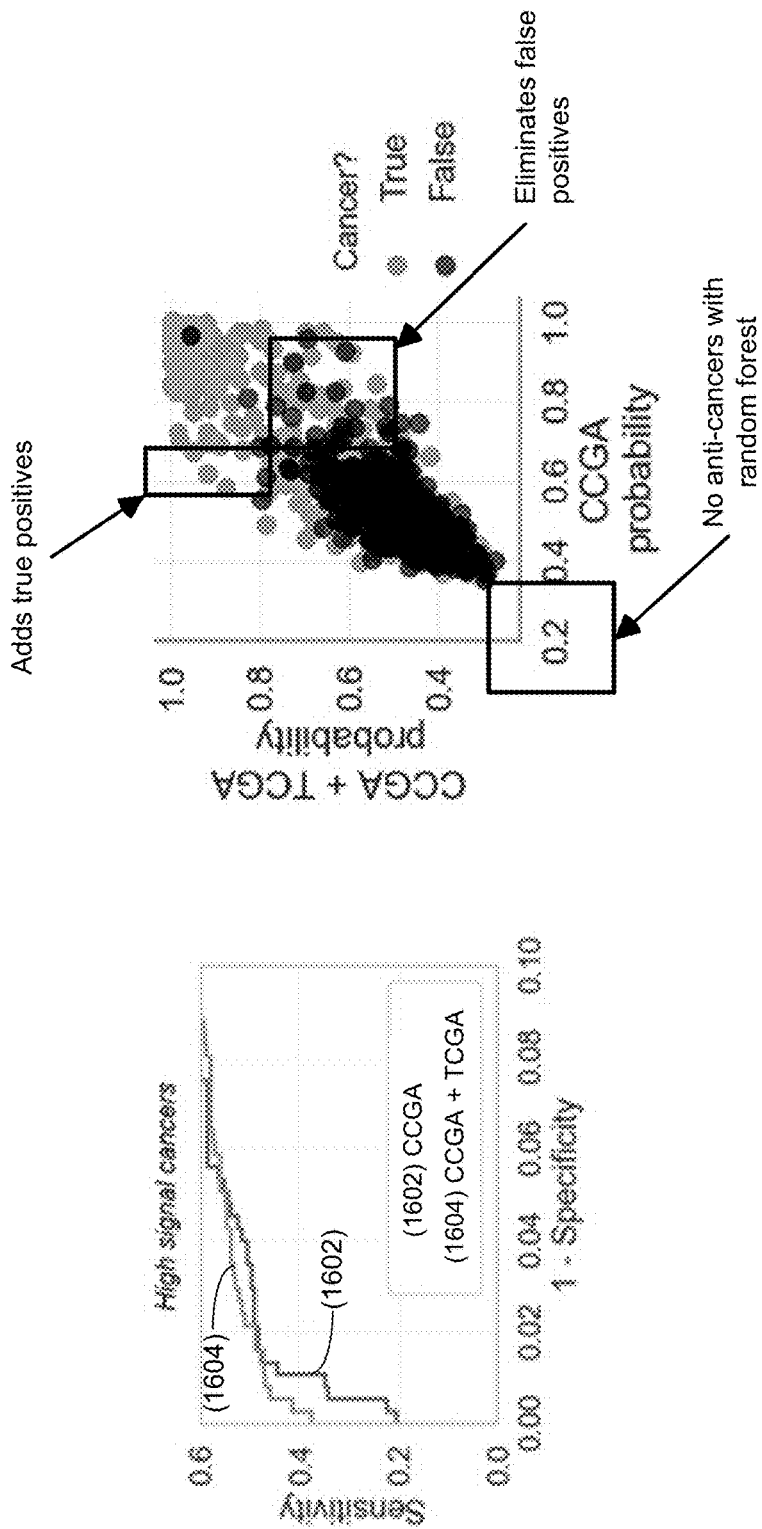
FIG. 16 illustrates application of the methods in accordance with the present disclosure to discriminate between cancer and non-cancer tissue samples. The left graph illustrates Sensitivity vs. (1-Specificity) of prediction of presence of high-signal cancers using the WGS CCGA classifier (line 1602 starting at sensitivity of about 0.2) data, and the WGS CCGA+TCGA transfer learning data classifier (line 1604 starting at sensitivity of about 0.4). The right graph illustrates true (light grey) and false (black) positives resulting from cancer detection using the CCGA+TCGA transfer learning classifier and using the CCGA classifier. As shown in the graph of CCGA+TCGA classifier probability vs. CCGA classifier probability, the disclosed transfer learning approach provides the cancer detection with high sensitivity.

FIG. 16 illustrates application of the methods in accordance with the present disclosure to discriminate between cancer and non-cancer tissue samples. The left graph illustrates Sensitivity vs. (1-Specificity) of prediction of presence of high-signal cancers using the WGS CCGA classifier (line 1602 starting at sensitivity of about 0.2), and using the WGS CCGA+TCGA classifier (line 1604 starting at sensitivity of about 0.4). The right graph illustrates the CCGA+TCGA classifier probability versus the WGS CCGA classifier probability, showing the high sensitivity of cancer detection using the described approach. In this graph, true positives are shown as light grey circles, whereas false positives are shown as black circles. The majority of the true positives are located in the upper right part of the graph, and the majority of the false positives are located in the lower left part of the graph. FIG. 16 illustrates that the WGS CCGA+TCGA transfer learning classifier reduces the number of false positives, increases the number of true positives, and nearly doubles the overall performance of detection of high signal cancers. As used herein, the high signal cancer is any cancer other than uterine thyroid, HR+stage I/II breast cancer, and prostate cancer.

Example 4: Example Bins for Methylation Embodiments

In some embodiments the bins of the present disclosure are designed to encompass only targeted regions of the human genome. This example summarizes the identification of suitable regions of the human genome to be encompassed by such bins. Based on the results of Example 2, as further described in Liu et al., "Sensitive and specific multi-cancer detection and localization using methylation signatures in cell-free DNA," Ann. Oncol 2020, https://doi.org/10.1016/j.annonc.2020.02.011, the portions of the human genome (the hg19 genome, Vogelstin et al., 2013, "Cancer genome landscapes," Science 339 1546-1558) predicted to contain cancer- and/or tissue-specific methylation patterns in cfDNA relative to non-cancer controls were identified and the most informative regions selected to be represented by the bins of one embodiment of the present disclosure.

Specifically, after bisulfite treatment, targeted cfDNA fragments containing abnormal methylation patterns relative to non-cancer controls from both strands were enriched using biotinylated probes. Briefly, 120-bp biotinylated DNA probes were designed to target enrichment of bisulfite-converted DNA from either hypermethylated fragments (100% methylated CpGs) or hypomethylated fragments (100% unmethylated CpGs); probes tiled target regions with 50% overlap between adjacent probes. A custom algorithm aligned candidate probes to the genome and scored the number of on- and off-target mapping events. Probes with elevated off-target mapping were omitted from the final panel of regions to be represented by the bins of one embodiment of the present disclosure.

As disclosed in U.S. patent application Ser. No. 15/931,022, entitled "Model Based Featurization and Classification," filed May 13, 2020, a targeted methylation panel, all or a portion of which is represented by the bins of one embodiment of the present disclosure, covering 103,456 distinct regions (17.2 Mb), covering 1,116,720 CpGs was identified using the whole genome bisulfite data obtained from CCGA sub-study CCGA-1. This included 363,033 CpGs in 68,059 regions (7.5 Mb) covered by probes targeting hypomethylated fragments; 585,181 CpGs in 28,521 regions (7.4 Mb) covered by probes targeting hypermethylated fragments; and 218,506 CpGs in 6,876 regions (2.3 Mb) targeting both types of fragments. Individual abnormal target regions contained between 1 and 590 CpGs, with a median CpG count of 3 for hypomethylated target regions and 6 for hypermethylated target regions. CpGs were present in the following genomic regions using the nomenclature of Cavalcante and Sartor, 2017, "annotatr: genomic regions in context," Bioinformatics33(15):2381-2383: 193,818 (17%) in the region 1 to 5 kbp upstream of transcription start sites (TSSs); 278,872 (24%) in promoters (<1 kbp upstream of TSSs); 500,996 (43%) in introns; 292,789 (25%) in exons; 247,752 (21%) in intron-exon boundaries (i.e., 200 bp up- or down-stream of any boundary between an exon and intron; boundaries are with respect to the strand of the gene); 134,144 (11%) in 5'-untranslated regions; 28,388 (2.4%) in 3'-untranslated regions; 182,174 (16%) between genes; and the remaining 1,817 (<1%) were not annotated. Percentages were relative to the total number of CpGs and do not sum to 100% because each CpG could receive multiple annotations due to overlapping genes and/or transcripts.

Example 5: P-Value Filtering—Assigning a P-Value to Fragments Based on Their Methylation State In some embodiments a p-value for the corresponding methylation state vector of each respective fragment represented by an observed plurality of sequence reads is compared to methylation state vectors from fragments in a healthy control group. See, for example, U.S. patent application Ser. No. 15/931,022, entitled "Model Based Featurization and Classification," filed May 13, 2020, which is hereby incorporated by reference. The p-value score describes a probability of observing a nucleic acid molecule having the methylation status matching that methylation state vector in the healthy control group. In order to determine a fragment is anomalously methylated (by virtue of its p-value being below a certain p-value threshold), a healthy control group (a cohort of non-cancer subjects) with a majority of fragments that are normally methylated is used. When conducting this probabilistic analysis for determining anomalous fragments, the determination holds weight in comparison with the group of control subjects that make up the healthy control group. To ensure robustness in the healthy control group, some threshold number of healthy individuals to source samples including DNA fragments is used (cohort of non-cancer subjects).

In some embodiments, a healthy control group data structure for a healthy control group (a cohort of non-cancer subjects) is created. To create a healthy control group data structure, a plurality of fragments (e.g., cfDNA) from a plurality of healthy individuals is obtained. A method 2100 of generating a data structure for a healthy control group with which p-value scores are calculated is described below in conjunction with FIG. 21. A method of calculating a p-value score with the generated data structure is described below in conjunction with FIG. 22.

FIG. 21 is a flowchart describing a process 2100 of generating a data structure for a healthy control group, according to an embodiment of the present disclosure. To create a healthy control group data structure, a plurality of DNA fragments (e.g., cfDNA) from a plurality of healthy individuals is obtained. A methylation state vector 2052 is identified for each fragment, for example via the process illustrated in FIGS. 18 and 19 in conjunction with Example 10 below.

With each fragment's methylation state vector 2052, the methylation state vector is subdivided into strings of CpG sites 2105. In one embodiment, the methylation state vector 2052 is subdivided such that the resulting strings are all less than a given length. For example, a methylation state vector 2052 of length 11 may be subdivided into strings of length less than or equal to 3 would result in 9 strings of length 3, 10 strings of length 2, and 11 strings of length 1. In another example, a methylation state vector of length 7 is subdivided into strings of length less than or equal to 4 would result in 4 strings of length 4, 5 strings of length 3, 6 strings of length 2, and 7 strings of length 1. If a methylation state vector 2052 is shorter than or the same length as the specified string length, then the methylation state vector may be converted into a single string containing all of the CpG sites of the vector.

The strings are tallied by counting 2110, for each possible CpG site and possibility of methylation states in the vector 2052, the number of strings present in the control group having the specified CpG site as the first CpG site in the string and having that possibility of methylation states. For example, at a given CpG site and considering string lengths of 3, there are $2^3$ or 8 possible string configurations. At that given CpG site, for each of the 8 possible string configurations, a tally is made of how many occurrences of each methylation state vector 2052 possibility come up in the control group. Continuing this example, this may involve tallying the following quantities: $<M_x, M_{x+1}, M_{x+2}>$, $<M_x, M_{x+1}, U_{x+2}>$, . . . , $<U_x, U_{x+1}, U_{x+2}>$ for each starting CpG site x in the reference genome. The data structure stores the tallied counts for each starting CpG site and string possibility 2115.

There are several benefits to setting an upper limit on string length. First, depending on the maximum length for a string, the size of the data structure can dramatically increase in size. For instance, maximum string length of 4 means that every CpG site has at the very least $2^4$ numbers to tally for strings of length 4. Increasing the maximum string length to 5 means that every CpG site has an additional $2^4$ or 16 numbers to tally, doubling the numbers to tally (and computer memory required) compared to the prior string length. Reducing string size helps keep the data structure creation and performance (e.g., use for later accessing as described below), in terms of computational and storage, reasonable. Second, a statistical consideration to limiting the maximum string length is to avoid overfitting downstream models that use the string counts. If long strings of CpG sites do not, biologically, have a strong effect on the outcome (e.g., predictions of anomalousness that predictive of the presence of cancer), calculating probabilities based on large strings of CpG sites can be problematic as it requires a significant amount of data that may not be available, and thus would be too sparse for a model to perform appropriately. For example, calculating a probability of anomalousness/cancer conditioned on the prior 100 CpG sites would require counts of strings in the data structure of length 100, ideally some matching exactly the prior 100 methylation states. If only sparse counts of strings of length 100 are available, there will be insufficient data to determine whether a given string of length of 100 in a test sample is anomalous or not.

Figure 22:
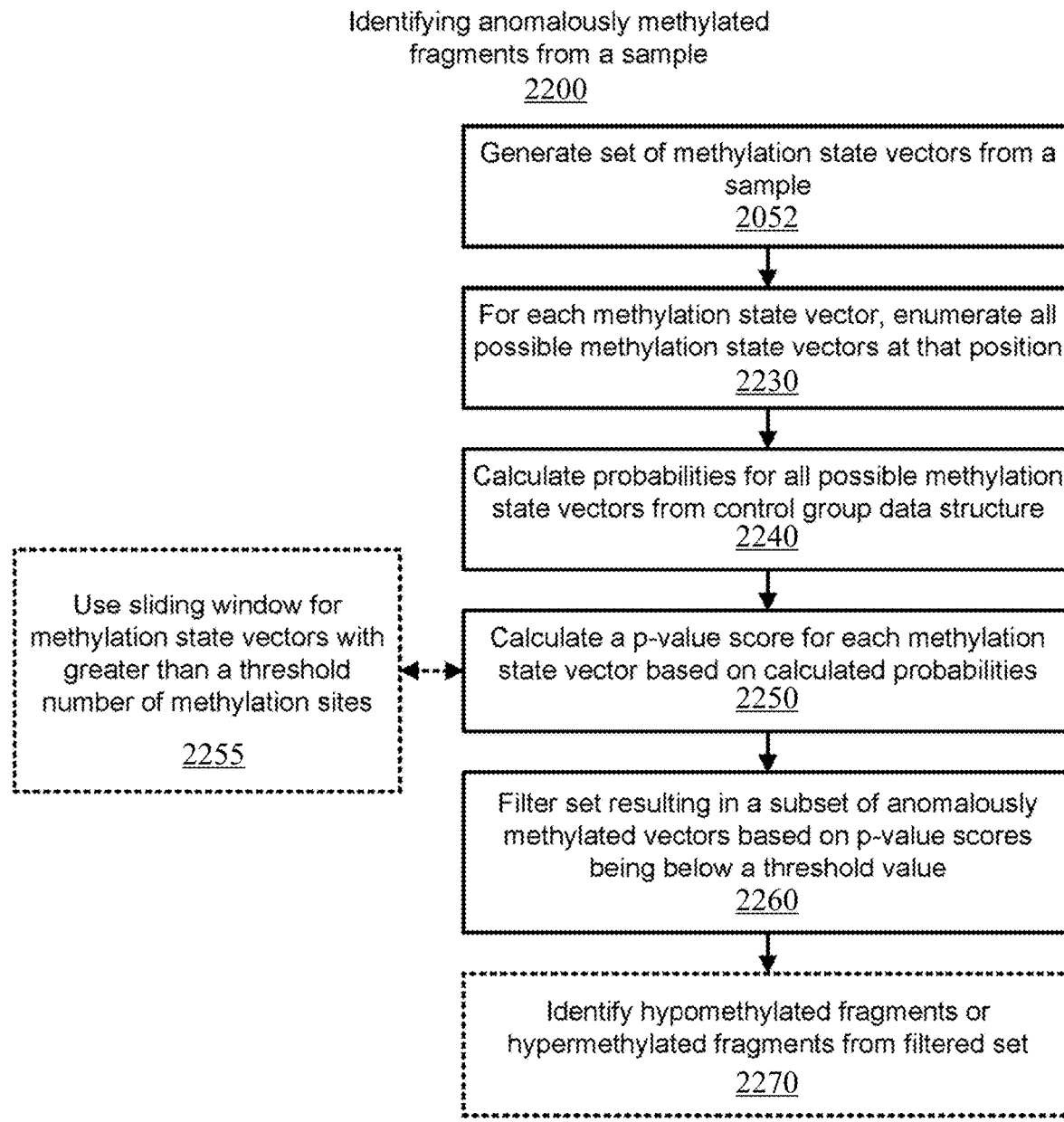
FIG. 22 illustrates a flowchart describing a process of determining anomalously methylated fragments from a sample, in accordance with an aspect of the present disclosure.

FIG. 22 is a flowchart describing a process 2200 for identifying anomalously methylated fragments from an individual, according to an embodiment. In process 2200, methylation state vectors 2052 are generated from cfDNA fragments of the subject using the methods disclosed in Example 10 in conjunction with FIGS. 19 and 20. Each methylation state vector 2052 is processed as follows.

For a given methylation state vector 2052, all possibilities of methylation state vectors having the same starting CpG site and same length (e.g., set of CpG sites) in the methylation state vector are enumerated 2230. As each methylation state is generally either methylated or unmethylated there are effectively two possible states at each CpG site, and thus the count of distinct possibilities of methylation state vectors depends on a power of 2, such that a methylation state vector of length n would be associated with $2^n$ possibilities of methylation state vectors. With methylation state vectors inclusive of indeterminate states for one or more CpG sites, possibilities of methylation state vectors are enumerated considering only CpG sites that have observed states.

The probability of observing each possibility of methylation state vector for the identified starting CpG site and methylation state vector length are determined by accessing the healthy control group data structure 2240. In one embodiment, calculating the probability of observing a given possibility uses a Markov chain probability to model the joint probability calculation. In one such approach, a Markov Chain model based on methylation states was derived from a cohort of 131 non-cancer participants (not included in the CCGA study of Example 2) and used to assign a p-value to each fragment, representing the probability of observing the fragment's methylation states in non-cancer cfDNA. See Liu et al., "Sensitive and specific multi-cancer detection and localization using methylation signatures in cell-free DNA," Ann. Oncol 2020, https://doi.org/10.1016/j.annonc.2020.02.011, which is hereby incorporated by reference. In other embodiments, calculation methods other than Markov chain probabilities are used to determine the probability of observing each possibility of methylation state vector.

In some embodiments, a p-value score is calculated for the methylation state vector 2052 using the calculated probabilities for each possibility 2250. In one embodiment, this includes identifying the calculated probability corresponding to the possibility that matches the methylation state vector in question. Specifically, this is the possibility of having the same set of CpG sites or, similarly, the same starting CpG site and length as the methylation state vector. The calculated sums probabilities of any possibilities having probabilities less than or equal to the identified probability to generate the p-value score.

This p-value represents the probability of observing the methylation state vector 2052 of the fragment or other methylation state vectors even less probable in the healthy control group. A low p-value score generally corresponds to a methylation state vector which is rare in a healthy individual, and causes the fragment to be labeled anomalously methylated, relative to the healthy control group. A high p-value score generally relates to a methylation state vector that is expected to be present, in a relative sense, in a healthy individual. If the healthy control group is a non-cancerous group, for example, a low p-value indicates that the fragment is anomalous methylated relative to the non-cancer group, and therefore possibly indicative of the presence of cancer in the test subject.

The p-value scores are calculated for each of a plurality of methylation state vectors, each representing a cfDNA fragment in the test sample. To identify which of the fragments are anomalously methylated, the set of methylation state vectors are filtered based on their p-value scores 2260. In one embodiment, filtering is performed by comparing the p-values scores against a threshold and keeping only those fragments below the threshold. This threshold p-value score could be on the order of 0.1, 0.01, 0.001, 0.0001, or similar.

According to example results from the process, a median (range) of 2,800 (1,500-12,000) fragments with anomalous methylation patterns for participants without cancer in training, and a median (range) of 3,000 (1,200-220,000) fragments with anomalous methylation patterns for participants with cancer in training. These filtered sets of fragments with anomalous methylation patterns may be used for the downstream analyses as described herein.

In one embodiment, a sliding window is used to determine possibilities of methylation state vectors and calculate p-values 2255. Rather than enumerating possibilities and calculating p-values for entire methylation state vectors, the possibilities are enumerated and p-values calculated for only a window of sequential CpG sites, where the window is shorter in length (of CpG sites) than at least some fragments (otherwise, the window would serve no purpose). The window length may be static, user determined, dynamic, or otherwise selected.

In calculating p-values for a methylation state vector larger than the window, the window identifies the sequential set of CpG sites from the vector within the window starting from the first CpG site in the vector. A p-value score is calculated for the window including the first CpG site. The window is then "slid" to the second CpG site in the vector, and another p-value score is calculated for the second window. Thus, for a window size l and methylation vector length m, each methylation state vector will generate m−l+1 p-value scores. After completing the p-value calculations for each portion of the vector, the lowest p-value score from all sliding windows is taken as the overall p-value score for the methylation state vector. In another embodiment, the p-value scores are aggregated for the methylation state vectors to generate an overall p-value score.

Using the sliding window helps to reduce the number of enumerated possibilities of methylation state vectors and their corresponding probability calculations that would otherwise need to be performed. To give a realistic example, it is possible for fragments to have upwards of 54 CpG sites. Instead of computing probabilities for $2^{54}$ ($\wedge 1.8 \times 10^{16}$) possibilities to generate a single p-score, a window of size 5 CpG sites (for example) can be used, resulting in 50 p-value calculations for each of the 50 windows of the methylation state vector for that fragment. Each of the 50 calculations enumerates $2^5$ (32) possibilities of methylation state vectors, which total results in $50 \times 2^5$ ($1.6 \times 10^3$) probability calculations. This results in a vast reduction of calculations to be performed, with no meaningful hit to the accurate identification of anomalous fragments.

In embodiments with indeterminate states at some or all of their CpG sites, a p-value score is calculated by summing out CpG sites with indeterminate states in a fragment's methylation state vector. All possibilities that have consensus with the all methylation states of the methylation state vector excluding the indeterminate states is determined. A probability is assigned to the methylation state vector as a sum of the probabilities of the identified possibilities. As an example, a probability of a methylation state vector of $<M_1, I_2, U_3>$ is calculated as a sum of the probabilities for the possibilities of methylation state vectors of $<M_1, M_2, U_3>$ and $<M_1, U_2, U_3>$ since methylation states for CpG sites 1 and 3 are observed and in consensus with the fragment's methylation states at CpG sites 1 and 3. This method of summing out CpG sites with indeterminate states uses calculations of probabilities of possibilities up to $2^i$, where i denotes the number of indeterminate states in the methylation state vector. In additional embodiments, a dynamic programming algorithm may be implemented to calculate the probability of a methylation state vector with one or more indeterminate states. Advantageously, the dynamic programming algorithm operates in linear computational time.

In some embodiments, the computational burden of calculating probabilities and/or p-value scores is further reduced by caching at least some calculations. For example, calculations of probabilities for possibilities of methylation state vectors (or windows thereof) can be cached in transitory or persistent memory. If other fragments have the same CpG sites, caching the possibility probabilities allows for efficient calculation of p-score values without needing to re-calculate the underlying possibility probabilities. Equivalently, p-value scores can be calculated for each of the possibilities of methylation state vectors associated with a set of CpG sites from vector (or window thereof). The p-value scores can be cached for use in determining the p-value scores of other fragments including the same CpG sites. Generally, the p-value scores of possibilities of methylation state vectors having the same CpG sites may be used to determine the p-value score of a different one of the possibilities from the same set of CpG sites.

In some embodiments, anomalous fragments are identified as fragments with over a threshold number of CpG sites and either with over a threshold percentage of the CpG sites methylated (hypermethylated) or with over a threshold percentage of CpG sites unmethylated (hypomethylated) 2270. Example thresholds for length of fragments (or CpG sites) include more than 3, 4, 5, 6, 7, 8, 9, 10, etc. Example percentage thresholds of methylation or unmethylation include more than 80%, 85%, 90%, or 95%, or any other percentage within the range of 50%-100%.

Example 6: Cancer Assay Probes and Panels

In various embodiments, the predictive cancer models described herein use samples enriched using a cancer assay panel comprising a plurality of probes or a plurality of probe pairs. A number of targeted cancer assay panels are known in the art, for example, as described in WO 2019/195268 entitled "Methylation Markers and Targeted Methylation Probe Panels," filed Apr. 2, 2019, PCT/US2019/053509, filed Sep. 27, 2019 and PCT/US2020/015082 entitled "Detecting Cancer, Cancer Tissue or Origin, or Cancer Type," filed Jan. 24, 2020 (which are each incorporated by reference herein in their entirety). For example, in some embodiments, the cancer assay panel can be designed to include a plurality of probes (or probe pairs) that can capture fragments that can together provide information relevant to diagnosis of cancer. In some embodiments, a panel includes at least 50, 100, 500, 1,000, 2,000, 2,500, 5,000, 6,000, 7,500, 10,000, 15,000, 20,000, 25,000, or 50,000 pairs of probes. In other embodiments, a panel includes at least 500, 1,000, 2,000, 5,000, 10,000, 12,000, 15,000, 20,000, 30,000, 40,000, 50,000, or 100,000 probes. The plurality of probes together can comprise at least 0.1 million, 0.2 million, 0.4 million, 0.6 million, 0.8 million, 1 million, 2 million, 3 million, 4 million, 5 million, 6 million, 7 million, 8 million, 9 million, or 10 million nucleotides. The probes (or probe pairs) are specifically designed to target one or more genomic regions differentially methylated in cancer and non-cancer samples. The target genomic regions can be selected to maximize classification accuracy, subject to a size budget (which is determined by sequencing budget and desired depth of sequencing).

Samples enriched using a cancer assay panel can be subject to targeted sequencing. Samples enriched using the cancer assay panel can be used to detect the presence or absence of cancer generally and/or provide a cancer classification such as cancer type, stage of cancer such as I, II, III, or IV, or provide the tissue of origin where the cancer is believed to originate. Depending on the purpose, a panel can include probes (or probe pairs) targeting genomic regions differentially methylated between general cancerous (pan-cancer) samples and non-cancerous samples, or only in cancerous samples with a specific cancer type (e.g., lung cancer-specific targets). Specifically, a cancer assay panel is designed based on bisulfite sequencing data generated from the cell-free DNA (cfDNA) or genomic DNA (gDNA) from cancer and/or non-cancer individuals.

In some embodiments, the cancer assay panel designed by methods provided herein comprises at least 1,000 pairs of probes, each pair of which comprises two probes configured to overlap each other by an overlapping sequence comprising a 30-nucleotide fragment. The 30-nucleotide fragment comprises at least five CpG sites, wherein at least 80% of the at least five CpG sites are either CpG or UpG. The 30-nucleotide fragment is configured to bind to one or more genomic regions in cancerous samples, wherein the one or more genomic regions have at least five methylation sites with an abnormal methylation pattern. Another cancer assay panel comprises at least 2,000 probes, each of which is designed as a hybridization probe complimentary to one or more genomic regions. Each of the genomic regions is selected based on the criteria that it comprises (i) at least 30 nucleotides, and (ii) at least five methylation sites, wherein the at least five methylation sites have an abnormal methylation pattern and are either hypomethylated or hypermethylated.

Each of the probes (or probe pairs) is designed to target one or more target genomic regions. The target genomic regions are selected based on several criteria designed to increase selective enriching of relevant cfDNA fragments while decreasing noise and non-specific bindings. For example, a panel can include probes that can selectively bind and enrich cfDNA fragments that are differentially methylated in cancerous samples. In this case, sequencing of the enriched fragments can provide information relevant to diagnosis of cancer. Furthermore, the probes can be designed to target genomic regions that are determined to have an abnormal methylation pattern and/or hypermethylation or hypomethylation patterns to provide additional selectivity and specificity of the detection. For example, genomic regions can be selected when the genomic regions have a methylation pattern with a low p-value according to a Markov model trained on a set of non-cancerous samples, that additionally cover at least 5 CpG's, 90% of which are either methylated or unmethylated. In other embodiments, genomic regions can be selected utilizing mixture models, as described herein.

Each of the probes (or probe pairs) can target genomic regions comprising at least 25 bp, 30 bp, 35 bp, 40 bp, 45 bp, 50 bp, 60 bp, 70 bp, 80 bp, or 90 bp. The genomic regions can be selected by containing less than 20, 15, 10, 8, or 6 methylation sites. The genomic regions can be selected when at least 80, 85, 90, 92, 95, or 98% of the at least five methylation (e.g., CpG) sites are either methylated or unmethylated in non-cancerous or cancerous samples.

Genomic regions may be further filtered to select only those that are likely to be informative based on their methylation patterns, for example, CpG sites that are differentially methylated between cancerous and non-cancerous samples (e.g., abnormally methylated or unmethylated in cancer versus non-cancer). For the selection, calculation can be performed with respect to each CpG site. In some embodiments, a first count is determined that is the number of cancer-containing samples (cancer_count) that include a fragment overlapping that CpG, and a second count is determined that is the number of total samples containing fragments overlapping that CpG (total). Genomic regions can be selected based on criteria positively correlated to the number of cancer-containing samples (cancer_count) that include a fragment overlapping that CpG, and inversely correlated with the number of total samples containing fragments overlapping that CpG (total).

In one embodiment, the number of non-cancerous samples ($n_{non-cancer}$) and the number of cancerous samples ($n_{cancer}$) having a fragment overlapping a CpG site are counted. Then the probability that a sample is cancer is estimated, for example as $(n_{cancer}+1)/(n_{cancer}+n_{non-cancer}+2)$. CpG sites by this metric are ranked and greedily added to a panel until the panel size budget is exhausted.

Depending on whether the assay is intended to be a pan-cancer assay or a single-cancer assay, or depending on what kind of flexibility is desired when picking which CpG sites are contributing to the panel, which samples are used for cancer-count can vary. A panel for diagnosing a specific cancer type (e.g., TOO) can be designed using a similar process. In this embodiment, for each cancer type, and for each CpG site, the information gain is computed to determine whether to include a probe targeting that CpG site. The information gain is computed for samples with a given cancer type compared to all other samples. For example, two random variables, "AF" and "CT". "AF" is a binary variable that indicates whether there is an abnormal fragment overlapping a particular CpG site in a particular sample (yes or no). "CT" is a binary random variable indicating whether the cancer is of a particular type (e.g., lung cancer or cancer other than lung). One can compute the mutual information with respect to "CT" given "AF." That is, how many bits of information about the cancer type (lung vs. non-lung in the example) are gained if one knows whether there is an anomalous fragment overlapping a particular CpG site. This can be used to rank CpG's based on how specific they are for a particular cancer type (e.g., TOO). This procedure is repeated for a plurality of cancer types. For example, if a particular region is commonly differentially methylated only in lung cancer (and not other cancer types or non-cancer), CpG's in that region would tend to have high information gains for lung cancer. For each cancer type, CpG sites ranked by this information gain metric, and then greedily added to a panel until the size budget for that cancer type was exhausted.

Further filtration can be performed to select target genomic regions that have off-target genomic regions less than a threshold value. For example, a genomic region is selected only when there are less than 15, 10 or 8 off-target genomic regions. In other cases, filtration is performed to remove genomic regions when the sequence of the target genomic regions appears more than 5, 10, 15, 20, 25, or 30 times in a genome. Further filtration can be performed to select target genomic regions when a sequence, 90%, 95%, 98% or 99% homologous to the target genomic regions, appear less than 15, 10 or 8 times in a genome, or to remove target genomic regions when the sequence, 90%, 95%, 98% or 99% homologous to the target genomic regions, appear more than 5, 10, 15, 20, 25, or 30 times in a genome. This is for excluding repetitive probes that can pull down off-target fragments, which are not desired and can impact assay efficiency.

In some embodiments, fragment-probe overlap of at least 45 bp was demonstrated to be required to achieve a non-negligible amount of pulldown (though this number can be different depending on assay details). Furthermore, it has been suggested that more than a 10% mismatch rate between the probe and fragment sequences in the region of overlap is sufficient to greatly disrupt binding, and thus pulldown efficiency. Therefore, sequences that can align to the probe along at least 45 bp with at least a 90% match rate are candidates for off-target pulldown. Thus, in one embodiment, the number of such regions are scored. The best probes have a score of 1, meaning they match in only one place (the intended target region). Probes with a low score (say, less than 5 or 10) are accepted, but any probes above the score are discarded. Other cutoff values can be used for specific samples.

In various embodiments, the selected target genomic regions can be located in various positions in a genome, including but not limited to exons, introns, intergenic regions, and other parts. In some embodiments, probes targeting non-human genomic regions, such as those targeting viral genomic regions, can be added.

Example 7: Select Human Genomic Regions Used for Bins

In some embodiments of the present disclosure, each bin in the plurality of bins is drawn from a panel of genomic regions that is designed for targeted selection of cancer-specific methylation patterns. In some embodiments, each such genomic region is drawn from Table 2 of International Patent Application No. PCT/US2020/015082, entitled "Detecting Cancer, Cancer Tissue or Origin, or Cancer Type," filed Jan. 24, 2020, which is hereby incorporated by reference, including the Sequence Listing referenced therein), reproduced below:

| List | Target Genomic Regions | SEQ ID Nos First | SEQ ID Nos Last | Panel Size (Mb) |
| --- | --- | --- | --- | --- |
| 1 | 34844 | 1 | 34844 | 6.43 |
| 2 | 67431 | 34845 | 102275 | 12.14 |
| 3 | 94955 | 102276 | 197230 | 17.72 |
| 4 | 23941 | 197231 | 221171 | 4.63 |
| 5 | 56624 | 221172 | 277795 | 16.42 |
| 6 | 52850 | 277796 | 330645 | 10.45 |
| 7 | 14284 | 330646 | 344929 | 8.48 |
| 8 | 1370 | 344930 | 346299 | 0.39 |
| 9 | 2842 | 346300 | 349141 | 0.79 |
| 10 | 7483 | 349142 | 356624 | 1.94 |
| 11 | 12328 | 356625 | 368952 | 3.08 |
| 12 | 14725 | 368953 | 383677 | 3.65 |
| 13 | 3814 | 383678 | 387491 | 0.62 |
| 14 | 7730 | 387492 | 395221 | 1.26 |
| 15 | 19424 | 395222 | 414645 | 3.23 |
| 16 | 38061 | 414646 | 452706 | 6.58 |

SEQ ID NOs 452,706-483,478 of PCT/US2020/015082 provide further information about certain hypermethylated or hypomethylated target genomic regions. These SEQ ID NO records identify target genomic regions that can be differentially methylated in samples from specified pairs of cancer types. The target genomic regions of SEQ ID NOs 452,706-483,478 of PCT/US2020/015082 are drawn from list 6 of PCT/US2020/015082. Many of the same target genomic regions are also found in lists 1-5 and 7-16 of PCT/US2020/015082. The entry for each SEQ ID indicates the chromosomal location of the target genomic region relative to hg19, whether cfDNA fragments to be enriched from the region are hypermethylated or hypomethylated, the sequence of one DNA strand of the target genomic region, and the pair or pairs of cancer types that are differentially methylated in that genomic region. As the methylation status of some target genomic regions distinguish more than one pair of cancer types, each entry identifies a first cancer type as indicated in TABLE 3 of PCT/US2020/015082, including the Sequence Listing referenced therein and one or more second cancer types.

In some embodiments, the plurality of bins of the present disclosure includes a separate bin for each of at 200, 500, 1,000, 5,000, 10,000, 15,000, 20,000, 30,000, 40,000, or 50,000 target genomic regions in any one of lists 1-16 of PCT/US2020/015082.

In some embodiments, the plurality of bins of the present disclosure includes a separate bin for each of at least 20%, 30%, 40%, 50%, 60%, 70%, 80%, 90% or 95% of the target genomic regions in any one of lists 1-16 of PCT/US2020/015082.

In some embodiments, the plurality of bins of the present disclosure includes a separate bin for each of at 200, 500, 1,000, 5,000, 10,000, 15,000, 20,000, 30,000, 40,000, or 50,000 target genomic regions in any combination of lists 1-16 of PCT/US2020/015082.

In some embodiments, the plurality of bins of the present disclosure includes a separate bin for each of at least 20%, 30%, 40%, 50%, 60%, 70%, 80%, 90% or 95% of the target genomic regions in any combination of lists 1-16 of PCT/US2020/015082.

In some embodiments, the plurality of bins of the present disclosure includes a separate bin for each of at least 200, 500, 1,000, 5,000, 10,000, 15,000, 20,000, 30,000, 40,000, or 50,000 target genomic regions in any one of lists 1-3 of PCT/US2020/015082.

In some embodiments, the plurality of bins of the present disclosure includes a separate bin for each of at least 20%, 30%, 40%, 50%, 60%, 70%, 80%, 90% or 95% of the target genomic regions in any one of lists 1-3 of PCT/US2020/015082.

In some embodiments, the plurality of bins of the present disclosure includes a separate bin for at least 200, 500, 1,000, 5,000, 10,000, 15,000, 20,000, 30,000, 40,000, or 50,000 target genomic regions in any one of lists 13-16 of PCT/US2020/015082.

In some embodiments, the plurality of bins of the present disclosure includes a separate bin for each of at least 10%, 20%, 25%, 30%, 40%, 50%, 60%, 70%, 80%, 90% or 95% of the target genomic regions in any one of lists 13-16 of PCT/US2020/015082.

In some embodiments, the plurality of bins of the present disclosure includes a separate bin for each of at least 200, 500, 1,000, 5,000, 10,000, 15,000, 20,000, 30,000, 40,000, or 50,000 target genomic regions selected from list 12 of PCT/US2020/015082.

In some embodiments, the plurality of bins of the present disclosure includes a separate bin for each of at least 10%, 20%, 25%, 30%, 40%, 50%, 60%, 70%, 80%, 90% or 95% of the target genomic regions in list 12 of PCT/US2020/015082.

In some embodiments, the plurality of bins of the present disclosure includes a separate bin for each of at least 200, 500, 1,000, 5,000, 10,000, 15,000, 20,000, 30,000, 40,000, or 50,000 target genomic regions selected from any one of lists 8-11 of PCT/US2020/015082.

In some embodiments, the plurality of bins of the present disclosure includes a separate bin for each of at least 10%, 20%, 25%, 30%, 40%, 50%, 60%, 70%, 80%, 90% or 95% of the target genomic regions in any one of lists 8-11 of PCT/US2020/015082.

In some embodiments, the plurality of bins of the present disclosure includes a separate bin for each of at least 200, 500, 1,000, 5,000, 10,000, 15,000, 20,000, 30,000, 40,000, or 50,000 target genomic regions selected from list 4 of PCT/US2020/015082.

In some embodiments, the plurality of bins of the present disclosure includes a separate bin for each of at least 10%, 20%, 25%, 30%, 40%, 50%, 60%, 70%, 80%, 90% or 95% of the target genomic regions in list 4 of PCT/US2020/015082.

Example 8: Additional Select Human Genomic Regions Used for Bins

In some embodiments of the present disclosure, each bin in the plurality of bins is drawn from a panel of genomic regions that is designed for targeted selection of cancer-specific methylation patterns. In some embodiments, each such genomic region is drawn from Table 2 of International Patent Application No. PCT/US2019/053509, published as WO2020/669350A1, entitled "Methylated Markers and Targeted Methylation Probe Panel," filed Sep. 27, 2019, which is hereby incorporated by reference, including the Sequence Listing referenced therein), reproduced below:

| Name | List | SEQ ID NO range in WO2020/069350 |
|---|---|---|
| Assay Panel 1 | List 1 | 1-1644 |
| Assay Panel 2 | List 2 | 1645-5270 |
| Assay Panel 3 | List 3 | 5271-16837 |
| Assay Panel 3A | List 4 | 16838-25984 |
| Assay Panel 4 | List 5 | 25985-46929 |
| Assay Panel 4A | List 6 | 46930-67335 |
| Assay Panel 5 | List 7 | 67336-101617 |
| Assay Panel 6 | List 8 | 101618-131822 |

The sequence listing of WO2020/669350A1 includes the following information: (1) SEQ ID NO, (2) a sequence identifier that identifies (a) a chromosome or contig on which the CpG site is located and (b) a start and stop position of the region, (3) the sequence corresponding to (2) and (4) whether the region was included based on its hypermethylation or hypomethylation score. The chromosome numbers and the start and stop positions are provided relative to a known human reference genome, GRCh37/hg19. The sequence of GRCh37/hg19 is available from the National Center for Biotechnology Information (NCBI), the Genome Reference Consortium, and the Genome Browser provided by Santa Cruz Genomics Institute.

Generally, a bin can encompass any of the CpG sites included within the start/stop ranges of any of the targeted regions included in Lists 1-8 of WO2020/069350.

In some embodiments, the plurality of bins of the present disclosure includes a separate bin for each of at 200, 500, 1,000, 5,000, 10,000, 15,000, 20,000, 30,000, 40,000, or 50,000 target genomic regions in any one of lists 1-8 of WO2020/069350.

In some embodiments, the plurality of bins of the present disclosure includes a separate bin for each of at least 20%, 30%, 40%, 50%, 60%, 70%, 80%, 90% or 95% of the target genomic regions in any one of lists 1-8 of WO2020/069350.

In some embodiments, the plurality of bins of the present disclosure includes a separate bin for each of at 200, 500, 1,000, 5,000, 10,000, 15,000, 20,000, 30,000, 40,000, or 50,000 target genomic regions in any combination of lists 1-8 of WO2020/069350.

In some embodiments, the plurality of bins of the present disclosure includes a separate bin for each of at least 20%, 30%, 40%, 50%, 60%, 70%, 80%, 90% or 95% of the target genomic regions in any combination of lists 1-8 of WO2020/069350.

Example 9: Additional Select Human Genomic Regions Used for Bins

In some embodiments of the present disclosure, each bin in the plurality of bins is drawn from a panel of genomic regions that is designed for targeted selection of cancer-specific methylation patterns. In some embodiments, each such bin corresponds to a genomic region in any of Table 1-24 of International Patent Application No. PCT/US2019/025358, published as WO2019/195268A2, entitled "Methylated Markers and Targeted Methylation Probe Panels," filed Apr. 2, 2019, which is hereby incorporated by reference.

In some embodiments, each bin of the present disclosure maps to a genomic region listed in Table 1, 2, 3, 4, 5, 6, 7, 8, 9, 10, 11, 12, 13, 14, 15, 16, 17, 18, 19, 20, 21, 22, 23 and/or 24 of WO2019/195268A2.

In some embodiments, an entirety of plurality of the bins of the present disclosure together are configured to map to at least 30%, 40%, 50%, 60%, 70%, 80%, 90% or 95% of the genomic regions in one or more of Tables 1-24 of WO2019/195268A2. In some such embodiments, each bin in the plurality of bins maps to a single unique corresponding genomic region in any of Tables 1-24 of WO2019/195268A2. In some such embodiments, a bin in the plurality of bins maps of the present disclosure map to one, two, three, four, five, six, seven, eight, nine or ten unique corresponding genomic region in any combination of Tables 1-24 of WO2019/195268A2.

In some such embodiments, each bin in the plurality of bins of the present disclosure maps to a single unique corresponding genomic region in any of Tables 2-10 or 16-24 of WO2019/195268A2. In some such embodiments, a bin in the plurality of bins maps to one, two, three, four, five, six, seven, eight, nine or ten unique corresponding genomic region in any combination of Tables 2-10 or 16-24 of WO2019/195268A2.

In some embodiments, an entirety of the plurality of bins of the present disclosure together are configured to map to at least 30%, 40%, 50%, 60%, 70%, 80%, 90% or 95% of the genomic regions in Tables 1, 2, 3, 4, 5, 6, 7, 8, 9, 10, 11, 12, 13, 14, 15, 16, 17, 18, 19, 20, 21, 22, 23, and/or 24 of WO2019/195268A2.

Figure 19:
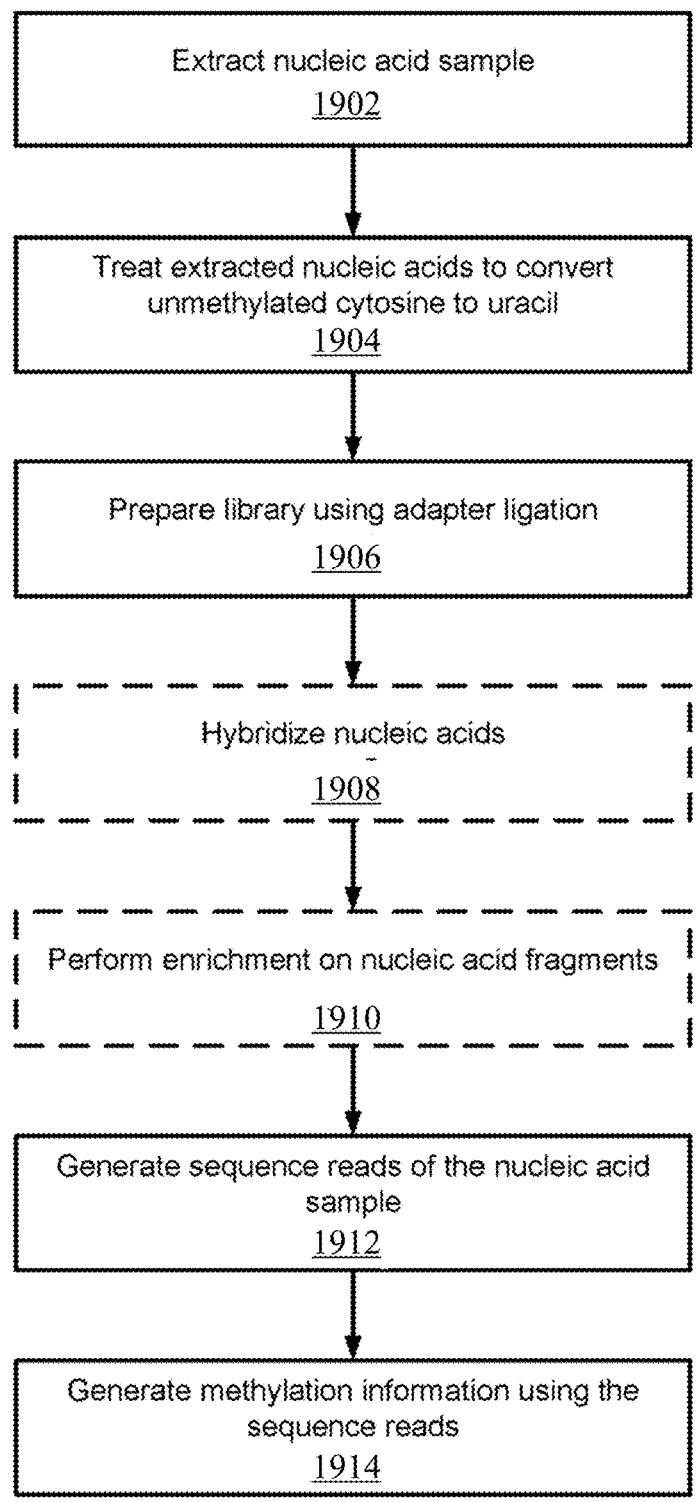
FIG. 19 is a flowchart describing a process of sequencing nucleic acids, in accordance with an aspect of the present disclosure.

Example 10: Protocol for Obtaining Methylation Information from Sequence Reads of Fragments in a Biological Sample FIG. 19 is a flowchart describing a process 1900 of sequencing fragments, according to an embodiment of the present disclosure.

In step 1902, nucleic acid (e.g., DNA or RNA) is extracted from a corresponding biological sample of a respective subject. In the present disclosure, DNA and RNA can be used interchangeably unless otherwise indicated. That is, the embodiments described herein can be applicable to both DNA and RNA types of nucleic acid sequences. However, the examples described herein can focus on DNA for purposes of clarity and explanation. The biological sample can include nucleic acid molecules derived from any subset of the human genome, including the whole genome. The biological sample can include blood, plasma, serum, urine, fecal, saliva, other types of bodily fluids, or any combination thereof. In some embodiments, methods for drawing a blood sample (e.g., syringe or finger prick) can be less invasive than procedures for obtaining a tissue biopsy, which can require surgery. The extracted sample can comprise cfDNA and/or ctDNA. If a subject has a disease state, such as cancer, cell free nucleic acids (e.g., cfDNA) in an extracted sample from the subject generally includes detectable level of the nucleic acids that can be used to assess a disease state.

In step 1904, the extracted nucleic acids (e.g., including cfDNA fragments) are treated to convert unmethylated cytosines to uracils. In some embodiments, the method 1900 uses a bisulfite treatment of the samples that converts the unmethylated cytosines to uracils without converting the methylated cytosines. For example, a commercial kit such as the EZ DNA Methylation™—Gold, EZ DNA Methylation™—Direct or an EZ DNA Methylation™—Lightning kit (available from Zymo Research Corp (Irvine, CA)) is used for the bisulfite conversion. In another embodiment, the conversion of unmethylated cytosines to uracils is accomplished using an enzymatic reaction. For example, the conversion can use a commercially available kit for conversion of unmethylated cytosines to uracils, e.g., APOBEC-Seq (NEBiolabs, Ipswich, MA).

In step 1906, a sequencing library is prepared. In some embodiments, the preparation includes at least two steps. In a first step, an ssDNA adapter is added to the 3'-OH end of a bisulfite-converted ssDNA molecule using a ssDNA ligation reaction. In some embodiments, the ssDNA ligation reaction uses CircLigase II (Epicentre) to ligate the ssDNA adapter to the 3'-OH end of a bisulfite-converted ssDNA molecule, wherein the 5'-end of the adapter is phosphorylated and the bisulfite-converted ssDNA has been dephosphorylated (e.g., the 3' end has a hydroxyl group). In another embodiment, the ssDNA ligation reaction uses Thermostable 5' AppDNA/RNA ligase (available from New England BioLabs (Ipswich, MA)) to ligate the ssDNA adapter to the 3'-OH end of a bisulfite-converted ssDNA molecule. In this example, the first UMI adapter is adenylated at the 5'-end and blocked at the 3'-end. In another embodiment, the ssDNA ligation reaction uses a T4 RNA ligase (available from New England BioLabs) to ligate the ssDNA adapter to the 3'-OH end of a bisulfite-converted ssDNA molecule.

In a second step, a second strand DNA is synthesized in an extension reaction. For example, an extension primer, which hybridizes to a primer sequence included in the ssDNA adapter, is used in a primer extension reaction to form a double-stranded bisulfate-converted DNA molecule. Optionally, in some embodiments, the extension reaction uses an enzyme that is able to read through uracil residues in the bisulfite-converted template strand.

Optionally, in a third step, a dsDNA adapter is added to the double-stranded bisulfite-converted DNA molecule. Then, the double-stranded bisulfite-converted DNA can be amplified to add sequencing adapters. For example, PCR amplification using a forward primer that includes a P5 sequence and a reverse primer that includes a P7 sequence is used to add P5 and P7 sequences to the bisulfite-converted DNA. Optionally, during library preparation, unique molecular identifiers (UMI) can be added to the nucleic acid molecules (e.g., DNA molecules) through adapter ligation.

The UMIs are short nucleic acid sequences (e.g., 4-10 base pairs) that are added to ends of DNA fragments during adapter ligation. In some embodiments, UMIs are degenerate base pairs that serve as a unique tag that can be used to identify sequence reads originating from a specific DNA fragment. During PCR amplification following adapter ligation, the UMIs are replicated along with the attached DNA fragment, which provides a way to identify sequence reads that came from the same original fragment in downstream analysis.

In an optional step 1908, the nucleic acids (e.g., fragments) can be hybridized. Hybridization probes (also referred to herein as "probes") may be used to target, and pull down, nucleic acid fragments informative for disease states. For a given workflow, the probes can be designed to anneal (or hybridize) to a target (complementary) strand of DNA or RNA. The target strand can be the "positive" strand (e.g., the strand transcribed into mRNA, and subsequently translated into a protein) or the complementary "negative" strand. The probes can range in length from 10 s, 100 s, or 1000 s of base pairs. Moreover, the probes can cover overlapping portions of a target region.

In an optional step 1910, the hybridized nucleic acid fragments are captured and can be enriched, e.g., amplified using PCR. In some embodiments, targeted DNA sequences can be enriched from the library. This is used, for example, where a targeted panel assay is being performed on the samples. For example, the target sequences can be enriched to obtain enriched sequences that can be subsequently sequenced. In general, any known method in the art can be used to isolate, and enrich for, probe-hybridized target nucleic acids. For example, as is well known in the art, a biotin moiety can be added to the 5'-end of the probes (i.e., biotinylated) to facilitate isolation of target nucleic acids hybridized to probes using a streptavidin-coated surface (e.g., streptavidin-coated beads).

In step 1912, sequence reads are generated from the nucleic acid sample, e.g., enriched sequences. Sequencing data can be acquired from the enriched DNA sequences by known means in the art. For example, the method can include next generation sequencing (NGS) techniques including synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators.

In step 1914, a sequence processor can generate methylation information using the sequence reads. A methylation state vector can then be generated using the methylation information determined from the sequence reads. FIG. 20 is an illustration of the process 1900 of sequencing a cfDNA molecule to obtain a methylation state vector 2052, according to an embodiment. As an example, a cfDNA fragment is 2012 received that, in this example, contains three CpG sites. As shown, the first and third CpG sites of the cfDNA fragment (molecule) 2012 are methylated 2014. During the treatment step 2015, the cfDNA molecule 2012 is converted to generate a converted cfDNA molecule 2022. During the treatment 2015, the second CpG site which was unmethylated has its cytosine converted to uracil. However, the first and third CpG sites were not converted.

After conversion, a sequencing library is prepared 2035 and sequenced 2040 generating a sequence read 2042. The sequence read 2042 is aligned to a reference genome 2044. The reference genome 2044 provides the context as to what position in a human genome the fragment cfDNA originates from. In this simplified example, the analytics system aligns the sequence read 2042 such that the three CpG sites correlate to CpG sites 23, 24, and 25 (arbitrary reference identifiers used for convenience of description). The disclosed systems and methods thus generate information both on methylation status of all CpG sites on the cfDNA fragment (molecule) 2012 and the position in the human genome that the CpG sites map to. As shown, the CpG sites on sequence read 2042 which were methylated are read as cytosines. In this example, the cytosines appear in the sequence read 2042 only in the first and third CpG site which allows one to infer that the first and third CpG sites in the original cfDNA molecule were methylated. Whereas, the second CpG site is read as a thymine (U is converted to T during the sequencing process), and thus, one can infer that the second CpG site was unmethylated in the original cfDNA molecule. With these two pieces of information, the methylation status and location, the disclosed systems and methods generate a methylation state vector 2052 for the fragment cfDNA 2012. In this example, the resulting methylation state vector 2052 is $<M_{23}, U_{24}, M_{25}>$, where M corresponds to a methylated CpG site, U corresponds to an unmethylated CpG site, and the subscript number corresponds to a position of each CpG site in the reference genome.

CONCLUSION

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event(" or "in response to detecting (the stated condition or event)," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purposes of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A computer system for classifying a test subject to a first cancer condition in a cancer condition set, the cancer condition set comprising two or more cancer conditions, the computer system comprising:
   at least one processor; and
   a memory storing at least one program for execution by the at least one processor, the at least one program comprising instructions for:
      obtaining test genotypic information comprising a corresponding test plurality of bin values, each respective bin value in the test plurality of bin values for a corresponding bin in a plurality of bins, wherein:
         each bin in the plurality of bins represents a portion of a reference genome of a species,
         the test plurality of bin values is obtained from a test biological sample of the test subject, using a corresponding test plurality of sequence reads determined by a first nucleic acid sequencing method,
         the test plurality of sequence reads comprises at least 10,000 sequence reads, and
         the plurality of bins comprises at least 100 bins;
      applying the test plurality of bin values to a machine learning classifier, trained on a transformed second dataset obtained by transfer learning between a first dataset and a second dataset, to cause the machine learning classifier to classify the test subject to the first cancer condition in the cancer condition set, wherein:
         the first dataset comprises, for each respective subject in a first plurality of training subjects, the first plurality of training subjects comprising at least fifty subjects, corresponding first genotypic information comprising (i) a corresponding first plurality of bin values, each respective bin value in the corresponding first plurality of bin values for a corresponding bin in the plurality of bins and (ii) an indication of a cancer condition of the respective subject in the cancer condition set, wherein the corresponding first plurality of bin values of each respective subject in the first plurality of subjects is obtained from a corresponding biological sample of the respective subject, which comprises a first tissue type, using a corresponding first plurality of sequence reads determined by a second nucleic acid sequencing method, and
         the second dataset comprises, for each respective subject in a second plurality of subjects of the species, corresponding second genotypic information comprising (i) a corresponding second plurality of bin values, each respective bin value in the corresponding second plurality of bin values representing a corresponding bin in the plurality of bins and (ii) an indication of a cancer condition of the respective subject in the cancer condition set, and wherein the corresponding second plurality of bin values of each respective subject in the second plurality of subjects is obtained from a corresponding biological sample of the respective subject, which comprises a second tissue type, using a corresponding second plurality of sequence reads determined by a third nucleic acid sequencing method,
         wherein at least the second nucleic acid sequencing method differs from the third nucleic acid sequencing method or the first tissue type differs from the second tissue type;
      wherein the machine learning classifier was trained via:
         obtaining a plurality of feature extraction functions associated with the first dataset by applying a feature extraction technique to the respective bin values of respective subjects in the first dataset, thereby identifying the plurality of feature extraction functions, wherein each feature extraction function in the plurality of feature extraction functions independently encodes a linear or nonlinear function of bin values of all or a subset of the plurality of bins, and the plurality of feature extraction functions collectively discriminates respective subjects in the first plurality of subjects as having a cancer condition within the cancer condition set based on respective bin values for the respective subjects;
         applying each respective feature extraction function in the plurality of feature extraction functions against the respective second plurality of bin values of each corresponding subject in the second plurality of subjects;
         generating, based on the applying, a transformed second dataset comprising a respective plurality of feature values for each corresponding subject in the second plurality of subjects; and
         training, by utilizing the respective plurality of feature values in the transformed second dataset in conjunction with the indication of the cancer condition for each of the second plurality of subjects, the machine learning classifier.

2. The computer system of claim 1, wherein the test plurality of bin values is a number of fragments represented by the test plurality of sequence reads after application of one or more filter conditions.

3. The computer system of claim 2, wherein
the first nucleic acid sequencing method produces a corresponding methylation pattern for each respective fragment in the number of fragments, and
a filter condition in one or more filter conditions is application of a p-value threshold to the corresponding methylation pattern, wherein the p-value threshold is representative of how frequently a methylation pattern is observed in a cohort of non-cancer subjects.

4. The computer system of claim 3, wherein the p-value threshold is between 0.001 and 0.20.

5. The computer system of claim 2, wherein
the first nucleic acid sequencing method produces a corresponding methylation pattern for each respective fragment in the number of fragments, and
a filter condition in the one or more filter conditions is application of a requirement that the respective fragment is represented by a threshold number of sequence reads in the test plurality of sequence reads.

6. The computer system of claim 5, wherein the threshold number is 2, 3, 4, 5, 6, 7, 8, 9, 10, or an integer between 10 and 100.

7. The computer system of claim 2, wherein
the first nucleic acid sequencing method produces a corresponding methylation pattern for each respective fragment in the number of fragments, and
a filter condition in the one or more filter conditions is application of a requirement that the respective fragment have a threshold number of CpG sites.

8. The computer system of claim 7, wherein threshold number of CpG sites is at least 1, 2, 3, 4, 5, 6, 7, 8, 9 or 10 CpG sites.

9. The computer system of claim 2, wherein
the first nucleic acid sequencing method produces a corresponding methylation pattern for each respective fragment in the number of fragments, and
a filter condition in the one or more filter conditions is a requirement that the respective fragment have a length of less than a threshold number of base pairs.

10. The computer system of claim 9, wherein the threshold number of base pairs is 1 thousand, 2 thousand, 3 thousand, or 4 thousand contiguous base pairs in length.

11. A method for classifying a test subject to a first cancer condition in a cancer condition set, the cancer condition set comprising two or more cancer conditions, the method comprising:
obtaining test genotypic information comprising a corresponding test plurality of bin values, each respective bin value in the test plurality of bin values for a corresponding bin in a plurality of bins, wherein:
each bin in the plurality of bins represents a portion of a reference genome of a species,
the test plurality of bin values is obtained from a test biological sample of the test subject, using a corresponding test plurality of sequence reads determined by a first nucleic acid sequencing method,
the test plurality of sequence reads comprises at least 10,000 sequence reads, and
the plurality of bins comprises at least 100 bins;
applying the test plurality of bin values to a machine learning classifier, trained on a transformed second dataset obtained by transfer learning between a first dataset and a second dataset, to cause the machine learning classifier to classify the test subject to the first cancer condition in the cancer condition set, wherein:
the first dataset comprises, for each respective subject in a first plurality of training subjects, the first plurality of training subjects comprising at least fifty subjects, corresponding first genotypic information comprising (i) a corresponding first plurality of bin values, each respective bin value in the corresponding first plurality of bin values for a corresponding bin in the plurality of bins and (ii) an indication of a cancer condition of the respective subject in the cancer condition set, wherein the corresponding first plurality of bin values of each respective subject in the first plurality of subjects is obtained from a corresponding biological sample of the respective subject, which comprises a first tissue type, using a corresponding first plurality of sequence reads determined by a second nucleic acid sequencing method, and
the second dataset comprises, for each respective subject in a second plurality of subjects of the species, corresponding second genotypic information comprising (i) a corresponding second plurality of bin values, each respective bin value in the corresponding second plurality of bin values representing a corresponding bin in the plurality of bins and (ii) an indication of a cancer condition of the respective subject in the cancer condition set, and wherein the corresponding second plurality of bin values of each respective subject in the second plurality of subjects is obtained from a corresponding biological sample of the respective subject, which comprises a second tissue type, using a corresponding second plurality of sequence reads determined by a third nucleic acid sequencing method,
wherein at least the second nucleic acid sequencing method differs from the third nucleic acid sequencing method or the first tissue type differs from the second tissue type;
wherein the machine learning classifier was trained via:
obtaining a plurality of feature extraction functions associated with the first dataset by applying a feature extraction technique to the respective bin values of respective subjects in the first dataset, thereby identifying the plurality of feature extraction functions, wherein each feature extraction function in the plurality of feature extraction functions independently encodes a linear or nonlinear function of bin values of all or a subset of the plurality of bins, and the plurality of feature extraction functions collectively discriminates respective subjects in the first plurality of subjects as having a cancer condition within the cancer condition set based on respective bin values for the respective subjects;
applying each respective feature extraction function in the plurality of feature extraction functions against the respective second plurality of bin values of each corresponding subject in the second plurality of subjects;
generating, based on the applying, a transformed second dataset comprising a respective plurality of feature values for each corresponding subject in the second plurality of subjects; and
training, by utilizing the respective plurality of feature values in the transformed second dataset in conjunction with the indication of the cancer condition for each of the second plurality of subjects, the machine learning classifier.

12. The method of claim 11, the method further comprising:
applying a treatment regimen to the test subject based at least in part the first cancer condition identified by the machine learning classifier.

13. The method of claim 12, wherein the treatment regimen comprises applying an agent for cancer to the test subject.

14. The method of claim 13, wherein the agent for cancer is a hormone, an immune therapy, radiography, or a cancer drug.

15. The method of claim 13, wherein the agent for cancer is Lenalidomid, Pembrolizumab, Trastuzumab, Bevacizumab, Rituximab, Ibrutinib, Human Papillomavirus Quadrivalent (Types 6, 11, 16, and 18) Vaccine, Pertuzumab, Pemetrexed, Nilotinib, Nilotinib, Denosumab, Abiraterone acetate, Promacta, Imatinib, Everolimus, Palbociclib, Erlotinib, Bortezomib, or Bortezomib.

16. The method of claim 11, wherein the test subject has been treated with an agent for cancer and the method further comprises:
evaluating a response of the test subject to the agent for cancer using the first cancer condition determined by the machine learning classifier.

17. The method of claim 16, wherein the agent for cancer is a hormone, an immune therapy, radiography, or a cancer drug.

18. The method of claim 16, wherein the agent for cancer is Lenalidomid, Pembrolizumab, Trastuzumab, Bevacizumab, Rituximab, Ibrutinib, Human Papillomavirus Quadrivalent (Types 6, 11, 16, and 18) Vaccine, Pertuzumab, Pemetrexed, Nilotinib, Nilotinib, Denosumab, Abiraterone acetate, Promacta, Imatinib, Everolimus, Palbociclib, Erlotinib, Bortezomib, or Bortezomib.

19. The method of claim 11, wherein the test subject has been treated with an agent for cancer and the method further comprises:
evaluating a response of the test subject to the agent for cancer using the first cancer condition determined by the machine learning classifier.

20. The method of claim 1, wherein the subject has been subjected to a surgical intervention to address the cancer and the method further comprises:
evaluating a response of the test subject to the agent for cancer using the first cancer condition determined by the machine learning classifier.

21. A non-transitory computer-readable storage medium having stored thereon program code instructions that, when executed by a processor, cause the processor to perform a method for classifying a test subject to a first cancer condition in a cancer condition set, the cancer condition set comprising two or more cancer conditions, the method comprising:
obtaining test genotypic information comprising a corresponding test plurality of bin values, each respective bin value in the test plurality of bin values for a corresponding bin in a plurality of bins, wherein
each bin in the plurality of bins represents a portion of a reference genome of a species,
the test plurality of bin values is obtained from a test biological sample of the test subject, using a corresponding test plurality of sequence reads determined by a first nucleic acid sequencing method,
the test plurality of sequence reads comprises at least 10,000 sequence reads, and
the plurality of bins comprises at least 100 bins;
applying the test plurality of bin values to a machine learning classifier, trained on a transformed second dataset obtained by transfer learning between a first dataset and a second dataset, to cause the machine learning classifier to classify the test subject to the first cancer condition in the cancer condition set, wherein:
the first dataset comprises, for each respective subject in a first plurality of training subjects, the first plurality of training subjects comprising at least fifty subjects, corresponding first genotypic information comprising (i) a corresponding first plurality of bin values, each respective bin value in the corresponding first plurality of bin values for a corresponding bin in the plurality of bins and (ii) an indication of a cancer condition of the respective subject in the cancer condition set, wherein the corresponding first plurality of bin values of each respective subject in the first plurality of subjects is obtained from a corresponding biological sample of the respective subject, which comprises a first tissue type, using a corresponding first plurality of sequence reads determined by a second nucleic acid sequencing method, and
the second dataset comprises, for each respective subject in a second plurality of subjects of the species, corresponding second genotypic information comprising (i) a corresponding second plurality of bin values, each respective bin value in the corresponding second plurality of bin values representing a corresponding bin in the plurality of bins and (ii) an indication of a cancer condition of the respective subject in the cancer condition set, and wherein the corresponding second plurality of bin values of each respective subject in the second plurality of subjects is obtained from a corresponding biological sample of the respective subject, which comprises a second tissue type, using a corresponding second plurality of sequence reads determined by a third nucleic acid sequencing method,
wherein at least the second nucleic acid sequencing method differs from the third nucleic acid sequencing method or the first tissue type differs from the second tissue type;
wherein the machine learning classifier was trained via:
obtaining a plurality of feature extraction functions associated with the first dataset by applying a feature extraction technique to the respective bin values of respective subjects in the first dataset, thereby identifying a plurality of feature extraction functions, wherein each feature extraction function in the plurality of feature extraction functions independently encodes a linear or nonlinear function of bin values of all or a subset of the plurality of bins, and the plurality of feature extraction functions collectively discriminates respective subjects in the first plurality of subjects as having a cancer condition within the cancer condition set based on respective bin values for the respective subjects;
applying each respective feature extraction function in the plurality of feature extraction functions against the respective second plurality of bin values of each corresponding subject in the second plurality of subjects;

generating, based on the applying, a transformed second dataset comprising a respective plurality of feature values for each corresponding subject in the second plurality of subjects; and training, by utilizing the respective plurality of feature values in the transformed second dataset in conjunction with the indication of the cancer condition for each of the second plurality of subjects, the machine learning classifier.

* * * * *

UNITED STATES PATENT AND TRADEMARK OFFICE
CERTIFICATE OF CORRECTION

PATENT NO. : 11,869,661 B2
APPLICATION NO. : 16/881928
DATED : January 9, 2024
INVENTOR(S) : M. Cyrus Maher It is certified that error appears in the above-identified patent and that said Letters Patent is hereby corrected as shown below:

In the Claims

In Claim 12, Lines 3-4 (Column 95, Lines 6-7), delete "at least in part" and insert --at least in part on--.

In Claim 20, Line 1 (Column 95, Line 45), delete "1," and replace with "11,".

Signed and Sealed this
Thirtieth Day of July, 2024

Katherine Kelly Vidal
*Director of the United States Patent and Trademark Office*